US009783801B2

(12) United States Patent
Micklem et al.

(10) Patent No.: US 9,783,801 B2
(45) Date of Patent: Oct. 10, 2017

(54) METHODS FOR CREATING AND IDENTIFYING FUNCTIONAL RNA INTERFERENCE ELEMENTS

(71) Applicant: BerGenBio ASA, Bergen (NO)

(72) Inventors: David Micklem, Bergen (NO); James Lorens, Bønes (NO)

(73) Assignee: BerGenBio ASA, Bergen (NO)

( * ) Notice: Subject to any disclaimer, the term of this patent is extended or adjusted under 35 U.S.C. 154(b) by 100 days.

(21) Appl. No.: 14/102,440

(22) Filed: Dec. 10, 2013

(65) Prior Publication Data
US 2014/0194322 A1    Jul. 10, 2014

Related U.S. Application Data

(62) Division of application No. 12/735,222, filed as application No. PCT/US2008/014037 on Dec. 23, 2008, now Pat. No. 8,735,064.

(60) Provisional application No. 61/008,855, filed on Dec. 24, 2007.

(51) Int. Cl.
*C12N 15/11* (2006.01)
*C12P 19/34* (2006.01)
*C12N 15/10* (2006.01)
*C12N 15/64* (2006.01)
*C12N 15/66* (2006.01)
*C12Q 1/68* (2006.01)

(52) U.S. Cl.
CPC ......... *C12N 15/1086* (2013.01); *C12N 15/10* (2013.01); *C12N 15/111* (2013.01); *C12N 15/64* (2013.01); *C12N 15/66* (2013.01); *C12Q 1/6897* (2013.01); *C12N 2310/14* (2013.01); *C12N 2320/10* (2013.01); *C12N 2330/30* (2013.01)

(58) Field of Classification Search
USPC ..... 424/9.1; 435/6.1, 6.11, 91.1, 455, 91.31, 435/6.13, 91.2, 91.21, 91.5; 514/44; 536/23.1, 24.5, 22.1; 506/9
See application file for complete search history.

(56) References Cited

U.S. PATENT DOCUMENTS

| | | | |
|---|---|---|---|
| 5,624,803 | A | 4/1997 | Noonberg et al. |
| 6,130,313 | A | 10/2000 | Li et al. |
| 6,306,600 | B1 | 10/2001 | Kain et al. |
| 6,808,906 | B2 | 10/2004 | Shen et al. |
| 6,956,112 | B2 | 10/2005 | Li et al. |
| 7,205,130 | B2 | 4/2007 | Lorens et al. |
| 7,294,504 | B1 | 11/2007 | Wang |
| 2005/0042641 | A1 | 2/2005 | Mittal et al. |
| 2008/0021205 | A1 | 1/2008 | Blau et al. |
| 2008/0300145 | A1 | 12/2008 | Mittal et al. |
| 2010/0251392 | A1* | 9/2010 | Shen ............ C12N 15/111 800/3 |
| 2011/0076726 | A1 | 3/2011 | Lakey et al. |

FOREIGN PATENT DOCUMENTS

| | | |
|---|---|---|
| EP | 1 411 122 A1 | 4/2004 |
| EP | 1 557 464 A1 | 7/2005 |
| WO | WO 95/10607 | 4/1995 |
| WO | WO 98/41854 | 9/1998 |
| WO | WO 99/54348 | 10/1999 |
| WO | WO 03/076592 | 9/2003 |
| WO | WO 2004/111190 | 12/2004 |
| WO | WO 2005/023991 | 3/2005 |
| WO | WO 2005/059157 | 6/2005 |
| WO | WO 2007/103365 A2 | 9/2007 |

OTHER PUBLICATIONS

Sen et al, Nature Genetics, vol. 36, No. 2, pp. 183-189 (2004).*
International Preliminary Report on Patentability dated Jul. 8, 2010 from International Application No. PCT/US2008/014037.
International Search Report and Written Opinion dated Aug. 14, 2009 from International Application No. PCT/US2008/014037.
Buchholz et al. (2006) "Enzymatically Prepared RNAi Libraries." *Nature Methods*, 3(9): 696-700.
Dinah et al. (2005) "Alternative approach to generate shRNA from cDNA." *Biotechnoques*, 38(4): 629-632.
Du et al. (2006) "Generation of variable and fixed length siRNA from a novel siRNA expression vector." *Biochemical and Biophysical Research Communications*, 345(1): 99-105.
Evensen et al. (2009) "Mural cell associated VEGF is required for organotypic vessel formation." *PloS ONE* 4(6): e5798.

(Continued)

*Primary Examiner* — Jane Zara
(74) *Attorney, Agent, or Firm* — Quine Intellectual Property Law Group, P.C.; Paul Littlepage

(57) ABSTRACT

The invention relates to the control of gene expression. Specifically, the invention provides compositions and methods for the production and use of recombinant nucleic acid molecules that have the ability to specifically downregulate an expressed target gene in vivo. In some aspects, the invention provides methods for producing a hairpin DNA molecule where part of the molecule is derived from an mRNA that is a target for a small interfering RNA (siRNA) derived from the hairpin. In other aspects, the invention provides synthetic hairpin adapter oligonucleotides that are used in the construction of siRNA-producing cassettes. In other aspects, the invention provides methods for testing for the presence or absence of specific inhibitory activity of an RNAi trigger molecule, and in still other aspects, the invention provides methods for identifying an active RNAi trigger molecule from a library of RNAi trigger molecules. In still other aspects, the invention provides methods for identifying a polynucleotide from a plurality of candidate target polynucleotides that is specifically targeted by an RNAi trigger molecule. In other aspects, the invention provides epi-allelic series of hypomorphic RNAi trigger molecules specific for any gene of interest, where the series of RNAi trigger molecules have a variety of uses including analysis of gene function and drug target development.

17 Claims, 36 Drawing Sheets

(56) References Cited

OTHER PUBLICATIONS

Gjerdrum et al. (2010) "Axl is an essential epithelial-to-mesenchymal transition-induced regulator of breast cancer metastasis and patient survival." *Proc. Natl. Acad. Sci. USA* 107(3): 1124-1129.

Lorens et al. (2001) "The use of retroviruses as pharmaceutical tools for target discovery and validation in the field of functional genomics." *Curr. Op. Biotechol.* 12: 613-621.

Luo et al. (2004) "Small interfering RNA production by enzymatic engineering of DNA (SPEED)." *Proceeding of the National Academy of Science, USA*, 101(15): 5494-5499.

Micklem et al. (2007) "RNAi screening for therapeutic targets in human malignancies." *Curr. Pharm. Biotechnol.* 8(6) 337-343.

Rana (2007) "Illuminating the silence: understanding the structure and function of small RNAs." *Nautre Reviews Molecular Cell Biology*, 8: 23-36.

Scherr et al. (2007) "Gene silencing by small regulatory RNAs in mammalian cells." *Cell Cycle*, 6(4): 444-449.

Sen et al. (2004) "Restriction enzyme-generated siRNA (REGS) vectors and libraries." *Nat. Genetics* 36(2): 183-189.

\* cited by examiner

Generating shRNA expression cassette from hairpin tags

C) Gel purify.
D) Subclone into a suitable expression cassette by digesting with cloning enzymes. In a preferred method, this isn't required as the opened out loop is already attached to the vector. All that is required is to circularize the vector by ligation.
E) If necessary, subclone the expression cassette into an appropriate vector, e.g., a retroviral expression vector.
F) Transcribe the expression cassette in a host cell to produce a candidate shRNA.

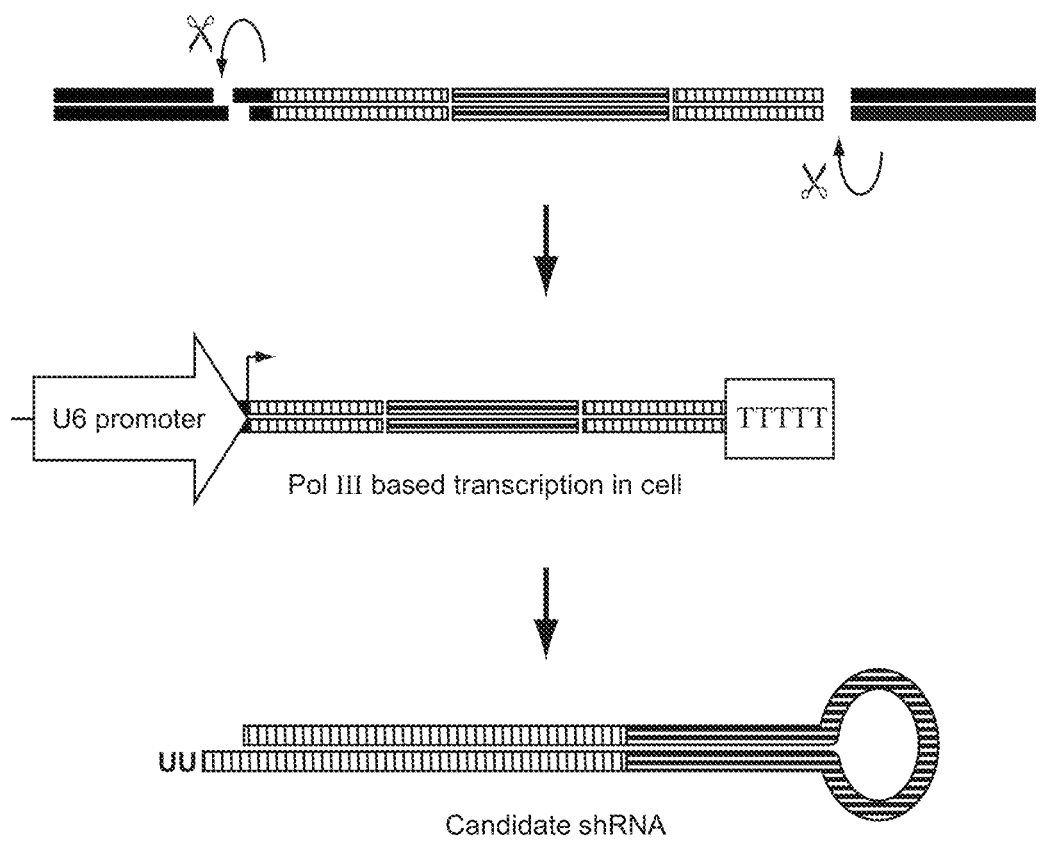

Fig. 4B

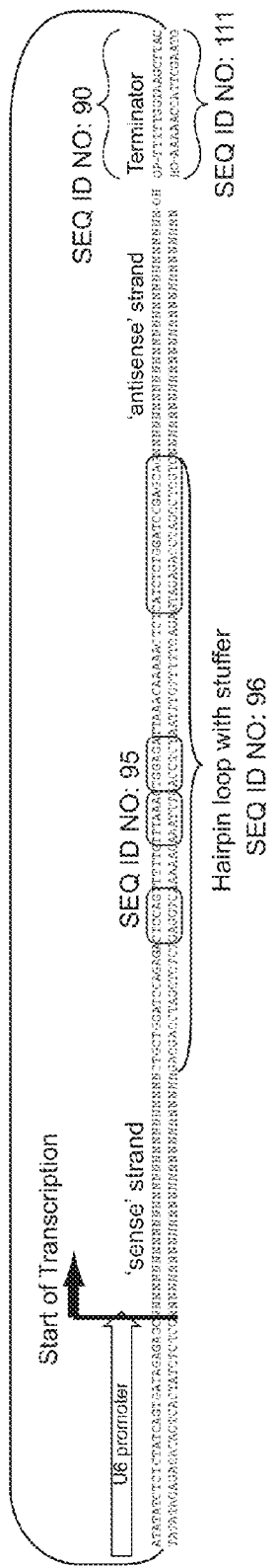
Fig. 15
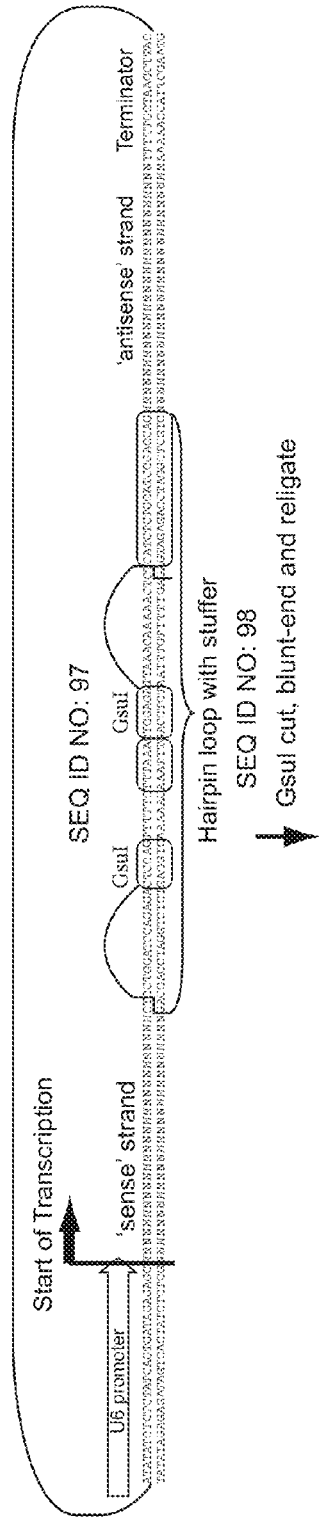
Fig. 16
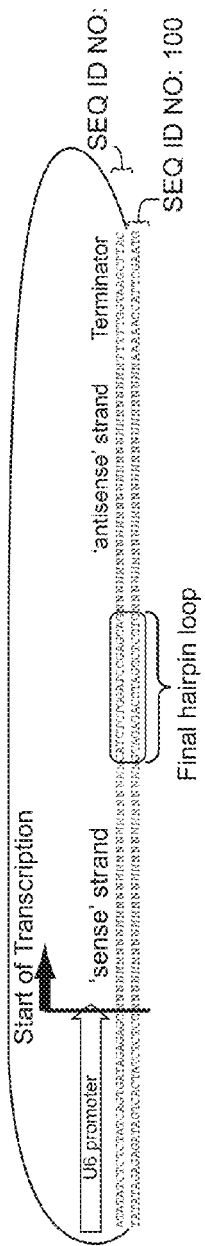

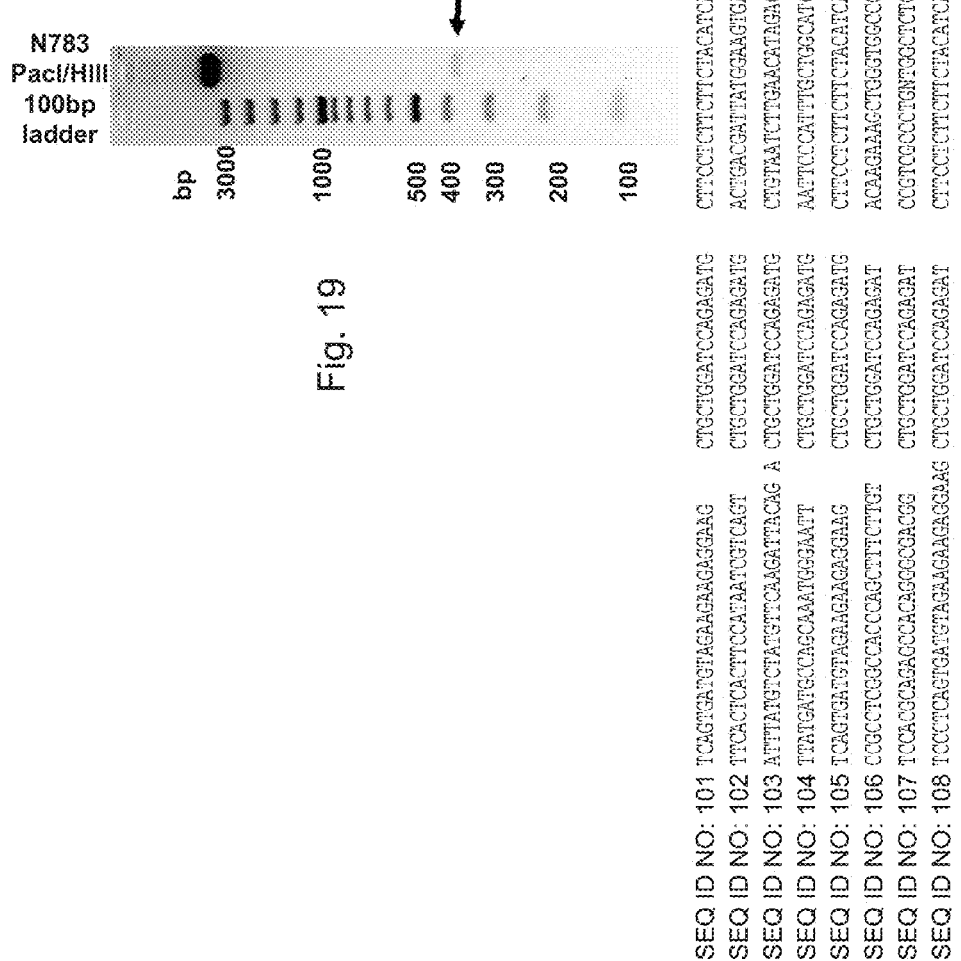

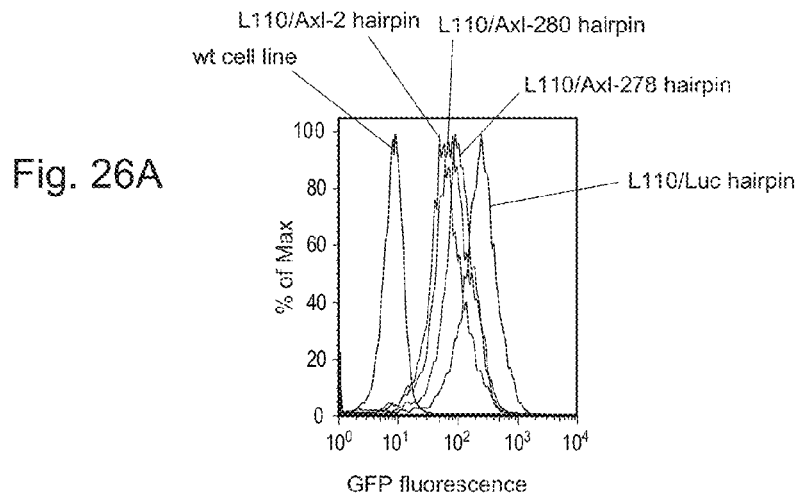
Fig. 26A
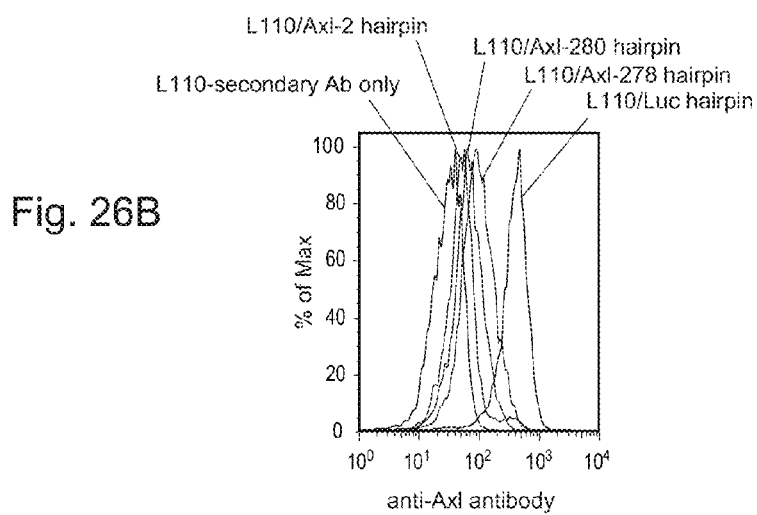
Fig. 26B
Fig. 26C
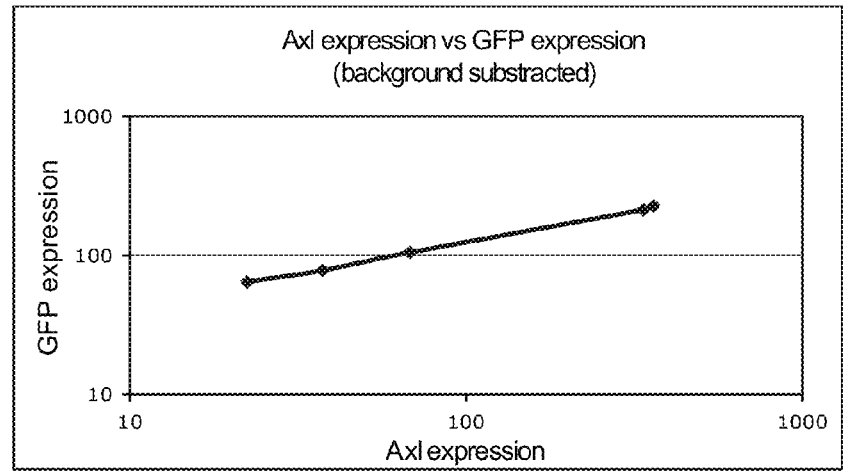

☐ Medium with FBS
☰ Growth Factor Reduced Matrigel™ Matrix
▥ Membrane with 8 mm pores
▦ Serum-free medium
○ Cells

| Proteasomal subunit beta 5 | | |
|---|---|---|
| shRNA Hairpin Sequence | Corresponding mRNA target sequence | Relative Activity |
| gacctctatgtgttaccagtcattaatgaCTGGTCtcattaatg actgtaacacatagaggtc (SEQ ID NO: 1)<br><br>Orientation: sense-LOOP-antisense | GACCTCTATGTGTTACCAGTCATTAATGA<br><br>(SEQ ID NO: 16) | Strong |
| gaatctatgagcttcgaaataaggaacgcCTGGTCgcgttcctt atttcgaagctcatagattc (SEQ ID NO: 2)<br><br>Orientation: sense-LOOP-antisense | GAATCTATGAGCTTCGAAATAAGGAACGC<br><br>(SEQ ID NO: 17) | Strong |
| gatctacatgagaagtatagtggctctacCTGGTCgtagagcca ctatactctcatgtagatc (SEQ ID NO: 3)<br><br>Orientation: sense-LOOP-antisense | GATCTACATGAGAAGTATAGTGGCTCTAC<br><br>(SEQ ID NO: 18) | Intermediate |

Fig. 37

Axl Receptor Tyrosine Kinase

| Name | shRNA Hairpin Sequence | Corresponding mRNA target sequence | Relative Activity |
|---|---|---|---|
| shAxl21 | atgcacgcccagcccgcacagcgTTGGATCCCTGGTCGGATCCAA cgctgtgcggctgggcgtgcat (SEQ ID NO: 4)<br>Orientation: antisense-LOOP-sense | CGCTGTGCGGCTGGGCGTGCAT<br>(SEQ ID NO: 19) | Strong |
| shAxl13 | acgggtctccttctttcgccgTTGGATCCCTGGTCGGATCCAAc ggcgaaagaaggagacccgt (SEQ ID NO: 5)<br>Orientation: antisense-LOOP-sense | CGGCGAAAGAAGGAGACCCGT<br>(SEQ ID NO: 20) | Intermediate |
| shAxl18 | gcttcaggcgattcccccggcgTTGGATCCCTGGTCGGATCCAA cgccggggaaatcgcctgaagc (SEQ ID NO: 6)<br>Orientation: antisense-LOOP-sense | CGCCGGGGAAATCGCCTGAAGC<br>(SEQ ID NO: 21) | Weak |

Fig. 37 cont'd

| Akt serine/threonine-specific protein kinase | |
|---|---|
| shRNA Hairpin Sequence | Corresponding mRNA target sequence |
| atcctcatggaggagatccgcttcccgCTGCTGGATCCAGAGATgcgggaagc<br>ggatctcctccatgaggat (SEQ ID NO: 7)<br><br>Orientation: sense-LOOP-antisense | ATCCTCATGGAGGAGATCCGCTTCCCGC<br><br>(SEQ ID NO: 22) |
| cccagcccccaccagtccactgcacggcTGCTGGATCCAGAGATgccgtgcag<br>tggactgtggggctggg (SEQ ID NO: 8)<br><br>Orientation: antisense-LOOP-sense | GCCGTGCAGTGGACTGGTGGGGGCTGGG<br><br>(SEQ ID NO: 23) |
| gtcacgcggtgcttgggcttggcTGCTGGATCCAGAGATgccaagcccaagca<br>ccgcgtgac (SEQ ID NO: 9)<br><br>Orientation: antisense-LOOP-sense | GCCAAGCCCAAGCACCGCGTGAC<br><br>(SEQ ID NO: 24) |
| cttcatggcgtagtagcggTGCTGGATCCAGAGATccgctactacgccatga<br>ag (SEQ ID NO: 10)<br><br>Orientation: antisense-LOOP-sense | CCGCTACTACGCCATGAAG<br><br>(SEQ ID NO: 25) |
| gtggccccacacactcaccgagaaccgcTGCTGGATCCAGAGATggttctcggt<br>gagtgtgggccac (SEQ ID NO: 11)<br><br>Orientation: sense-LOOP-antisense | GTGGCCCCACACACTCACCGAGAACCGC<br><br>(SEQ ID NO: 26) |
| cctttgcgcacacctgagtacctggcTGCTGGATCCAGAGATgccaggtac<br>tcaggtgtgccgcaaaagg (SEQ ID NO: 12)<br><br>Orientation: sense-LOOP-antisense | CCTTTTGCGGCACACCTGAGTACCTGGC<br><br>(SEQ ID NO: 27) |

Fig. 37 cont'd

| Akt serine/threonine-specific protein kinase | |
|---|---|
| shRNA Hairpin Sequence | Corresponding mRNA target sequence |
| ccatgaacgagtttgagtacctgaagcTGCTGGATCCAGAGATcttcaggtac tcaaactcgttcatgg (SEQ ID NO: 13)<br><br>Orientation: sense-LOOP-antisense | CCATGAACGAGTTTGAGTACCTGAAGC<br><br>(SEQ ID NO: 28) |
| aagatcctcaagaagaagtcatcgtggcTGCTGGATCCAGAGATgccacgat gacttccttcttgaggatctt (SEQ ID NO: 14)<br><br>Orientation: sense-LOOP-antisense | AAGATCCTCAAGAAGAAGTCATCGTGGC<br><br>(SEQ ID NO: 29) |
| cctgcactcggagaagaacgtggtgtCTGCTGGATCCAGAGATacaccacgtt cttctccgagtgcagg (SEQ ID NO: 15)<br><br>Orientation: sense-LOOP-antisense | CCTGCACTCGGAGAAGAACGTGGTGT<br><br>(SEQ ID NO: 30) |

Fig. 37 cont'd

SEQUENCE LISTING

<160> NUMBER OF SEQ ID NOS: 109

<210> SEQ ID NO 1
<211> LENGTH: 64
<212> TYPE: DNA
<213> ORGANISM: Artificial Sequence
<220> FEATURE:
<223> OTHER INFORMATION: Engineered shRNA hairpin sequence

<400> SEQUENCE: 1
gacctctatg tgttaccagt cattaatgac tggtctcatt aatgactggt aacacataga        60
ggtc                                                                    64

<210> SEQ ID NO 2
<211> LENGTH: 64

```
<212> TYPE: DNA
<213> ORGANISM: Artificial Sequence
<220> FEATURE:
<223> OTHER INFORMATION: Engineered shRNA hairpin sequence

<400> SEQUENCE: 2
gaatctatga gcttcgaaat aaggaacgcc tggtcgcgtt ccttatttcg aagctcatag    60
attc                                                                64

<210> SEQ ID NO 3
<211> LENGTH: 64
<212> TYPE: DNA
<213> ORGANISM: Artificial Sequence
<220> FEATURE:
<223> OTHER INFORMATION: Engineered shRNA hairpin sequence

<400> SEQUENCE: 3
gatctacatg agaagtatag tggctctacc tggtcgtaga gccactatac ttctcatgta    60
gatc                                                                64

<210> SEQ ID NO 4
<211> LENGTH: 66
<212> TYPE: DNA
<213> ORGANISM: Artificial Sequence
<220> FEATURE:
<223> OTHER INFORMATION: Engineered shRNA hairpin sequence

<400> SEQUENCE: 4
atgcacgccc agccgcacag cgttggatcc ctggtcggat ccaacgctgt gcggctgggc    60
gtgcat                                                              66

<210> SEQ ID NO 5
<211> LENGTH: 64
<212> TYPE: DNA
<213> ORGANISM: Artificial Sequence
<220> FEATURE:
<223> OTHER INFORMATION: Engineered shRNA hairpin sequence

<400> SEQUENCE: 5
acgggtctcc ttctttcgcc gttggatccc tggtcggatc caacggcgaa agaaggagac    60
ccgt                                                                64

<210> SEQ ID NO 6
<211> LENGTH: 66
<212> TYPE: DNA
<213> ORGANISM: Artificial Sequence
<220> FEATURE:
<223> OTHER INFORMATION: Engineered shRNA hairpin sequence

<400> SEQUENCE: 6
gcttcaggcg atttccccgg cgttggatcc ctggtcggat ccaacgccgg ggaaatcgcc    60
tgaagc                                                              66

<210> SEQ ID NO 7
<211> LENGTH: 72
<212> TYPE: DNA
<213> ORGANISM: Artificial Sequence
<220> FEATURE:
<223> OTHER INFORMATION: Engineered shRNA hairpin sequence

<400> SEQUENCE: 7
atcctcatgg aggagatccg cttcccgctg ctggatccag agatgcggga agcggatctc    60
```
ctccatgagg at                                                          72

<210> SEQ ID NO 8
<211> LENGTH: 72
<212> TYPE: DNA
<213> ORGANISM: Artificial Sequence
<220> FEATURE:
<223> OTHER INFORMATION: Engineered shRNA hairpin sequence

<400> SEQUENCE: 8
cccagccccc accagtccac tgcacggctg ctggatccag agatgccgtg cagtggactg      60 gtggggctg gg                                                           72

<210> SEQ ID NO 9
<211> LENGTH: 62
<212> TYPE: DNA
<213> ORGANISM: Artificial Sequence
<220> FEATURE:
<223> OTHER INFORMATION: Engineered shRNA hairpin sequence

<400> SEQUENCE: 9
gtcacgcggt gcttgggctt ggctgctgga tccagagatg ccaagcccaa gcaccgcgtg      60
ac                                                                     62

<210> SEQ ID NO 10
<211> LENGTH: 55
<212> TYPE: DNA
<213> ORGANISM: Artificial Sequence
<220> FEATURE:
<223> OTHER INFORMATION: Engineered shRNA hairpin sequence

<400> SEQUENCE: 10
cttcatggcg tagtagcggc tgctggatcc agagatccgc tactacgcca tgaag           55

<210> SEQ ID NO 11
<211> LENGTH: 68
<212> TYPE: DNA
<213> ORGANISM: Artificial Sequence
<220> FEATURE:
<223> OTHER INFORMATION: Engineered shRNA hairpin sequence

<400> SEQUENCE: 11
gtggcccaca cactcaccga gaaccgctgc tggatccaga gatggttctc ggtgagtgtg      60
tgggccac                                                               68

<210> SEQ ID NO 12
<211> LENGTH: 72
<212> TYPE: DNA
<213> ORGANISM: Artificial Sequence
<220> FEATURE:
<223> OTHER INFORMATION: Engineered shRNA hairpin sequence

<400> SEQUENCE: 12 cctttttgcgg cacacctgag tacctggctg ctggatccag agatgccagg tactcaggtg     60
tgccgcaaaa gg                                                          72

<210> SEQ ID NO 13
<211> LENGTH: 69
<212> TYPE: DNA
<213> ORGANISM: Artificial Sequence
<220> FEATURE:
<223> OTHER INFORMATION: Engineered shRNA hairpin sequence

<400> SEQUENCE: 13

```
ccatgaacga gtttgagtac ctgaagctgc tggatccaga gatcttcagg tactcaaact      60
cgttcatgg                                                               69

<210> SEQ ID NO 14
<211> LENGTH: 74
<212> TYPE: DNA
<213> ORGANISM: Artificial Sequence
<220> FEATURE:
<223> OTHER INFORMATION: Engineered shRNA hairpin sequence

<400> SEQUENCE: 14
aagatcctca agaaggaagt catcgtggct gctggatcca gagatgccac gatgacttcc      60
ttcttgagga tctt                                                         74

<210> SEQ ID NO 15
<211> LENGTH: 69
<212> TYPE: DNA
<213> ORGANISM: Artificial Sequence
<220> FEATURE:
<223> OTHER INFORMATION: Engineered shRNA hairpin sequence

<400> SEQUENCE: 15
cctgcactcg gagaagaacg tggtgtctgc tggatccaga gatacaccac gttcttctcc      60
gagtgcagg                                                               69

<210> SEQ ID NO 16
<211> LENGTH: 29
<212> TYPE: DNA
<213> ORGANISM: Artificial Sequence
<220> FEATURE:
<223> OTHER INFORMATION: Corresponding mRNA target sequence for SEQ ID
      NO: 1

<400> SEQUENCE: 16
gacctctatg tgttaccagt cattaatga                                         29

<210> SEQ ID NO 17
<211> LENGTH: 29
<212> TYPE: DNA
<213> ORGANISM: Artificial Sequence
<220> FEATURE:
<223> OTHER INFORMATION: Corresponding mRNA target sequence for SEQ ID
      NO: 2

<400> SEQUENCE: 17
gaatctatga gcttcgaaat aaggaacgc                                         29

<210> SEQ ID NO 18
<211> LENGTH: 29
<212> TYPE: DNA
<213> ORGANISM: Artificial Sequence
<220> FEATURE:
<223> OTHER INFORMATION: Corresponding mRNA target sequence for SEQ ID
      NO: 3

<400> SEQUENCE: 18
gatctacatg agaagtatag tggctctac                                         29

<210> SEQ ID NO 19
<211> LENGTH: 22
<212> TYPE: DNA
<213> ORGANISM: Artificial Sequence
<220> FEATURE:
<223> OTHER INFORMATION: Corresponding mRNA target sequence for SEQ ID
```

NO: 4

<400> SEQUENCE: 19
cgctgtgcgg ctgggcgtgc at                                    22

<210> SEQ ID NO 20
<211> LENGTH: 21
<212> TYPE: DNA
<213> ORGANISM: Artificial Sequence
<220> FEATURE:
<223> OTHER INFORMATION: Corresponding mRNA target sequence for SEQ ID
      NO: 5

<400> SEQUENCE: 20
cggcgaaaga aggagacccg t                                     21

<210> SEQ ID NO 21
<211> LENGTH: 22
<212> TYPE: DNA
<213> ORGANISM: Artificial Sequence
<220> FEATURE:
<223> OTHER INFORMATION: Corresponding mRNA target sequence for SEQ ID
      NO: 6

<400> SEQUENCE: 21
cgccggggaa atcgcctgaa gc                                    22

<210> SEQ ID NO 22
<211> LENGTH: 28
<212> TYPE: DNA
<213> ORGANISM: Artificial Sequence
<220> FEATURE:
<223> OTHER INFORMATION: Corresponding mRNA target sequence for SEQ ID
      NO: 7

<400> SEQUENCE: 22
atcctcatgg aggagatccg cttcccgc                              28

<210> SEQ ID NO 23
<211> LENGTH: 28
<212> TYPE: DNA
<213> ORGANISM: Artificial Sequence
<220> FEATURE:
<223> OTHER INFORMATION: Corresponding mRNA target sequence for SEQ ID
      NO: 8

<400> SEQUENCE: 23
gccgtgcagt ggactggtgg gggctggg                              28

<210> SEQ ID NO 24
<211> LENGTH: 23
<212> TYPE: DNA
<213> ORGANISM: Artificial Sequence
<220> FEATURE:
<223> OTHER INFORMATION: Corresponding mRNA target sequence for SEQ ID
      NO: 9

<400> SEQUENCE: 24
gccaagccca agcaccgcgt gac                                   23

<210> SEQ ID NO 25
<211> LENGTH: 19
<212> TYPE: DNA
<213> ORGANISM: Artificial Sequence
<220> FEATURE:
<223> OTHER INFORMATION: Corresponding mRNA target sequence for SEQ ID
      NO: 10

-continued

<400> SEQUENCE: 25
ccgctactac gccatgaag					19

<210> SEQ ID NO 26
<211> LENGTH: 27
<212> TYPE: DNA
<213> ORGANISM: Artificial Sequence
<220> FEATURE:
<223> OTHER INFORMATION: Corresponding mRNA target sequence for SEQ ID
      NO: 11

<400> SEQUENCE: 26
gtggcccaca cactcaccga gaaccgc				27

<210> SEQ ID NO 27
<211> LENGTH: 28
<212> TYPE: DNA
<213> ORGANISM: Artificial Sequence
<220> FEATURE:
<223> OTHER INFORMATION: Corresponding mRNA target sequence for SEQ ID
      NO: 12

<400> SEQUENCE: 27 cctttttgcgg cacacctgag tacctggc				28

<210> SEQ ID NO 28
<211> LENGTH: 27
<212> TYPE: DNA
<213> ORGANISM: Artificial Sequence
<220> FEATURE:
<223> OTHER INFORMATION: Corresponding mRNA target sequence for SEQ ID
      NO: 13

<400> SEQUENCE: 28
ccatgaacga gtttgagtac ctgaagc				27

<210> SEQ ID NO 29
<211> LENGTH: 29
<212> TYPE: DNA
<213> ORGANISM: Artificial Sequence
<220> FEATURE:
<223> OTHER INFORMATION: Corresponding mRNA target sequence for SEQ ID
      NO: 14

<400> SEQUENCE: 29
aagatcctca agaaggaagt catcgtggc				29

<210> SEQ ID NO 30
<211> LENGTH: 26
<212> TYPE: DNA
<213> ORGANISM: Artificial Sequence
<220> FEATURE:
<223> OTHER INFORMATION: Corresponding mRNA target sequence for SEQ ID
      NO: 15

<400> SEQUENCE: 30
cctgcactcg gagaagaacg tggtgt				26

<210> SEQ ID NO 31
<211> LENGTH: 10
<212> TYPE: DNA
<213> ORGANISM: Artificial Sequence
<220> FEATURE:
<223> OTHER INFORMATION: Final loop sequence for use with REGS procedure

<400> SEQUENCE: 31

```
ttggatccaa                                                              10

<210> SEQ ID NO 32
<211> LENGTH: 12
<212> TYPE: DNA
<213> ORGANISM: Artificial Sequence
<220> FEATURE:
<223> OTHER INFORMATION: Exemplary hairpin-adaptor oligo

<400> SEQUENCE: 32
tccaacgttg ga                                                           12

<210> SEQ ID NO 33
<211> LENGTH: 12
<212> TYPE: DNA
<213> ORGANISM: Artificial Sequence
<220> FEATURE:
<223> OTHER INFORMATION: complementary to SEQ ID NO: 32

<400> SEQUENCE: 33
tccaacgttg ga                                                           12

<210> SEQ ID NO 34
<211> LENGTH: 26
<212> TYPE: DNA
<213> ORGANISM: Artificial Sequence
<220> FEATURE:
<223> OTHER INFORMATION: Final loop sequence for use with REGS procedure
<220> FEATURE:
<221> NAME/KEY: misc_feature
<222> LOCATION: (1)..(21)
<223> OTHER INFORMATION: n is a, c, g, t or u

<400> SEQUENCE: 34
nnnnnnnnnn nnnnnnnnnn nttggu                                            26

<210> SEQ ID NO 35
<211> LENGTH: 26
<212> TYPE: DNA
<213> ORGANISM: Artificial Sequence
<220> FEATURE:
<223> OTHER INFORMATION: complementary to SEQ ID NO: 34
<220> FEATURE:
<221> NAME/KEY: misc_feature
<222> LOCATION: (6)..(26)
<223> OTHER INFORMATION: n is a, c, g, or t

<400> SEQUENCE: 35
tccaannnnn nnnnnnnnnn nnnnnn                                            26

<210> SEQ ID NO 36
<211> LENGTH: 22
<212> TYPE: DNA
<213> ORGANISM: Artificial Sequence
<220> FEATURE:
<223> OTHER INFORMATION: DNA intermediate produced during REGS procedure
<220> FEATURE:
<221> NAME/KEY: misc_feature
<222> LOCATION: (1)..(12)
<223> OTHER INFORMATION: n is a, c, g, or t

<400> SEQUENCE: 36
nnnnnnnnnn nncactctcc ag                                                22

<210> SEQ ID NO 37
<211> LENGTH: 22
<212> TYPE: DNA
```

```
<213> ORGANISM: Artificial Sequence
<220> FEATURE:
<223> OTHER INFORMATION: DNA strand complementary to SEQ ID NO: 36
<220> FEATURE:
<221> NAME/KEY: misc_feature
<222> LOCATION: (11)..(22)
<223> OTHER INFORMATION: n is a, c, g, or t

<400> SEQUENCE: 37
ctggagagtg nnnnnnnnnn nn                                          22

<210> SEQ ID NO 38
<211> LENGTH: 18
<212> TYPE: DNA
<213> ORGANISM: Artificial Sequence
<220> FEATURE:
<223> OTHER INFORMATION: DNA intermediate produced during REGS
      procedure, on same strand as SEQ ID NO: 36, but separated by
      intervening DNA.
<220> FEATURE:
<221> NAME/KEY: misc_feature
<222> LOCATION: (7)..(18)
<223> OTHER INFORMATION: n is a, c, g, or t

<400> SEQUENCE: 38
gcagtgnnnn nnnnnnnn                                               18

<210> SEQ ID NO 39
<211> LENGTH: 18
<212> TYPE: DNA
<213> ORGANISM: Artificial Sequence
<220> FEATURE:
<223> OTHER INFORMATION: DNA strand complementary to SEQ ID NO: 38
<220> FEATURE:
<221> NAME/KEY: misc_feature
<222> LOCATION: (1)..(12)
<223> OTHER INFORMATION: n is a, c, g, or t

<400> SEQUENCE: 39
nnnnnnnnnn nncactgc                                               18

<210> SEQ ID NO 40
<211> LENGTH: 12
<212> TYPE: DNA
<213> ORGANISM: Artificial Sequence
<220> FEATURE:
<223> OTHER INFORMATION: Product of bpmI digesting of dsDNA comprising
      SEQ ID NOs: 36 and 38 on one strand and SEQ ID NOs: 37 and 39 on
      complementary
      strand
<220> FEATURE:
<221> NAME/KEY: misc_feature
<222> LOCATION: (1)..(12)
<223> OTHER INFORMATION: n is a, c, g, or t

<400> SEQUENCE: 40
nnnnnnnnnn nn                                                     12

<210> SEQ ID NO 41
<211> LENGTH: 74
<212> TYPE: DNA
<213> ORGANISM: Artificial Sequence
<220> FEATURE:
<223> OTHER INFORMATION: Example of EcoP15I-based hairpin adapter oligo

<400> SEQUENCE: 41
ctgctggatc cagagatgag agttttttgtt taatctccag tttaaacaaa aactggagtc   60
tctggatcca gcag                                                   74
```

```
<210> SEQ ID NO 42
<211> LENGTH: 74
<212> TYPE: DNA
<213> ORGANISM: Artificial Sequence
<220> FEATURE:
<223> OTHER INFORMATION: Example of hairpin oligonucleotide containing
      a methyl-C, e.g., at 69th C (4th nucleotide from 3' end)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(34)
<223> OTHER INFORMATION: n is a, c, g, or t
<220> FEATURE:
<221> NAME/KEY: misc_feature
<222> LOCATION: (48)..(52)
<223> OTHER INFORMATION: n is a, c, g, or t
<220> FEATURE:
<221> NAME/KEY: misc_feature
<222> LOCATION: (59)..(69)
<223> OTHER INFORMATION: n is a, c, g, or t
<220> FEATURE:
<221> NAME/KEY: misc_feature
<222> LOCATION: (72)..(74)
<223> OTHER INFORMATION: n is a, c, g, or t

<400> SEQUENCE: 42
nnngcnnnnn nnnnnnnnnn nnnnnnnnnn nnnnctccag tttaaacnnn nnctggagnn    60
nnnnnnnnng cnnn                                                      74

<210> SEQ ID NO 43
<211> LENGTH: 69
<212> TYPE: DNA
<213> ORGANISM: Artificial Sequence
<220> FEATURE:
<223> OTHER INFORMATION: Example of hairpin oligonucleotide containing
      a methyl-C e.g., at 65th C (5th nucleotide from 3' end)

<400> SEQUENCE: 43
gtgtgctgga tccacactcc agttttttgtt taaactggag attaaacaaa aactctggat   60
ccagcacac                                                            69

<210> SEQ ID NO 44
<211> LENGTH: 74
<212> TYPE: DNA
<213> ORGANISM: Artificial Sequence
<220> FEATURE:
<223> OTHER INFORMATION: Example of McrBC-based hairpin-adaptor oligo
      for use in cloning, contains methyl C at, e.g., 70th C (4th
      nucleotide from 3' end)
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (8)..(20)
<223> OTHER INFORMATION: n is a, c, g, or t
<220> FEATURE:
<221> NAME/KEY: misc_feature
<222> LOCATION: (23)..(36)
<223> OTHER INFORMATION: n is a, c, g, or t
<220> FEATURE:
<221> NAME/KEY: misc_feature
<222> LOCATION: (50)..(54)
<223> OTHER INFORMATION: n is a, c, g, or t
<220> FEATURE:
<221> NAME/KEY: misc_feature
<222> LOCATION: (61)..(69)
<223> OTHER INFORMATION: n is a, c, g, or t
```

```
<220> FEATURE:
<221> NAME/KEY: misc_feature
<222> LOCATION: (72)..(74)
<223> OTHER INFORMATION: n is a, c, g, or t

<400> SEQUENCE: 44
cgnnngcnnn nnnnnnnnnn cgnnnnnnnn nnnnnnctcc agtttaaacn nnnnctggag      60
nnnnnnnnng cnnn                                                        74

<210> SEQ ID NO 45
<211> LENGTH: 44
<212> TYPE: DNA
<213> ORGANISM: Artificial Sequence
<220> FEATURE:
<223> OTHER INFORMATION: Annealed to SEQ ID NO: 46 to produce Y-shaped
      adapter
<220> FEATURE:
<221> NAME/KEY: misc_feature
<222> LOCATION: (43)..(44)
<223> OTHER INFORMATION: n is a, c, g, or t

<400> SEQUENCE: 45
acgtcgacta tccttgaaca gtgccagtga cggaagatct ccnn                       44

<210> SEQ ID NO 46
<211> LENGTH: 42
<212> TYPE: DNA
<213> ORGANISM: Artificial Sequence
<220> FEATURE:
<223> OTHER INFORMATION: Annealed to SEQ ID NO: 45 to produce Y-shaped
      adapter

<400> SEQUENCE: 46
ggagagactc cgtcactggg tgtgcattga gatgcagttg ag                         42

<210> SEQ ID NO 47
<211> LENGTH: 88
<212> TYPE: DNA
<213> ORGANISM: Artificial Sequence
<220> FEATURE:
<223> OTHER INFORMATION: Hairpin oligo that comprises a 2-uracil loop;
      intermediate in producing Y-shaped adaptor
<220> FEATURE:
<221> NAME/KEY: misc_feature
<222> LOCATION: (87)..(88)
<223> OTHER INFORMATION: n is a, c, g, t or u

<400> SEQUENCE: 47
ggagagactc cgtcactggg tgtgcattga gatgcagttg aguuacgtcg actatccttg      60
aacagtgcca gtgacggaag atctccnn                                         88

<210> SEQ ID NO 48
<211> LENGTH: 19
<212> TYPE: DNA
<213> ORGANISM: Artificial Sequence
<220> FEATURE:
<223> OTHER INFORMATION: First strand of Y-shaped adaptor in which one
      of the un base-paired arms has been omitted.  Anneals to SEQ ID
      NO: 49.

<400> SEQUENCE: 48
ccagtgacgg aagatctcc                                                   19

<210> SEQ ID NO 49
<211> LENGTH: 42
<212> TYPE: DNA
<213> ORGANISM: Artificial Sequence
```

```
<220> FEATURE:
<223> OTHER INFORMATION: Second strand of Y-shaped adaptor in which one
      of the unbase-paired arms has been omitted.  Anneals to SEQ ID
      NO: 48.

<400> SEQUENCE: 49
ggagagactc cgtcactggg tgtgcattga gatgcagttg ag                         42

<210> SEQ ID NO 50
<211> LENGTH: 65
<212> TYPE: DNA
<213> ORGANISM: Artificial Sequence
<220> FEATURE:
<223> OTHER INFORMATION: Stem loop sequence that can be produced when
      one un base-paired arm of a Y-shaped adapter is omitted.
<220> FEATURE:
<221> NAME/KEY: misc_feature
<222> LOCATION: (64)..(65)
<223> OTHER INFORMATION: n is a, c, g, t or u

<400> SEQUENCE: 50
ggagagactc cgtcactggg tgtgcattga gatgcagttg aguuccagtg acggaagatc      60 tccnn                                                                 65

<210> SEQ ID NO 51
<211> LENGTH: 21
<212> TYPE: DNA
<213> ORGANISM: Artificial Sequence
<220> FEATURE:
<223> OTHER INFORMATION: First strand of exemplary oligo adapter.
      Anneals to SEQ ID NO: 52.

<400> SEQUENCE: 51
cagagtcggt ctcagatctc c                                               21

<210> SEQ ID NO 52
<211> LENGTH: 48
<212> TYPE: DNA
<213> ORGANISM: Artificial Sequence
<220> FEATURE:
<223> OTHER INFORMATION: Second strand of exemplary oligo adapter.
      Anneals to SEQ ID NO: 51.

<400> SEQUENCE: 52
ggagatctga gaccgactga ctcctgtgtg aaattgttat ccgctggg                  48

<210> SEQ ID NO 53
<211> LENGTH: 21
<212> TYPE: DNA
<213> ORGANISM: Artificial Sequence
<220> FEATURE:
<223> OTHER INFORMATION: SEQ ID NO: 51 ligated to the blunted product
      of an EcoP15I digest

<400> SEQUENCE: 53
cagagtcggt ctcagatctc c                                               21

<210> SEQ ID NO 54
<211> LENGTH: 54
<212> TYPE: DNA
<213> ORGANISM: Artificial Sequence
<220> FEATURE:
<223> OTHER INFORMATION: SEQ ID NO: 52 ligated to the blunted product
      of an EcoP15I digest
<220> FEATURE:
<221> NAME/KEY: misc_feature
<222> LOCATION: (1)..(6)
<223> OTHER INFORMATION: n is a, c, g, or t
```

<400> SEQUENCE: 54
nnnnnnggag atctgagacc gactgactcc tgtgtgaaat tgttatccgc tggg        54

<210> SEQ ID NO 55
<211> LENGTH: 54
<212> TYPE: DNA
<213> ORGANISM: Artificial Sequence
<220> FEATURE:
<223> OTHER INFORMATION: Intermediate in producing cassette ready to
      clone. (Anneals to SEQ ID NO: 54).
<220> FEATURE:
<221> NAME/KEY: misc_feature
<222> LOCATION: (49)..(54)
<223> OTHER INFORMATION: n is a, c, g, or t

<400> SEQUENCE: 55
cccagcggat aacaatttca cacaggagtc agtcggtctc agatctccnn nnnn        54

<210> SEQ ID NO 56
<211> LENGTH: 13
<212> TYPE: DNA
<213> ORGANISM: Artificial Sequence
<220> FEATURE:
<223> OTHER INFORMATION: 5' most sequence of product formed when DNA
      strand comprising SEQ ID NOs: 55 and 56 is digested w/ Bgl II.
<220> FEATURE:
<221> NAME/KEY: misc_feature
<222> LOCATION: (8)..(13)
<223> OTHER INFORMATION: n is a, c, g, or t

<400> SEQUENCE: 56
gatctccnnn nnn        13

<210> SEQ ID NO 57
<211> LENGTH: 9
<212> TYPE: DNA
<213> ORGANISM: Artificial Sequence
<220> FEATURE:
<223> OTHER INFORMATION: 3' most sequence of product formed when DNA
      strand comprising SEQ ID NOs: 54 and 57 is digested w/ Bgl II.
<220> FEATURE:
<221> NAME/KEY: misc_feature
<222> LOCATION: (1)..(6)
<223> OTHER INFORMATION: n is a, c, g, or t

<400> SEQUENCE: 57 nnnnnngga        9

<210> SEQ ID NO 58
<211> LENGTH: 20
<212> TYPE: DNA
<213> ORGANISM: Artificial Sequence
<220> FEATURE:
<223> OTHER INFORMATION: Sequence at 5' end of stem loop structure of
      Fig 5B.
<220> FEATURE:
<221> NAME/KEY: misc_feature
<222> LOCATION: (1)..(10)
<223> OTHER INFORMATION: n is a, c, g, or t

<400> SEQUENCE: 58
nnnnnnnnnn cactctccag        20

<210> SEQ ID NO 59
<211> LENGTH: 18
<212> TYPE: DNA
<213> ORGANISM: Artificial Sequence
<220> FEATURE:

```
<223> OTHER INFORMATION: Sequence at 3' end of stem loop structure of
      Fig 5B.
<220> FEATURE:
<221> NAME/KEY: misc_feature
<222> LOCATION: (7)..(18)
<223> OTHER INFORMATION: n is a, c, g, or t

<400> SEQUENCE: 59
gcagtgnnnn nnnnnnnn                                                    18

<210> SEQ ID NO 60
<211> LENGTH: 18
<212> TYPE: DNA
<213> ORGANISM: Artificial Sequence
<220> FEATURE:
<223> OTHER INFORMATION: Sequence of DNA segment in cloning intermediate
      depicted in Fig 5D
<220> FEATURE:
<221> NAME/KEY: misc_feature
<222> LOCATION: (1)..(12)
<223> OTHER INFORMATION: n is a, c, g, or t

<400> SEQUENCE: 60
nnnnnnnnnn nncactgc                                                    18

<210> SEQ ID NO 61
<211> LENGTH: 22
<212> TYPE: DNA
<213> ORGANISM: Artificial Sequence
<220> FEATURE:
<223> OTHER INFORMATION: Sequence of DNA segment in cloning intermediate
      depicted in Fig 5D. 3' relative to, but not contiguous with, SEQ
      ID NO: 62.
<220> FEATURE:
<221> NAME/KEY: misc_feature
<222> LOCATION: (11)..(22)
<223> OTHER INFORMATION: n is a, c, g, or t

<400> SEQUENCE: 61
ctggagagtg nnnnnnnnnn nn                                               22

<210> SEQ ID NO 62
<211> LENGTH: 18
<212> TYPE: DNA
<213> ORGANISM: Artificial Sequence
<220> FEATURE:
<223> OTHER INFORMATION: Sequence of DNA segment in cloning intermediate
      depicted in Fig 5D.  Complementary to SEQ ID NO: 62.
<220> FEATURE:
<221> NAME/KEY: misc_feature
<222> LOCATION: (7)..(18)
<223> OTHER INFORMATION: n is a, c, g, or t

<400> SEQUENCE: 62
gcagtgnnnn nnnnnnnn                                                    18

<210> SEQ ID NO 63
<211> LENGTH: 22
<212> TYPE: DNA
<213> ORGANISM: Artificial Sequence
<220> FEATURE:
<223> OTHER INFORMATION: Sequence of DNA segment in cloning intermediate
      depicted in Fig 5D. 5' relative to, but not contiguous with, SEQ
      ID NO: 64. Complementary to SEQ ID NO: 63.
<220> FEATURE:
<221> NAME/KEY: misc_feature
<222> LOCATION: (1)..(12)
<223> OTHER INFORMATION: n is a, c, g, or t

<400> SEQUENCE: 63
```

```
nnnnnnnnnn nncactctcc ag                                              22
```

<210> SEQ ID NO 64
<211> LENGTH: 12
<212> TYPE: DNA
<213> ORGANISM: Artificial Sequence
<220> FEATURE:
<223> OTHER INFORMATION: Fragment with free 3' end that results from
      digestion of strand comprising SEQ ID NOs: 62 and 63 with Bts I
      and Gsu I
<220> FEATURE:
<221> NAME/KEY: misc_feature
<222> LOCATION: (1)..(12)
<223> OTHER INFORMATION: n is a, c, g, or t

<400> SEQUENCE: 64

```
nnnnnnnnnn nn                                                         12
```

<210> SEQ ID NO 65
<211> LENGTH: 6
<212> TYPE: DNA
<213> ORGANISM: Artificial Sequence
<220> FEATURE:
<223> OTHER INFORMATION: Fragment with free 5' end that results from
      digestion of strand comprising SEQ ID NOs: 62 and 63 with Bts I
      and Gsu I

<400> SEQUENCE: 65

```
cactgc                                                                 6
```

<210> SEQ ID NO 66
<211> LENGTH: 10
<212> TYPE: DNA
<213> ORGANISM: Artificial Sequence
<220> FEATURE:
<223> OTHER INFORMATION: Fragment with free 5' end that results from
      digestion of strand comprising SEQ ID NOs: 64 and 65 with Bts I
      and Gsu I
<220> FEATURE:
<221> NAME/KEY: misc_feature
<222> LOCATION: (1)..(10)
<223> OTHER INFORMATION: n is a, c, g, or t

<400> SEQUENCE: 66

```
nnnnnnnnnn                                                            10
```

<210> SEQ ID NO 67
<211> LENGTH: 8
<212> TYPE: DNA
<213> ORGANISM: Artificial Sequence
<220> FEATURE:
<223> OTHER INFORMATION: Fragment with free 3' end that results from
      digestion of strand comprising SEQ ID NOs: 64 and 65 with Bts I
      and Gsu I
<220> FEATURE:
<221> NAME/KEY: misc_feature
<222> LOCATION: (7)..(8)
<223> OTHER INFORMATION: n is a, c, g, or t

<400> SEQUENCE: 67

```
gcagtgnn                                                               8
```

<210> SEQ ID NO 68
<211> LENGTH: 20
<212> TYPE: DNA
<213> ORGANISM: Artificial Sequence
<220> FEATURE:
<223> OTHER INFORMATION: Sequence segment 5' relative to, but not
      contiguous with, SEQ ID NO: 69. Produced by digestion of strand
      comprising SEQ ID NOs: 64 and 65 with Bts I and Gsu I.

```
<220> FEATURE:
<221> NAME/KEY: misc_feature
<222> LOCATION: (1)..(10)
<223> OTHER INFORMATION: n is a, c, g, or t

<400> SEQUENCE: 68
nnnnnnnnnn cactctccag                                              20

<210> SEQ ID NO 69
<211> LENGTH: 22
<212> TYPE: DNA
<213> ORGANISM: Artificial Sequence
<220> FEATURE:
<223> OTHER INFORMATION: Cloning intermediate for general method that
      allows the precise removal of a stuffer fragment.
<220> FEATURE:
<221> NAME/KEY: misc_feature
<222> LOCATION: (1)..(16)
<223> OTHER INFORMATION: n is a, c, g, or t

<400> SEQUENCE: 69
nnnnnnnnnn nnnnnnctcc ag                                           22

<210> SEQ ID NO 70
<211> LENGTH: 27
<212> TYPE: DNA
<213> ORGANISM: Artificial Sequence
<220> FEATURE:
<223> OTHER INFORMATION: Cloning intermediate for general method that
      allows the precise removal of a stuffer fragment .  On same strand
      as, but not contiguous with, SEQ ID NO: 71.
<220> FEATURE:
<221> NAME/KEY: misc_feature
<222> LOCATION: (7)..(22)
<223> OTHER INFORMATION: n is a, c, g, or t

<400> SEQUENCE: 70
ctggagnnnn nnnnnnnnnn nntttt                                       27

<210> SEQ ID NO 71
<211> LENGTH: 22
<212> TYPE: DNA
<213> ORGANISM: Artificial Sequence
<220> FEATURE:
<223> OTHER INFORMATION: Cloning intermediate for general method that
      allows the precise removal of a stuffer fragment .  Hybridizes
      with SEQ ID NO: 71
<220> FEATURE:
<221> NAME/KEY: misc_feature
<222> LOCATION: (7)..(22)
<223> OTHER INFORMATION: n is a, c, g, or t

<400> SEQUENCE: 71
ctggagnnnn nnnnnnnnnn nn                                           22

<210> SEQ ID NO 72
<211> LENGTH: 27
<212> TYPE: DNA
<213> ORGANISM: Artificial Sequence
<220> FEATURE:
<223> OTHER INFORMATION: Cloning intermediate for general method that
      allows the precise removal of a stuffer fragment .  On the same
      strand as, but not contiguous with SEQ ID NO: 73; anneals to SEQ
      ID NO: 72.
<220> FEATURE:
<221> NAME/KEY: misc_feature
<222> LOCATION: (6)..(21)
<223> OTHER INFORMATION: n is a, c, g, or t

<400> SEQUENCE: 72
```

```
aaaaannnnn nnnnnnnnnn ngtccag                                              27
```

```
<210> SEQ ID NO 73
<211> LENGTH: 25
<212> TYPE: DNA
<213> ORGANISM: Artificial Sequence
<220> FEATURE:
<223> OTHER INFORMATION: Cloning intermediate in a method for making a
      library of shRNA cassettes within the same vector.

<400> SEQUENCE: 73
cctcagcggc cgcgcattgc tgctg                                                25

<210> SEQ ID NO 74
<211> LENGTH: 24
<212> TYPE: DNA
<213> ORGANISM: Artificial Sequence
<220> FEATURE:
<223> OTHER INFORMATION: Cloning intermediate in a method for making a
      library of shRNA cassettes within the same vector.  Hybridizes
      with SEQ ID NO: 75.

<400> SEQUENCE: 74
cagcagcatg cgcggccgct gagg                                                 24

<210> SEQ ID NO 75
<211> LENGTH: 19
<212> TYPE: DNA
<213> ORGANISM: Artificial Sequence
<220> FEATURE:
<223> OTHER INFORMATION: Cloning intermediate in a method for making a
      library of shRNA cassettes within the same vector.  Product of
      N.BbvC IA digestion of SEQ ID NO: 76.

<400> SEQUENCE: 75
cagcagcatg cgcggccgc                                                       19

<210> SEQ ID NO 76
<211> LENGTH: 10
<212> TYPE: DNA
<213> ORGANISM: Artificial Sequence
<220> FEATURE:
<223> OTHER INFORMATION: Cloning intermediate in a method for making a
      library of shRNA cassettes within the same vector.

<400> SEQUENCE: 76
cctcatgagg                                                                 10

<210> SEQ ID NO 77
<211> LENGTH: 10
<212> TYPE: DNA
<213> ORGANISM: Artificial Sequence
<220> FEATURE:
<223> OTHER INFORMATION: Cloning intermediate in a method for making a
      library of shRNA cassettes within the same vector.  Hybridizes
      wirh SEQ ID NO: 78.

<400> SEQUENCE: 77
cctcatgagg                                                                 10

<210> SEQ ID NO 78
<211> LENGTH: 10
<212> TYPE: DNA
<213> ORGANISM: Artificial Sequence
<220> FEATURE:
<223> OTHER INFORMATION: Cloning intermediate in a method for making a
      library of shRNA cassettes within the same vector.
```

```
<400> SEQUENCE: 78
cagcagcatg                                                            10

<210> SEQ ID NO 79
<211> LENGTH: 10
<212> TYPE: DNA
<213> ORGANISM: Artificial Sequence
<220> FEATURE:
<223> OTHER INFORMATION: Cloning intermediate in a method for making a
      library of shRNA cassettes within the same vector.

<400> SEQUENCE: 79
gagtcagcag                                                            10

<210> SEQ ID NO 80
<211> LENGTH: 10
<212> TYPE: DNA
<213> ORGANISM: Artificial Sequence
<220> FEATURE:
<223> OTHER INFORMATION: Cloning intermediate in a method for making a
      library of shRNA cassettes within the same vector.  Hybridizes
      to SEQ ID NO: 81.

<400> SEQUENCE: 80
ctgctgactc                                                            10

<210> SEQ ID NO 81
<211> LENGTH: 74
<212> TYPE: DNA
<213> ORGANISM: Artificial Sequence
<220> FEATURE:
<223> OTHER INFORMATION: Sequence of stem loop structure in Fig 9

<400> SEQUENCE: 81
ctgctggatc cagagactcc agttttttgtt taaactggag attaaacaaa aactctcatc    60
tctggatcca gcag                                                       74

<210> SEQ ID NO 82
<211> LENGTH: 70
<212> TYPE: DNA
<213> ORGANISM: Artificial Sequence
<220> FEATURE:
<223> OTHER INFORMATION: Sequence of stem loop structure in Fig 10

<400> SEQUENCE: 82
aaacgctgga tccacactcc agtttttatt taaatctgga gattaaataa aaactctgga    60
tccagcgttt                                                            70

<210> SEQ ID NO 83
<211> LENGTH: 82
<212> TYPE: DNA
<213> ORGANISM: Artificial Sequence
<220> FEATURE:
<223> OTHER INFORMATION: Sequence of stem loop structure in Fig 11

<400> SEQUENCE: 83
ctgctggatc cagagactcc agaattgtga gcgctcacaa ttctggagat gagaccttcg    60
gtctcatctc tggatccagc ag                                              82

<210> SEQ ID NO 84
<211> LENGTH: 84
<212> TYPE: DNA
<213> ORGANISM: Artificial Sequence
<220> FEATURE:
```

<223> OTHER INFORMATION: Subsequence of exemplary vector for the
      intermediate cloning of short hairpin RNAs under the control of
      the U6 promoter.

<400> SEQUENCE: 84
atatatctct ctatcagtga tagagagcgc tgtgaaaggc gcgccacctg caaccttttt    60
ccaatgcatt tttggtaagc ttac    84

<210> SEQ ID NO 85
<211> LENGTH: 84
<212> TYPE: DNA
<213> ORGANISM: Artificial Sequence
<220> FEATURE:
<223> OTHER INFORMATION: Subsequence of exemplary vector for the
      intermediate cloning of short hairpin RNAs under the control of
      the U6 promoter. Hybridizes to SEQ ID NO: 86.

<400> SEQUENCE: 85
gtaagcttac caaaaatgca ttggaaaaag gttgcaggtg gcgcgccttt cacagcgctc    60
tctatcactg atagagagat atat    84

<210> SEQ ID NO 86
<211> LENGTH: 28
<212> TYPE: DNA
<213> ORGANISM: Artificial Sequence
<220> FEATURE:
<223> OTHER INFORMATION: Subsequence of exemplary vector for the
      intermediate cloning of short hairpin RNAs under the control of
      the U6 promoter, following digested with AfeI and XcmI

<400> SEQUENCE: 86
atatatctct ctatcagtga tagagagc    28

<210> SEQ ID NO 87
<211> LENGTH: 28
<212> TYPE: DNA
<213> ORGANISM: Artificial Sequence
<220> FEATURE:
<223> OTHER INFORMATION: Subsequence of exemplary vector for the
      intermediate cloning of short hairpin RNAs under the control of
      the U6 promoter, following digested with AfeI and XcmI.
      Hybridizes to SEQ ID NO: 88

<400> SEQUENCE: 87
gctctctatc actgatagag agatatat    28

<210> SEQ ID NO 88
<211> LENGTH: 16
<212> TYPE: DNA
<213> ORGANISM: Artificial Sequence
<220> FEATURE:
<223> OTHER INFORMATION: Subsequence of exemplary vector for the
      intermediate cloning of short hairpin RNAs under the control of
      the U6 promoter, following digested with AfeI and XcmI.

<400> SEQUENCE: 88 ttttggtaa gcttac    16

<210> SEQ ID NO 89
<211> LENGTH: 16
<212> TYPE: DNA
<213> ORGANISM: Artificial Sequence
<220> FEATURE:
<223> OTHER INFORMATION: Subsequence of exemplary vector for the
      intermediate cloning of short hairpin RNAs under the control of
      the U6 promoter, following digested with AfeI and XcmI. Hybridizes
      to SEQ ID NO: 90.

```
<400> SEQUENCE: 89
gtaagcttac caaaat                                                      16

<210> SEQ ID NO 90
<211> LENGTH: 128
<212> TYPE: DNA
<213> ORGANISM: Artificial Sequence
<220> FEATURE:
<223> OTHER INFORMATION: Sequence of stem-loop intermediate depicted
      in Fig 13
<220> FEATURE:
<221> NAME/KEY: misc_feature
<222> LOCATION: (1)..(27)
<223> OTHER INFORMATION: n is a, c, g, or t
<220> FEATURE:
<221> NAME/KEY: misc_feature
<222> LOCATION: (102)..(128)
<223> OTHER INFORMATION: n is a, c, g, or t

<400> SEQUENCE: 90
nnnnnnnnnn nnnnnnnnnn nnnnnnnctg ctggatccag agactccagt ttttgtttaa      60
actggagatt aaacaaaaac tctcatctct ggatccagca gnnnnnnnnn nnnnnnnnnn     120 nnnnnnnn                                                             128

<210> SEQ ID NO 91
<211> LENGTH: 156
<212> TYPE: DNA
<213> ORGANISM: Artificial Sequence
<220> FEATURE:
<223> OTHER INFORMATION: Sequence of stem-loop intermediate depicted in
      Fig 13
<220> FEATURE:
<221> NAME/KEY: misc_feature
<222> LOCATION: (1)..(27)
<223> OTHER INFORMATION: n is a, c, g, or t
<220> FEATURE:
<221> NAME/KEY: misc_feature
<222> LOCATION: (102)..(128)
<223> OTHER INFORMATION: n is a, c, g, or t

<400> SEQUENCE: 91
nnnnnnnnnn nnnnnnnnnn nnnnnnnctg ctggatccag agactccagt ttttgtttaa      60
actggagatt aaacaaaaac tctcatctct ggatccagca gnnnnnnnnn nnnnnnnnnn     120
nnnnnnnngc tctctatcac tgatagagag atatat                              156

<210> SEQ ID NO 92
<211> LENGTH: 50
<212> TYPE: DNA
<213> ORGANISM: Artificial Sequence
<220> FEATURE:
<223> OTHER INFORMATION: Cloning intermediate in vector construction
      of the invention.
<220> FEATURE:
<221> NAME/KEY: misc_feature
<222> LOCATION: (29)..(50)
<223> OTHER INFORMATION: n is a, c, g, or t

<400> SEQUENCE: 92
atatatctct ctatcagtga tagagagcnn nnnnnnnnn nnnnnnnnnn                  50

<210> SEQ ID NO 93
<211> LENGTH: 155
<212> TYPE: DNA
<213> ORGANISM: Artificial Sequence
<220> FEATURE:
<223> OTHER INFORMATION: Exemplary cloning intermediate from Fig 15
```

```
<220> FEATURE:
<221> NAME/KEY: misc_feature
<222> LOCATION: (29)..(55)
<223> OTHER INFORMATION: n is a, c, g, or t
<220> FEATURE:
<221> NAME/KEY: misc_feature
<222> LOCATION: (129)..(155)
<223> OTHER INFORMATION: n is a, c, g, or t

<400> SEQUENCE: 93
atatatctct ctatcagtga tagagagcnn nnnnnnnnnn nnnnnnnnnn nnnnntgctg      60
gatccagaga ctccagtttt tgtttaaact ggagattaaa caaaaactct catctctgga    120
tccagcagnn nnnnnnnnnn nnnnnnnnnn nnnnn                               155

<210> SEQ ID NO 94
<211> LENGTH: 157
<212> TYPE: DNA
<213> ORGANISM: Artificial Sequence
<220> FEATURE:
<223> OTHER INFORMATION: Exemplary cloning intermediate from Fig 15;
      complementary to SEQ ID NO: 95
<220> FEATURE:
<221> NAME/KEY: misc_feature
<222> LOCATION: (1)..(27)
<223> OTHER INFORMATION: n is a, c, g, or t
<220> FEATURE:
<221> NAME/KEY: misc_feature
<222> LOCATION: (103)..(129)
<223> OTHER INFORMATION: n is a, c, g, or t

<400> SEQUENCE: 94
nnnnnnnnnn nnnnnnnnnn nnnnnnnctg ctcggatcca gagatgagag tttttgttta     60
atctccagtt taaacaaaaa ctggagtctc tggatccagc agnnnnnnnn nnnnnnnnnn    120
nnnnnnnnng ctctctatca ctgatagaga gatatat                            157

<210> SEQ ID NO 95
<211> LENGTH: 171
<212> TYPE: DNA
<213> ORGANISM: Artificial Sequence
<220> FEATURE:
<223> OTHER INFORMATION: Exemplary cloning intermediate from Fig 16
<220> FEATURE:
<221> NAME/KEY: misc_feature
<222> LOCATION: (29)..(55)
<223> OTHER INFORMATION: n is a, c, g, or t
<220> FEATURE:
<221> NAME/KEY: misc_feature
<222> LOCATION: (129)..(155)
<223> OTHER INFORMATION: n is a, c, g, or t

<400> SEQUENCE: 95
atatatctct ctatcagtga tagagagcnn nnnnnnnnnn nnnnnnnnnn nnnnntgctg      60
gatccagaga ctccagtttt tgtttaaact ggagattaaa caaaaactct catctctgga    120
tccagcagnn nnnnnnnnnn nnnnnnnnnn nnnnttttt ggtaagctta c              171

<210> SEQ ID NO 96
<211> LENGTH: 173
<212> TYPE: DNA
<213> ORGANISM: Artificial Sequence
<220> FEATURE:
<223> OTHER INFORMATION: Exemplary cloning intermediate from Fig 16,
      complementary to SEQ ID NO: 97.
<220> FEATURE:
<221> NAME/KEY: misc_feature
<222> LOCATION: (17)..(43)
<223> OTHER INFORMATION: n is a, c, g, or t
<220> FEATURE:
```

<221> NAME/KEY: misc_feature
<222> LOCATION: (119)..(145)
<223> OTHER INFORMATION: n is a, c, g, or t

<400> SEQUENCE: 96
gtaagcttac caaaaannnn nnnnnnnnnn nnnnnnnnnn nnnctgctcg gatccagaga    60
tgagagtttt tgtttaatct ccagtttaaa caaaaactgg agtctctgga tccagcagnn   120
nnnnnnnnnn nnnnnnnnnn nnnnngctct ctatcactga tagagagata tat          173

<210> SEQ ID NO 97
<211> LENGTH: 116
<212> TYPE: DNA
<213> ORGANISM: Artificial Sequence
<220> FEATURE:
<223> OTHER INFORMATION: Exemplary sequence of vector where stuffer
      sequence from the cloned opened-out hairpin construct has been
      removed.
<220> FEATURE:
<221> NAME/KEY: misc_feature
<222> LOCATION: (29)..(55)
<223> OTHER INFORMATION: n is a, c, g, or t
<220> FEATURE:
<221> NAME/KEY: misc_feature
<222> LOCATION: (74)..(100)
<223> OTHER INFORMATION: n is a, c, g, or t

<400> SEQUENCE: 97
atatatctct ctatcagtga tagagagcnn nnnnnnnnnn nnnnnnnnnn nnnnncatct    60
ctggatccag cagnnnnnnn nnnnnnnnnn nnnnnnnnnn tttttggtaa gcttac        116

<210> SEQ ID NO 98
<211> LENGTH: 117
<212> TYPE: DNA
<213> ORGANISM: Artificial Sequence
<220> FEATURE:
<223> OTHER INFORMATION: Exemplary sequence of vector where stuffer
      sequence from the cloned opened-out hairpin construct has been
      removed; complementary to SEQ ID NO: 99
<220> FEATURE:
<221> NAME/KEY: misc_feature
<222> LOCATION: (17)..(43)
<223> OTHER INFORMATION: n is a, c, g, or t
<220> FEATURE:
<221> NAME/KEY: misc_feature
<222> LOCATION: (63)..(89)
<223> OTHER INFORMATION: n is a, c, g, or t

<400> SEQUENCE: 98
gtaagcttac caaaaannnn nnnnnnnnnn nnnnnnnnnn nnnctgctcg gatccagaga    60
tgnnnnnnnn nnnnnnnnnn nnnnnnnnng ctctctatca ctgatagaga gatatat       117

<210> SEQ ID NO 99
<211> LENGTH: 73
<212> TYPE: DNA
<213> ORGANISM: Artificial Sequence
<220> FEATURE:
<223> OTHER INFORMATION: Sequence of a hairpin shRNA cassette obtained
      following VEGFR2/KDR single gene library construction.

<400> SEQUENCE: 99
tcagtgatgt agaagaagag gaagctgctg gatccagaga tgcttcctct tcttctacat    60
cactgaggtt ttt                                                        73

<210> SEQ ID NO 100
<211> LENGTH: 75
<212> TYPE: DNA

<213> ORGANISM: Artificial Sequence
<220> FEATURE:
<223> OTHER INFORMATION: Sequence of a hairpin shRNA cassette obtained
      following VEGFR2/KDR single gene library construction.

<400> SEQUENCE: 100
ttcactcact tccataatcg tcagtctgct ggatccagag atgactgacg attatggaag        60
tgagtgaaag ttttt                                                        75

<210> SEQ ID NO 101
<211> LENGTH: 76
<212> TYPE: DNA
<213> ORGANISM: Artificial Sequence
<220> FEATURE:
<223> OTHER INFORMATION: Sequence of a hairpin shRNA cassette obtained
      following VEGFR2/KDR single gene library construction.

<400> SEQUENCE: 101
atttatgtct atgttcaaga ttacagactg ctggatccag agatgctgta atcttgaaca        60
tagacataaa tttttt                                                       76

<210> SEQ ID NO 102
<211> LENGTH: 73
<212> TYPE: DNA
<213> ORGANISM: Artificial Sequence
<220> FEATURE:
<223> OTHER INFORMATION: Sequence of a hairpin shRNA cassette obtained
      following VEGFR2/KDR single gene library construction.

<400> SEQUENCE: 102
ttatgatgcc agcaaatggg aattctgctg gatccagaga tgaattccca tttgctggca        60
tcataaggtt ttt                                                          73

<210> SEQ ID NO 103
<211> LENGTH: 73
<212> TYPE: DNA
<213> ORGANISM: Artificial Sequence
<220> FEATURE:
<223> OTHER INFORMATION: Sequence of a hairpin shRNA cassette obtained
      following VEGFR2/KDR single gene library construction.

<400> SEQUENCE: 103
tcagtgatgt agaagaagag gaagctgctg gatccagaga tgcttcctct tcttctacat        60
cactgaggtt ttt                                                          73

<210> SEQ ID NO 104
<211> LENGTH: 75
<212> TYPE: DNA
<213> ORGANISM: Artificial Sequence
<220> FEATURE:
<223> OTHER INFORMATION: Sequence of a hairpin shRNA cassette obtained
      following VEGFR2/KDR single gene library construction.

<400> SEQUENCE: 104
ccgcctcggc cacccagctt tcttgtctgc tggatccaga gatacaagaa agctgggtgg        60
ccgaggcggc ttttt                                                        75

<210> SEQ ID NO 105
<211> LENGTH: 75
<212> TYPE: DNA
<213> ORGANISM: Artificial Sequence
<220> FEATURE:
<223> OTHER INFORMATION: Sequence of a hairpin shRNA cassette obtained
      following VEGFR2/KDR single gene library construction.

```
<220> FEATURE:
<221> NAME/KEY: misc_feature
<222> LOCATION: (54)..(54)
<223> OTHER INFORMATION: n is a, c, g, or t

<400> SEQUENCE: 105
tccacgcaga gccacagggc gacggctgct ggatccagag atccgtcgcc ctgntggctc    60
tgcgtggaga ttttt                                                     75

<210> SEQ ID NO 106
<211> LENGTH: 78
<212> TYPE: DNA
<213> ORGANISM: Artificial Sequence
<220> FEATURE:
<223> OTHER INFORMATION: Sequence of a hairpin shRNA cassette obtained
      following VEGFR2/KDR single gene library construction.

<400> SEQUENCE: 106
tccctcagtg atgtagaaga agaggaagct gctggatcca gagatcttcc tcttcttcta    60
catcactgag ggattttt                                                  78

<210> SEQ ID NO 107
<211> LENGTH: 21
<212> TYPE: DNA
<213> ORGANISM: Artificial Sequence
<220> FEATURE:
<223> OTHER INFORMATION: Sequence of RNAi trigger molecule identified
      by the invention

<400> SEQUENCE: 107
cgctgtgcgg ctgggcgtgc a                                              21

<210> SEQ ID NO 108
<211> LENGTH: 21
<212> TYPE: DNA
<213> ORGANISM: Artificial Sequence
<220> FEATURE:
<223> OTHER INFORMATION: Sequence of RNAi trigger molecule identified
      by the invention

<400> SEQUENCE: 108
ggcgaaagaa ggagacccgt t                                              21

<210> SEQ ID NO 109
<211> LENGTH: 16
<212> TYPE: DNA
<213> ORGANISM: Artificial Sequence
<220> FEATURE:
<223> OTHER INFORMATION: Complementary to SEQ ID NO: 90 in Fig 15

<400> SEQUENCE: 109
gtaagcttac caaaaa                                                    16
```

METHODS FOR CREATING AND IDENTIFYING FUNCTIONAL RNA INTERFERENCE ELEMENTS

CROSS REFERENCE TO RELATED APPLICATIONS

This application is a divisional of U.S. application Ser. No. 12/735,222, (now U.S. Pat. No. 8,735,064) having a 371 date of Sep. 8, 2010, which is a national phase entry in the United States under 35 U.S.C. §371 from International Application Number PCT/US2008/014037, filed Dec. 23, 2008, which claims priority to and benefit of U.S. Provisional Application Ser. No. 61/008,855 by Micklem and Lorens, entitled METHODS FOR CREATING AND IDENTIFYING FUNCTIONAL RNA INTERFERENCE ELEMENTS, filed on Dec. 24, 2007. The prior applications are incorporated by reference for all purposes.

FIELD OF THE INVENTION

The invention relates to the field of genetics, and the control of gene expression. Specifically, the invention provides compositions and methods for the production and use of recombinant nucleic acid molecules that have the ability to specifically downregulate a target expressed gene in vivo.

BACKGROUND OF THE INVENTION

The development of novel pharmaceutical therapeutics relies on the identification and validation of key regulators of disease processes ("drug targets"). New technologies, reagents and methods that contribute to risk-reduction with respect to predicting therapeutic efficacy in human patients is highly valued. This process of therapeutic target identification and validation ideally utilizes functional therapeutic mimetic technologies in models of human disease. In particular, approaches that emulate therapeutic modalities, where a specific gene-product is inactivated and demonstrated to ameliorate a disease state, are needed.

RNA interference (RNAi) is a conserved cellular mechanism for regulating gene expression in all cells. RNAi-based technology has rapidly become a significant functional genomics tool and drug target validation approach for the pharmaceutical and biotechnology industries. RNAi technology facilitates the directed inactivation ("silencing") of virtually any gene and thus the opportunity to associate specific gene-function with specific disease mechanisms.

Contemporary approaches to constructing RNAi trigger molecules (i.e., an siRNA molecule) build on empirically determined bioinformatic algorithms. Significant progress has been made in understanding the molecular mechanisms underlying in vivo RNAi, and furthermore, artificial RNAi-inducing molecules have been successfully constructed. However, significant challenges remain in the development of this technology, particularly in the context of pharmaceutical target validation.

Various methods are known in the literature for siRNA vector and library construction. For example, Sen et al., "Restriction enzyme-generated siRNA (REGS) vectors and libraries," *Nature Genetics* 36(2): 183-189 (2004) describes a "REGS" method for producing siRNA molecules. However, the REGS method has various drawbacks. The REGS method described in that publication produces shRNA molecules that are shorter than the optimal length for inducing RNAi, and which therefore function inefficiently. Furthermore, the yield at each step of the procedure is low so that prior to cloning the product must be amplified. The method of amplification described (i.e., rolling circle amplification by phi29 polymerase) is prone to bias (the preferential amplification of one product at the expense of amplification of other products), thereby resulting in a library that contains only a fraction of the potential diversity.

There is a need in the art for improved methods for generating and screening for biologically active molecules that induce RNAi, for example, shRNA or siRNA molecules. There is a need in the art for improved methods for validating candidate drug targets and predicting in vivo responses to inhibitor compounds. Further, there is a need to develop methods that aid in the validation of candidate drug targets, where the validation of drug targets can be done in a dose-dependent manner. The present invention provides compositions and methods that meet this need, overcome the limitations of the REGS method, and provide other benefits that will become apparent upon reading the present disclosure.

SUMMARY OF THE INVENTION

The invention provides methods for generating hairpin DNA molecules that are "DNA effector intermediates" that encode the RNA molecules (e.g., siRNA molecules) that are RNAi effector molecule candidates. These DNA effector intermediates comprise a loop and a substantially double-stranded stem, where the double-stranded stem contains sequence derived from an mRNA molecule that that will be the target of the RNAi effector molecule. The methods consists of the steps:
(a) providing:
i) a double-stranded cDNA corresponding to the mRNA or a portion of the mRNA; and
ii) at least one hairpin-adapter oligonucleotide comprising a loop and a stem, the stem comprising a first restriction site that is recognized by a first endonuclease having a cleavage site at least 22 base pairs distant from the recognition site;
(b) fragmenting the cDNA to produce at least one cDNA fragment at least 22 base pairs in length;
(c) enzymatically ligating the first hairpin-adapter oligonucleotides to one or both termini of the cDNA fragment, to form an intermediate DNA molecule; and
(d) enzymatically digesting the intermediate DNA molecule with the restriction endonuclease, thereby producing the DNA effector intermediate having a stem comprising at least 22 nucleotide base pairs that correspond to a small interfering RNA (siRNA) that is specific for a target mRNA. Optionally, the ligation reaction mixture can be treated with at least one exonuclease, e.g., exonuclease I and/or λ exonuclease, prior to enzymatically digesting with the endonuclease.

In some embodiments, the at least one siRNA molecule encodes an RNAi trigger molecule that has specific inhibitory activity towards said mRNA and/or the siRNA molecule can be a plurality of siRNA molecules that encode RNAi trigger molecules that each have inhibitory activity towards the mRNA target. The RNAi trigger molecules produced by the methods of the invention are also a feature of the invention.

In some embodiments of the invention, a plurality of siRNA hairpin molecules are produced, for example, a library of siRNA hairpin molecules. The cDNA fragments that are used to produce the DNA effector intermediates can be at least 50 base pairs in length, or alternatively, at least 100 base pairs in length. In some aspects, the hairpin-adapter oligonucleotides are ligated to both ends of the cDNA fragment, and restriction digestion produces two hairpin DNA intermediate effector molecules. In some embodiments, the hairpin-adapter oligonucleotide is 5' dephosphorylated. In some embodiments, the hairpin-adapter oligonucleotides comprise terminal nucleotide sequences where a dimer comprising two enzymatically ligated first hairpin-adapter oligonucleotides generates a de novo restriction enzyme recognition site at the site of ligation.

In some embodiments of these methods, the endonuclease used to generate the DNA effector intermediates is selected from EcoP15I, McrBC, EcoP1 and PstII. The DNA effector intermediates can comprise at least 22 base pairs derived from and mRNA target, alternatively at least 25 base pairs, alternatively at least 30 base pairs, or alternatively, at least 35 base pairs. In some embodiments, the hairpin DNA molecule is blunt-ended and/or dephosphorylated.

The hairpin DNA effector intermediates produced by these protocols can be further processed in order to allow propagation and cellular expression. This processing can use either a "vector semi-attached" method or an "adapter oligo attached" method.

Using the vector semi-attached method, the additional steps include:

(e) providing a linearized vector adaptor and enzymatically ligating the vector adaptor and the dephosphorylated hairpin DNA molecule to produce a fusion nucleic acid comprising a stem-loop and a single-strand nick between the vector adaptor and the 5' terminus of the hairpin DNA molecule;

(f) providing a strand-displacing DNA polymerase and initiating single-strand polymerization of the hairpin DNA moiety by the DNA polymerase at the site of the single strand nick, thereby removing said loop secondary structure; and (g) enzymatically self-ligating the fusion nucleic acid, thereby producing a circularized vector comprising an shRNA template.

Using the "adapter oligo attached" method, the additional steps include:

(e) providing (i) a first enzymatically extendable primer, (ii) a double-stranded linear polynucleotide oligomer adaptor comprising a first nucleotide sequence complementary or partially complementary to the first primer, and (iii) a strand-displacing DNA polymerase;

(f) enzymatically ligating the oligomer adaptor and the hairpin DNA molecule to produce a fusion nucleic acid, optionally where the hairpin DNA molecule is treated with a DNA phosphatase prior to step (f);

(g) annealing the first primer to the fusion nucleic acid and enzymatically extending the primer by the strand-displacing DNA polymerase, thereby producing a linear siRNA template; and (h) cloning the linear siRNA template into a vector.

This method can also optionally include providing a second enzymatically extendable primer different from the first primer, and where the double-stranded linear polynucleotide oligomer adaptor comprises a second nucleotide sequence complementary or partially complementary to the second primer, wherein the method further comprises amplifying the linear siRNA template of step (g), the amplifying comprising annealing the second primer to the fusion nucleic acid and enzymatically extending the second primer by the strand-displacing DNA polymerase, thereby amplifying the linear siRNA template.

The invention also provides hairpin oligo adapters finding use in the generation of RNAi trigger molecules, where the oligo comprises a loop and a substantially double-stranded stem, said stem comprising a first endonuclease recognition site that is recognized by a first endonuclease, such as EcoP15I and McrBC, characterized by a cleavage activity at least 22 base pairs distant from the recognition site. This oligo can be enzymatically ligated to a double-stranded polynucleotide at least 22 base pairs in length derived from an mRNA molecule that is a target for a small interfering RNA (siRNA) molecule or a candidate siRNA molecule.

In some embodiments, the double-stranded polynucleotide that is at least 22 base pairs in length encodes an RNAi trigger molecule that has specific inhibitory activity towards the mRNA target. This double-stranded polynucleotide that is at least 22 base pairs in length can be a collection of such molecules, where each encoded RNAi trigger molecule has specific inhibitory activity towards the mRNA target, and the collection of molecules can optionally form a epi-allelic series of hypomorphic shRNA molecules.

The hairpin adapter oligo can further comprises a second endonuclease recognition site that is recognized by a second endonuclease that is different than the first endonuclease. In some embodiments, the hairpin adapter oligo lacks a 5'-terminal phosphate. In some embodiments, the hairpin-adapter oligo comprises terminal nucleotide sequences where a dimer comprising two enzymatically ligated hairpin-adapter oligonucleotides generates a de novo restriction enzyme recognition site at the site of ligation. A hairpin-adapter oligo of the invention can comprise at least one lac operator recognition site (lacO). A hairpin-adapter oligo of the invention can encode a reporter polypeptide.

In other embodiments, the invention provides methods for testing the specific inhibitory activity of an RNAi trigger molecule for a polynucleotide target. These methods comprise the steps of:

(a) providing a cell comprising:
  i) a reporter construct comprising a reporter transcription unit, typically driven by a suitable promoter, where the reporter transcription unit comprising (A) a translatable reporter gene polynucleotide encoding a reporter polypeptide, and (B) a nontranslatable target polynucleotide or a portion thereof, the target polynucleotide positioned 3' to the reporter gene polynucleotide; and
  ii) a vector encoding an RNAi trigger molecule (for example, any suitable vector including a retroviral vector, a lentiviral vector, an adenoviral vector, or any suitable eukaryotic expression vector);

(b) culturing the first cell under conditions that permit expression of the reporter transcription unit and the RNAi trigger molecule;

(c) detecting a signal associated with the cell (for example, by fluorescence activated cell sorting (FACS) or by magnetic flow cell sorting), where the signal corresponds to a level of expression of the reporter polypeptide in the cell; and (d) correlating the detected signal with the specific inhibitory activity of the RNAi trigger molecule for the target polynucleotide, thereby testing for the presence or absence of the specific inhibitory activity of the RNAi trigger molecule for the polynucleotide target.

In this method, the target polynucleotide can be a cDNA, corresponding to an mRNA or any portion of an mRNA. The nature of the RNAi trigger molecule is not limited, and can be a double-stranded RNA, a short hairpin RNA (shRNA), a micro RNA (miRNA), a shmiRNA or a small interfering RNA (siRNA). In these methods, the reporter gene is typically a fusion reporter polypeptide, for example, a fusion polypeptide comprising a PEST motif. In some embodiments, these RNAi activity assay methods can be conducted with single-cell resolution. In these methods, the reporter gene can encode a fluorescent reporter polypeptide, for example, a green fluorescent protein, a red fluorescent protein, a yellow fluorescent protein or a blue fluorescent protein. In other embodiments, the reporter gene encodes a cell surface marker, such as a Lyt2 cell surface marker. In still other embodiments, the reporter can be a luciferase polypeptide, a β-galactosidase, α-lactamase, an alkaline phosphatase or a horse-radish peroxidase. Alternatively still, the reporter gene encodes a negative selection marker, such as thymidine kinase (tk), HRPT or APRT.

As a modification of the protocol described above, the invention also provides methods for screening RNAi trigger molecule libraries in order to identify RNAi trigger molecules having specific inhibitory activity for a particular mRNA target. These methods comprise the steps:
  (a) providing:
    i) a library comprising a plurality of vector members, where the vector members encode a plurality of RNAi trigger molecules;
    ii) a reporter construct comprising a reporter transcription unit comprising (A) a translatable reporter gene polynucleotide encoding a reporter polypeptide, and (B) a nontranslatable cDNA corresponding to an mRNA target polynucleotide or a portion thereof, where the target polynucleotide is positioned 3' to the reporter gene polynucleotide;
    iii) a plurality of cells, each cell comprising a library member and a reporter construct;
  (b) culturing the plurality of cells under conditions that permit expression of the reporter transcription unit and the RNAi trigger molecule;
  (c) detecting a signal associated with each cell in the plurality of cells, the signal corresponding to a level of expression of the reporter polypeptide in the cell; and
  (d) identifying cells that show absent or reduced signal relative to any other cell in the plurality of cells, thereby identifying an active RNAi trigger molecule from the library of RNAi trigger molecules, where the active RNAi trigger molecule has specific inhibitory activity for the mRNA target.

In still other embodiments, the invention provides methods for identifying the polynucleotide target of a known RNAi trigger molecule. The methods identify a polynucleotide from a plurality of candidate target polynucleotides (e.g., from a library of candidate molecules) that is specifically targeted by an RNAi trigger molecule. These methods comprise the steps:
  (a) providing:
    i) an RNAi trigger molecule (typically expressed from a larger vector);
    ii) a reporter construct library comprising a plurality of reporter construct members, each member comprising a reporter transcription unit comprising (A) a translatable reporter gene polynucleotide encoding a reporter polypeptide, and (B) a nontranslatable candidate target polynucleotide, where the candidate target polynucleotide is positioned 3' to the reporter gene polynucleotide, where the reporter construct library comprises a plurality of candidate target polynucleotides (typically corresponding to mRNA molecules or portions of mRNA molecules);
    iii) a plurality of cells, each cell comprising an RNAi trigger molecule and a reporter construct library member;
  (b) culturing the plurality of cells under conditions that permit expression of the reporter transcription unit;
  (c) detecting a signal associated with each cell in the plurality of cells, said signal corresponding to a level of expression of the reporter polypeptide in the cell; and
  (d) identifying cells that show absent or reduced signal relative to any other cell in the plurality of cells, thereby identifying a polynucleotide that is specifically targeted by the RNAi trigger molecule.

In other aspects, the polynucleotide sequences identified herein that have RNAi trigger molecule activity are also a feature of the invention. For example, a polynucleotide sequence selected from SEQ ID NO: 1-15, and active variants of those sequences are a feature of the invention.

DEFINITIONS

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. For example, reference to "a nucleic acid," also includes a plurality of that nucleic acid molecule.

Unless defined otherwise, all technical and scientific terms used herein have the same meaning as commonly understood by one of ordinary skill in the art to which the invention pertains. In describing and claiming the present invention, the following terminology will be used in accordance with the definitions set out below.

As used herein, the term "base" refers to any nitrogen-containing heterocyclic moiety capable of forming Watson-Crick type hydrogen bonds in pairing with a complementary base or base analog. A large number of natural and synthetic (non-natural, or unnatural) bases, base analogs and base derivatives are known. Examples of bases include purines, pyrimidines, and modified forms thereof. The naturally occurring bases include, but are not limited to, adenine (A), guanine (G), cytosine (C), uracil (U) and thymine (T). As used herein, it is not intended that the invention be limited to naturally occurring bases, as a large number of unnatural (non-naturally occurring) bases and their respective unnatural nucleotides that find use with the invention are known to one of skill in the art. Examples of such unnatural bases are given below.

The term "nucleoside" refers to a compound consisting of a base linked to the C-1' carbon of a sugar, for example, ribose or deoxyribose.

The term "nucleotide" refers to a phosphate ester of a nucleoside, as a monomer unit or within a polynucleotide. "Nucleotide 5'-triphosphate" refers to a nucleotide with a triphosphate ester group attached to the sugar 5'-carbon position, and are sometimes denoted as "NTP", or "dNTP" and "ddNTP." A modified nucleotide is any nucleotide (e.g., ATP, TTP, GTP or CTP) that has been chemically modified, typically by modification of the base moiety. Modified nucleotides include, for example but not limited to, methylcytosine, 6-mercaptopurine, 5-fluorouracil, 5-iodo-2'-deoxyuridine and 6-thioguanine. As used herein, the term "nucleotide analog" refers to any nucleotide that is non-naturally occurring.

The terms "polynucleotide," "nucleic acid," "oligonucleotide," "oligomer," "oligo" or equivalent terms, as used herein refer to a polymeric arrangement of monomers that can be corresponded to a sequence of nucleotide bases, e.g., a DNA, RNA, peptide nucleic acid, or the like. A polynucleotide can be single- or double-stranded, and can be complementary to the sense or antisense strand of a gene sequence. A polynucleotide can hybridize with a complementary portion of a target polynucleotide to form a duplex, which can be a homoduplex or a heteroduplex. The length of a polynucleotide is not limited in any respect.

Linkages between nucleotides can be internucleotide-type phosphodiester linkages, or any other type of linkage, or combination of linkages. A polynucleotide can be composed entirely of a single type of monomeric subunit and one type of linkage, or can be composed of mixtures or combinations of different types of subunits and different types of linkages (a polynucleotide can be a chimeric molecule). As used herein, a polynucleotide analog retains the essential nature of natural polynucleotides in that they hybridize to a single-stranded nucleic acid target in a manner similar to naturally occurring polynucleotides.

A "polynucleotide sequence" refers to the sequence of nucleotide monomers along the polymer. A "polynucleotide" is not limited to any particular length or range of nucleotide sequence, as the term "polynucleotide" encompasses polymeric forms of nucleotides of any length. A polynucleotide can be produced by biological means (e.g., enzymatically), or synthesized using an enzyme-free system. A polynucleotide can be enzymatically extendable or enzymatically non-extendable. In some cases, the polynucleotide is referred to as a "DNA" or a "DNA molecule."

Polynucleotides that are formed by 3'-5' phosphodiester linkages are said to have 5'-ends and 3'-ends because the nucleotide monomers that are reacted to make the polynucleotide are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right. Enzymatically produced or artificially synthesized polynucleotides can be modified where the molecule lacks the 5' phosphate group or the 3' hydroxyl group.

As used herein, it is not intended that the term "polynucleotides" be limited to naturally occurring polynucleotides sequences or polynucleotide structures, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention. Non-limiting examples of such unnatural structures include non-ribose sugar backbones, 3'-5' and 2'-5' phosphodiester linkages, internucleotide inverted linkages (e.g., 3'-3' and 5'-5'), and branched structures. Furthermore, unnatural structures also include unnatural internucleotide analogs, e.g., peptide nucleic acids (PNAs), locked nucleic acids (LNAs), $C_1$-$C_4$ alkylphosphonate linkages such as methylphosphonate, phosphoramidate, $C_1$-$C_6$ alkyl-phosphotriester, phosphorothioate and phosphorodithioate internucleotide linkages.

As used herein, the term "sequence of a polynucleotide," "nucleic acid sequence," "nucleotide sequence," "polynucleotide sequence", and equivalent or similar phrases refer to the order of nucleotides in the polynucleotide. In some cases, a "sequence" refers more specifically to the order and identity of the bases that are each attached to the nucleotides. A sequence is typically read (written) in the 5' to 3' direction. Unless otherwise indicated, a particular polynucleotide sequence of the invention optionally encompasses complementary sequences, in addition to the sequence explicitly indicated.

As used herein, the terms "amplification," "amplifying" and the like refer generally to any process that results in an increase in the copy number of a molecule or set of related molecules. As it applies to polynucleotide molecules, amplification means the production of multiple copies of a polynucleotide molecule, or a portion of a polynucleotide molecule, typically starting from a small amount of a polynucleotide. Amplification of polynucleotides encompasses a variety of chemical and enzymatic processes. The generation of multiple DNA copies from one or a few copies of a template DNA molecule during a polymerase chain reaction (PCR), a strand displacement amplification (SDA) reaction, a transcription mediated amplification (TMA) reaction, a nucleic acid sequence-based amplification (NASBA) reaction, or a ligase chain reaction (LCR) are forms of amplification. Amplification is not limited to the strict duplication of the starting molecule. For example, the generation of multiple cDNA molecules from a limited amount of mRNA in a sample using RT-PCR is a form of amplification. Furthermore, the generation of multiple RNA molecules from a single DNA molecule during the process of transcription is also a form of amplification. Cloning is also a form of amplification, where preferential expansion of the host cell population increases the amount of the cloned DNA. In some embodiments, amplification is optionally followed by additional steps, which can include, but not limited to, labeling, sequencing, purification, isolation, hybridization, size resolution, expression, detecting and/or cloning.

As used herein, the term "polymerase chain reaction" (PCR) refers to a method for amplification that is well known in the art for increasing the concentration of a segment of a target polynucleotide in a sample, where the sample can be a single polynucleotide species, or multiple polynucleotides. Generally, the PCR process consists of introducing a molar excess of one, two or more extendable oligonucleotide primers to a reaction mixture comprising the desired target sequence(s), where the primers are complementary to opposite strands of the double stranded target sequence. The reaction mixture is typically subjected to a program of thermal cycling in the presence of a DNA polymerase, resulting in the amplification of the desired target sequence flanked by the DNA primers. Reverse transcriptase PCR (RT-PCR) is a PCR reaction that uses RNA template and a reverse transcriptase, or an enzyme having reverse transcriptase activity, to first generate a single stranded DNA molecule prior to the multiple cycles of DNA-dependent DNA polymerase primer elongation. Methods for a wide variety of PCR applications are widely known in the art, and described in many sources, for example, *Current Protocols in Molecular Biology*, Ausubel et al., eds., *Current Protocols*, a joint venture between Greene Publishing Associates, Inc. and John Wiley & Sons, Inc., (supplemented through 2006) and Sambrook et al., Molecular Cloning—A Laboratory Manual (3rd Ed.), Vol. 1-3, Cold Spring Harbor Laboratory, Cold Spring Harbor, N.Y., 2001.

As used herein, the term "DNA-dependent DNA polymerase" refers to a DNA polymerase enzyme that uses deoxyribonucleic acid (DNA) as a template for the synthesis of a complementary and antiparallel DNA strand. Thermostable DNA-dependent DNA polymerases find use in PCR amplification reactions. Suitable reaction conditions (and reaction buffers) for DNA-dependent DNA polymerase enzymes, and indeed any polymerase enzyme, are widely known in the art, and are described in numerous sources.

As used herein, the term "DNA-dependent RNA polymerase" refers to an RNA polymerase enzyme that uses deoxyribonucleic acid (DNA) as a template for the synthesis of an RNA strand. The process mediated by a DNA-dependent RNA polymerase is commonly referred to as "transcription."

As used herein, the term "RNA-dependent DNA polymerase" refers to a DNA polymerase enzyme that uses ribonucleic acid (RNA) as a template for the synthesis of a complementary and antiparallel DNA strand. The process of generating a DNA copy of an RNA molecule is commonly termed "reverse transcription," or "RT," and the enzyme that accomplishes that is a "reverse transcriptase." Some naturally-occurring and mutated DNA polymerases also possess reverse transcription activity.

As used herein, the term "primer" refers to an enzymatically extendable oligonucleotide that generally comprises a defined sequence that is designed to hybridize in an antiparallel manner with a complementary, primer-specific portion of a target sequence. A primer can initiate the polymerization of nucleotides in a template-dependent manner to yield a polynucleotide that is complementary to the target polynucleotide. A primer nucleic acid does not need to have 100% complementarity with its template subsequence for primer elongation to occur; primers with less than 100% complementarity can be sufficient for hybridization and polymerase elongation to occur. Primer extension and polymerization reaction conditions and reagents are well established in the art, and are described in a variety of sources.

As used herein, the expression "amplification primer" refers to a primer that is generally in molar excess relative to its target polynucleotide sequence, and primes template-dependent enzymatic DNA synthesis and amplification of the target sequence (and sequence downstream from the site of hybridization) to yield a single-stranded amplicon. As used herein, the expression "amplification primer pair" refers to a set of two primers that are generally in molar excess relative to their target polynucleotide sequence, and together prime template-dependent enzymatic DNA synthesis and amplification of the target sequence to yield a double-stranded amplicon. As used herein, the term "amplicon" refers to a polynucleotide molecule (or collectively the plurality of molecules) produced following the amplification of a particular target nucleic acid. The amplification method used to generate the amplicon can be any suitable method, most typically, for example, by using a PCR methodology. An amplicon is typically, but not exclusively, a DNA amplicon. An amplicon can be single-stranded or double-stranded, or in a mixture thereof in any concentration ratio.

As used herein, the terms "hybridization" and "annealing" and the like are used interchangeably and refer to the base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotide molecules is typically base specific, e.g., A/T and G/C, by Watson/Crick and/or Hoogsteen-type hydrogen bonding. It is not a requirement that two polynucleotides have 100% complementarity over their full length to achieve hybridization. In some aspects, a hybridization complex can form from intermolecular interactions. In other aspects, a hybridization complex can form from intramolecular interactions, resulting in the formation of structures such as hairpin nucleic acid molecules. A hairpin nucleic acid molecule can contain a single-stranded loop domain and a double-stranded stem domain.

As used herein, the terms "complementary" or "complementarity" are used in reference to antiparallel strands of polynucleotides related by the Watson-Crick and Hoogsteen-type base-pairing rules. For example, the sequence 5'-AGTTC-3' is complementary to the sequence 5'-GAACT-3'. The terms "completely complementary" or "100% complementary" and the like refer to complementary sequences that have perfect Watson-Crick pairing of bases between the antiparallel strands (no mismatches in the polynucleotide duplex). However, complementarity need not be perfect; stable duplexes, for example, can contain mismatched base pairs or unmatched bases. The terms "partial complementarity," "partially complementary," "incomplete complementarity" or "incompletely complementary" and the like refer to any alignment of bases between antiparallel polynucleotide strands that is less than 100% perfect (e.g., there exists at least one mismatch or unmatched base in the polynucleotide duplex). For example, the alignment of bases between the antiparallel polynucleotide strands can be at least 99%, 95%, 90%, 85%, 80%, 75%, 70%, 65%, 60%, 55%, or 50%, or any value between.

Furthermore, a "complement" of a target polynucleotide refers to a polynucleotide that can hybridize in an antiparallel association with at least a portion of the target polynucleotide. The antiparallel association can be intramolecular, e.g., in the form of a hairpin loop within a nucleic acid molecule, or intermolecular, such as when two or more single-stranded nucleic acid molecules hybridize with one another.

As used herein, "target", "target polynucleotide", "target sequence," "target gene" and the like refer, in one aspect, to a specific polynucleotide sequence that is subjected to degradation and/or downregulation by the process of RNAi that is induced by a particular RNAi trigger molecule. That is to day, the down regulated polynucleotide is a target sequence for the RNAi trigger molecule. In other aspects, term "target" more generally refers to a polynucleotide that is the subject of hybridization with a complementary polynucleotide, e.g., a labelled probe or a DNA polymerase primer. The hybridization complex formed as a result of the annealing of a polynucleotide with its target is termed a "target hybridization complex." The structure of the target sequence is not limited, and can be composed of DNA, RNA, analogs thereof, or combinations thereof, and can be single-stranded or double-stranded.

As used herein, the terms "label" or "reporter," in their broadest sense, refer to any moiety or property that is detectable, or allows the detection of, that which is associated with it. For example, a reporter protein can be expressed in a cell (and reside in the intracellular space), thereby permitting detection of the cell that expresses the reporter. In other aspects, a label or reporter can be attached (covalently or non-covalently) to the cell surface, for example, in the case where a labelled antibody specifically binds to a protein expressed on the cell surface. In various aspects, a label can, alternatively or in combination: (i) provide a detectable signal; (ii) interact with a second label to modify the detectable signal provided by the second label; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior.

In some aspects, the detection of the label or reporter correlates with the presence or absence of some other molecule, property or biological activity, or can be used to identify, select and/or screen targets in a system of interest. The choice of the most suitable reporter to use for a particular application depends on the intended use, and other variables known to one familiar with the art. In some aspects, a reporter is a reporter gene.

Labels and reporters vary widely in their structures and their mechanisms of action. Examples of labels include, but are not limited to, fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes that are negatively charged, such as dyes of the fluorescein family and Alexa family of dyes (Invitrogen), or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), and Texas Red is commercially available from, e.g., Molecular Probes, Inc. (Eugene, Oreg.). Dyes of the cyanine family include, e.g., Cy2, Cy3, Cy5, Cy 5.5 and Cy7, and are commercially available from, e.g., Amersham Biosciences Corp. (Piscataway, N.J., USA). Quantum Dots (Invitrogen), which fluoresce from the quantum properties of the semiconductor nanocrystals from which they are made from, are also useful labels.

A wide variety of reporter molecules and genes are known in the art. Each reporter has a particular assay for the detection of that reporter. Some reporter detection assays can be enzymatic assays, while other assays can be immunological in nature (e.g., ELISA or immunohistochemical analysis), or colorimetric, for example. Further still, a reporter can include a protein, e.g., an enzyme, that confers antibiotic resistance or sensitivity (e.g., β-lactamase, chloramphenicol acetyltransferase (CAT), and the like), a fluorescent marker (e.g., a fluorescent protein such as GFP (green fluorescent protein), YFP (yellow fluorescent protein), EGFP (enhanced GFP), RFP (red fluorescent protein), etc.), a luminescent marker (e.g., a firefly luciferase protein), an affinity based screening marker, an enzymatic activity such as lacZ (β-galactosidase), or other positive or negative selectable marker genes such as ADH (alcohol dehydrogenase), his3, ura3, leu2, lys2, or the like.

As used herein, the expression "derived from" refers to a component that is isolated from or made using a specified sample, molecule, organism or information from the specified molecule or organism. For example, a cDNA nucleic acid molecule is derived from an mRNA.

As used herein, the expression "corresponding to" broadly refers to one item that is related to, derived from, the product of, homologous to, generated by, or in any way related to another item. For example, in the case of nucleic acid molecules, a cDNA or siRNA can correspond to an mRNA, or a portion of an mRNA. In other aspects, a signal can correspond to the expression of a particular reporter in a sample or cell.

As used herein, the terms "subsequence," "fragment" or "portion" and the like refer to any portion of a larger sequence (e.g., a polynucleotide or polypeptide sequence), up to and including the complete sequence. The minimum length of a subsequence is generally not limited, except that a minimum length may be useful in view of its intended function. For example, a fragment of a cDNA finds use in the construction of hairpin DNA molecules of the invention as intermediate structures for the production of siRNA molecules. In some aspects, these cDNA fragments can be, for example but not limited to, at least 22 base pairs in length, at least 50 base pairs in length, or at least 100 base pairs in length.

As used herein, the term "kit" is used in reference to a combination of articles that facilitate a process, method, assay, analysis or manipulation of a sample. Kits can contain written instructions describing how to use the kit (e.g., instructions describing the methods of the present invention), chemical reagents or enzymes required for the method, primers and probes, other nucleic acids, as well as any other components. For example, in some embodiments, the present invention provides kits comprising hairpin adapter oligonucleotides of the invention, kits for generating nucleic acids that produce siRNA molecules, kits for identifying biologically active siRNA molecules, and kits for identifying siRNA targets. These kits can include, for example but not limited to, reagents for mRNA library construction and manipulation, endonucleases such as restriction enzymes, reagents for the collection and purification of recombinant DNA molecules, vectors for expressing a suitable reporter gene, vectors that express RNAi trigger molecules, vectors suitable for copy-number amplification, and vectors suitable for gene expression in a desired host cell.

As used herein, a "polypeptide" is any oligomer of amino acids (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acids. As used herein, the term "protein" is synonymous with polypeptide. The term "peptide" typically refers to a small polypeptide, for example but not limited to, from 2-25 amino acids in length.

As used herein, the term "gene" most generally refers to a combination of polynucleotide elements, that when operatively linked in either a native or recombinant manner, provide some product or function. The term "gene" is to be interpreted broadly, and can encompass mRNA, cDNA, cRNA and genomic DNA forms of a gene. In some cases, genes comprise coding sequences (e.g., an "open reading frame" or "coding region") necessary for the production of a polypeptide, while in other aspects, genes do not encode a polypeptide. Examples of genes that do not encode polypeptides include ribosomal RNA genes (rRNA), transfer RNA (tRNA) genes and micro RNA genes (miRNA).

Generally, the term "gene" encompasses the transcribed sequences, including 5' and 3' untranslated sequences (or 5' UTR and 3' UTR), exons, introns, regulatory sequences located within these domains, and the associated non-transcribed regions including upstream and downstream regulatory regions, enhancers and promoters. In some genes, within the transcribed region are "open reading frames" that code for polypeptides. The term "gene" encompasses mRNA, cDNA and genomic forms of a gene.

In some aspects, the genomic form or genomic clone of a gene includes the sequences of the transcribed mRNA, as well as other non-transcribed sequences which lie outside of the transcript. The regulatory regions that lie outside the mRNA transcription unit are sometimes called "5' or 3' flanking sequences." A functional genomic form of a gene typically contains regulatory elements necessary for the regulation of transcription. For example, the term "promoter" is usually used to describe a DNA region, typically but not exclusively 5' of the site of transcription initiation, sufficient to confer accurate transcription initiation. In some embodiments, a promoter is constitutively active, while in alternative embodiments, the promoter is conditionally active (e.g., where transcription is initiated only under certain physiological conditions). Generally, the term "regulatory element" refers to any genetic element that controls some aspect of the expression of nucleic acid sequences.

As used herein, the expressions "in operable combination," "in operable order," "operatively linked," "operatively joined" and similar phrases, when used in reference to nucleic acids, refer to the operational linkage of nucleic acid sequences placed in functional relationships with each other. For example, an operatively linked promoter, enhancer, open reading frame and terminator sequence results in the accurate production of an RNA molecule. In some aspects, operatively linked nucleic acid elements result in the transcription of an open reading frame and ultimately the production of a polypeptide (i.e., expression of the open reading frame).

As used herein, the terms "vector", "vehicle", and "construct" are used in reference to any polynucleotide molecule that can be propagated and used to transfer nucleic acid segment(s). A vector optionally comprises parts that mediate vector propagation and manipulation (e.g., sequences necessary for replication, genes imparting drug or antibiotic resistance, a multiple cloning site, operably linked promoter/enhancer elements which enable the expression of a cloned gene, etc.). For example, a "cloning vector" or "shuttle vector" or "subcloning vector" contains operably linked parts that facilitate subcloning steps (e.g., a multiple cloning site containing multiple restriction endonuclease sites). Vectors are often derived from plasmids, bacteriophages, or plant or animal viruses.

As used herein, the term "expression vector" refers to a recombinant vector comprising operably linked polynucleotide elements that facilitate expression of a desired gene (e.g., a gene that encodes a protein or an RNAi trigger molecule) in a particular host organism (e.g., a bacterial expression vector or eukaryotic expression vector). Polynucleotide sequences that facilitate gene expression can include, e.g., promoters, enhancers, transcription termination sequences, and ribosome binding sites, often along with other sequences.

As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

As used herein, the terms "heterologous" or "exogenous" as applied to polynucleotides or polypeptides refers to molecules that have been rearranged or artificially supplied to a biological system and are not in a native configuration (e.g., with respect to sequence, genomic position or arrangement of parts) or are not native to that particular biological system. The terms indicate that the relevant material originated from a source other than the naturally occurring source, or refers to molecules having a non-natural configuration, genetic location or arrangement of parts. The terms "exogenous" and "heterologous" are sometimes used interchangeably with "recombinant."

As used herein, the term "recombinant" in reference to a nucleic acid or polypeptide indicates that the material (e.g., a recombinant nucleic acid, gene, polynucleotide, polypeptide, etc.) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural context and cloned into any type of artificial nucleic acid vector. Protocols and reagents to produce recombinant molecules, especially recombinant nucleic acids, are common and routine in the art. See, for example, *Current Protocols in Molecular Biology*, Ausubel et al., eds., *Current Protocols*, a joint venture between Greene Publishing Associates, Inc. and John Wiley & Sons, Inc., (supplemented through 2006) and Sambrook et al., Molecular Cloning—A Laboratory Manual (3rd Ed.), Vol. 1-3, Cold Spring Harbor Laboratory, Cold Spring Harbor, N.Y., 2001.

In contrast to a heterologous or exogenous molecule, a "native" or "endogenous" molecule can be found in a naturally occurring biological system, cell, tissue, species or chromosome under study. A "native" or "endogenous" gene is a gene that generally does not contain nucleic acid elements encoded by sources other than the source on which it normally resides in nature (e.g., a nuclear chromosome, mitochondrial or chloroplast genome or naturally occurring plasmids). An endogenous gene, transcript or polypeptide is encoded by its natural locus, and is not artificially supplied to the cell.

As used herein, the term "host cell" refers to a cell that contains a heterologous nucleic acid, such as a vector, and supports the replication and/or expression of the nucleic acid. Host cells can be prokaryotic cells such as *E. coli*, or eukaryotic cells such as mammalian cells (e.g., mouse cells).

As used herein, the term "RNAi" refers to a process by which a double-stranded RNA molecule can lead to a reduction in the expression of a gene or genes, where the RNA molecule contains nucleotide sequences similar or identical to nucleotide sequences in the affected gene or genes. The reduction in expression can occur mainly through degradation of the mRNA, but inhibition of translation can also occur Inhibition of transcription can also play a role in gene down-regulation.

At the level of transcript degradation/translation inhibition, the active biological component is a short (approx 21 nucleotide) single-stranded RNA hybridized to its complementary (or near complementary) target mRNA in the context of a RISC complex. Some naturally occurring 21 nucleotide strands are known as microRNAs (or miRNA). This single short strand of RNA is derived from a short double-stranded RNA (usually with two nucleotide single-stranded ends). The short double stranded RNA is bound by the RISC complex before one of the two strands is discarded. These short double-stranded RNA molecules are called siRNA, and can be from natural sources, artificial or recombinant.

As used herein, the term siRNA can refer to siRNA molecules that are produced in vitro, and then introduced into a cell. In some aspects, as used herein, an siRNA molecule is not limited to naturally occurring nucleotides, and can incorporate any one or plurality of unnatural structures or chemical modifications, generally where the use of such unnatural structures or modifications result in an siRNA molecule with improved activity or stability. As used herein, an siRNA molecule can also be produced in a cell by the action of the enzyme Dicer on longer dsRNA molecules or hairpin-shaped dsRNA molecules. Longer dsRNA molecules can be provided experimentally (i.e., artificially) or can occur naturally (e.g., by infection with dsRNA viruses). As used herein, the hairpin-shaped dsRNA molecules are called "shRNA" or "pre-miRNA."

Hairpin shRNA molecules can occur naturally in the production of miRNA from primary transcripts (pri-miRNA). In this case they are also known as pre-miRNA. Like siRNA, shRNA molecules can also be directly introduced into a cell after production in vitro. They can also be artificially/recombinantly produced within a cell, e.g., expressed from a suitable expression vector.

Pre-miRNA shRNAs can be naturally produced from primary miRNA transcripts (pri-miRNA) by the action of the enzymes Drosha and Pasha which recognize and release regions of the primary miRNA transcript which form a stem-loop structure. Alternatively, the pri-miRNA transcript can be engineered to replace the natural stem-loop structure with an artificial/recombinant stem-loop structure. In this case Drosha and Pasha recognize and release the artificial shRNA. This approach is known as shmiRNA or microRNA framework shRNA. Cassettes that produce shRNAs can be cloned into shmiRNA vectors, in which case they produce shRNA via a pri-miRNA-like precursor.

As used herein, the term siRNA can refer to an siRNA molecule produced by generating a suitable artificial/recombinant shRNA within a cell, for example, from an expression vector. The shRNA can be produced either directly (e.g., by expression driven by a U6 promoter) or from a longer pri-miRNA-like transcript. In either case, generation of the siRNA relies on the internal machinery of the cell to correctly process the RNA into siRNA, incorporate it into RISC and trigger RNAi.

As used herein, the expression "RNAi trigger molecule" refers to any DNA molecule, RNA molecule, or hybrid DNA/RNA molecule, natural or artificial, that induces RNA interference. In some aspects, an RNAi trigger molecule is subject to intracellular processing and incorporation into a RISC complex in order to effect the induction of RNA interference. Although such a molecular mechanism is widely proposed in the literature, an understanding of the mechanism is not required to make or use the invention. As used herein, RNAi trigger molecules can include, for example but not limited to, pri-miRNA, shmiRNA, shRNA and siRNA molecules. The following diagram illustrates these molecular pathways in the activation of RNAi.

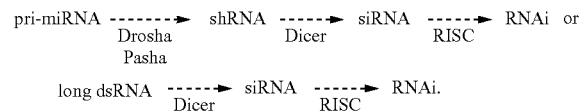

As used herein, the expressions "candidate siRNA molecule" or "candidate RNAi trigger molecule" or "candidate shRNA molecule" or the like refer to any DNA molecule, RNA molecule, or hybrid DNA/RNA molecule, natural or artificial, that may induce RNA interference. In some aspects, a candidate siRNA trigger molecule can be a member of a library of candidate siRNA molecules. In some aspects as used herein, a candidate siRNA trigger molecule can be tested for RNAi activity. In other aspects, as used herein, a population of candidate siRNA molecules are screened for RNAi activity.

As used herein, the expressions "enzymatically ligating" or "enzymatically ligated" refer to the process of covalently joining two or more nucleic molecules (typically DNA molecules) by an enzymatic process such as by using a known DNA ligase. Suitable ligase enzymes are well known in the art. An enzymatic ligation process is in contrast to a synthetic ligation process that uses chemical reactive moieties in the absence of protein enzymes.

As used herein, the expression "enzymatically digesting with endonuclease" refers to the process of cleaving a nucleic acid molecule using any known DNA cleaving endonuclease enzyme, where the endonuclease cleaves the phosphodiester bond within a polynucleotide chain. The choice of the particular endonuclease used depends on the application and the desire effect. For example, some endonucleases cleave nucleic acids in a non-sequence specific manner. Other endonucleases termed restriction endonucleases (restriction enzymes) cleave DNA in a sequence specific manner. Restriction endonucleases are generally divided into three categories, Type I, Type II, and Type III, according to their mechanism of action. Some restriction endonucleases cleave nucleic acids in a sequence specific manner at the site of the recognition sequence. Other restriction endonucleases cleave the nucleic acid molecule at a site some distance away from the recognition sequence.

As used herein, the expression "hairpin nucleic acid molecule" and any other equivalent expression generally refers to a nucleic acid molecule that is able to form a substantially double-stranded intramolecular stem domain and a resulting loop.

As used herein, the expression "substantially double stranded" refers to a double stranded nucleic acid molecule, any portion of a larger double stranded nucleic acid molecule or an intramolecular double stranded domain where there exists sufficient antiparallel complementarity to promote Watson-Crick type base-pairing. The complementarity between the single strands on the complex does not need to be 100% absolute, as less-than-perfect complementary antiparallel sequences are also able to form double stranded structures.

As used herein, the expression "strand-displacing polymerase" refers to a nucleic acid polymerase that is able to produce a single strand complement of a polynucleotide template, where that template is in a double-stranded complex with a complementary strand. Strand-displacing polymerases will typically initiate polymerization at the site of an internal nick or from an annealed primer. If a strand-displacing polymerase encounters a double-stranded region, it displaces the bound strand while transcribing the original strand. This contrasts with non-strand-displacing polymerases which will either simply stop or progressively degrade the DNA strand that is in the way (via 5'-3' exonuclease activity). The latter is called "nick translation" and applies e.g. to Taq DNA polymerase and E. coli DNA polymerase I. Strand displacing polymerases, in particular those that find use with the invention, are typically DNA-dependent DNA polymerases. Examples of strand-displacing polymerases include, for example, phi29 polymerase (Φ29), E. coli DNA polymerase I Klenow fragment, Vent DNA polymerase, 9° $N_m$ DNA polymerase (New England Biolabs) and Bst DNA polymerase large fragment.

As used herein, the expression "reporter transcription unit" refers to a transcript that encodes a polypeptide reporter. A reporter transcription unit can optionally contain other elements in addition to an open reading frame that encodes a reporter polypeptide.

As used herein, the expression "translatable polynucleotide" refers to any nucleotide sequence that is capable of being translated in order to generate a polypeptide.

As used herein, the term "non-translatable polynucleotide" refers to any nucleotide sequence that is unable to be translated, or fully translated, and thus does not generate a polypeptide product. For example, a non-translatable polynucleotide can contain a stop codon at its 5' end, thereby preventing translation. Alternatively, a stop codon can be placed anywhere in the open reading frame, thereby producing a truncated polypeptide product that is likely to be unstable in vivo. A polynucleotide can also be rendered non-translatable by other means, including but not limited to absence of an initiating codon, incorrect initiation context or the absence of an open reading frame (ORF).

As used herein, the expression "specific inhibitory activity" refers to the inhibitory activity of a molecule (e.g., an RNAi trigger molecule) that preferentially affects one target relative to another target or a pool of other targets. As used herein, an RNAi trigger molecule has specific inhibitory activity for a polynucleotide (e.g., an mRNA) target when that RNAi trigger molecule inhibits the expression of the mRNA (or the polypeptide encoded by the mRNA) to a greater degree than it inhibits other mRNA molecules. The method used to measure the inhibitory activity can vary depending on the reporter/assay system that is used.

As used herein, the expression "specific for a target mRNA" refers to the property of an RNAi trigger molecule where that RNAi trigger molecule inhibits the expression or activity of an mRNA target (or the polypeptide encoded by the mRNA target) to a greater degree than it inhibits other mRNA molecules. That RNAi trigger can be said to have "specific inhibitory activity" for the target mRNA.

As used herein, the expression "off-target effect" refers to the effect caused by an RNAi trigger molecule where that RNAi trigger molecule inhibits the expression or activity of an mRNA target (or the polypeptide encoded by the mRNA target) other than the target that it is most complementary to, or in other respects, the RNAi trigger molecule inhibits the expression or activity of an unexpected mRNA target or an undesirable mRNA target.

As used herein, the expression "single cell resolution" refers to the ability to sort, detect or quantitate a pool of cells with sufficient resolution such that the particular characteristics or properties of a single cell in the pool of cells can be distinguished from other individual cells in the pool of cells. For example, if one cell in a pool of cells is associated with a fluorescent reporter molecule to a greater degree than any other cell in the population, a detection system having "singe cell resolution" will be able to detect, and in some cases, sort and isolate, that one cell from the population of cells.

As used herein, the expression "positive selection marker" refers to a marker that, when present in a cell, e.g., expressed, activated or the like, results in detection, identification and/or survival of that cell that comprises the marker.

As used herein, the expression "negative selection marker" refers to a marker that, when present in a cell, e.g., expressed, activated or the like, results in the death or counter-selection of the cell that comprises that marker.

As used herein, the expression "shRNA cassette" or the like refers to a DNA molecule, which when transcribed, has the ability to produce a transcript that is an shRNA that triggers RNAi, or can be further processed to generate an shRNA that triggers RNAi.

As used herein, the expression "hairpin cassette" or the like refers to a DNA molecule, which when transcribed, has the ability to produce a hairpin molecule.

As used herein, the term "epiallele," "epiallele variant" or similar expressions refer to a phenotypic variant that is induced by genetic variability other than the genetic variability that is associated with allelic variation. For example, dominant genetic inhibitors such as antisense-RNA or shRNA molecules that cause a spectrum of phenotypic severity are epiallelic.

As used herein, the expression "epiallelic series" or similar expressions refer to a collection of epialleles of a target gene that cause a spectrum of phenotypic severity.

As used herein, the terms "hypomorphic," "hypomorphic allele," "hypomorphic mutation" or the like refers to a genetic variant that results in a reduction-in-function of a particular gene. The hypomorphic state can be caused by a mutation in the endogenous copy of a gene, or can be caused by epi-allelic factors such as pharmaceutical inhibitors or dominant genetic inhibitors, e.g., shRNA molecules.

BRIEF DESCRIPTION OF THE FIGURES

FIGS. 4A and 4B provide illustrations of the "opening out" mechanism used during construction of an shRNA cassette using the methods of the present invention. FIG. 4A shows an "opening out" using an adaptor oligonucleotide method, as shown in FIG. 2. This protocol includes the following steps. Step A: Ligate on cloning adaptor loop. Step B: Anneal primer and extend (or extend from a nick between vector and stem-loop). Bst DNA Polymerase can efficiently copy the whole loop because it can displace the base-paired DNA. No amplification avoids bias. Products 130 base pairs and larger are big enough to gel purify efficiently.

FIG. 4B shows the cloning of an "opened out" shRNA cassette into a vector. This protocol includes the following steps. Step C: Gel purify. Step D: Subclone into a suitable expression cassette by digesting with cloning enzymes. In a preferred method, this isn't required as the opened out loop is already attached to the vector. All that is required is to circularize the vector by ligation. Step E: If necessary, subclone the expression cassette into an appropriate vector, e.g., a retroviral expression vector. Step F: Transcribe the expression cassette in a host cell to produce a candidate shRNA.

FIGS. 5A-5C provide the sequences and secondary structures of hairpin DNA molecules. In the figures, the characters N/N', X/X' and Y/Y' mean any base, and where with the prime symbol denotes that the base is the complementary base to the corresponding N, X or Y. Restriction sites are circled.

FIG. 15 provides an illustration of the state of a vector after completion of polymerisation with strand displacing polymerase and blunting of other end of vector. Recircularisation with T4 DNA ligase yields the complete first stage vector. Note that the 'sense' strand of the shRNA corresponds precisely to the start of transcription, while the 'antisense' strand is immediately followed by the terminator. —PO=5' phosphate —OH=3' hydroxyl.

FIG. 16 provides an illustration of a vector where the removal of stuffer from the cloned opened-out hairpin construct is shown. The stuffer within the hairpin loop is removed using a pair of restriction enzymes which cut outside their recognition site (here, GsuI). After GsuI cutting, the vector is optionally treated with an enzyme to produce blunt ends, optionally gel purified and recircularised by ligation. The recircularised vector can optionally then be amplified cloning into a suitable bacterial strain. The completed cassette carrying the hairpin construct is then transferred into the final vector.

FIG. 19 provides a photograph of an agarose gel following PacI/HindIII digestion and resolution of a mixed library DNA preparation.

FIG. 20 provides a table showing the nucleotide sequences from eight of ten sequenced clones of the hairpin shRNA cassettes obtained following VEGFR2/KDR single gene library construction. The sequences from transcription initiation to transcriptional terminator (TTTTT) are shown.

FIG. 25A shows fluorescence micrographs of the same field of cells with red fluorescence (left) and green fluorescence (right). The red fluorescence marks cells that have received the indicated shRNA. The green fluorescence is from GFP-PEST expressed from the GFP-PEST reporter construct indicated. The reporter construct in the bottom row carries an Axl cDNA downstream of the GFP-PEST/hygromycin open reading frame, while the control reporter lacks these sequences. Neither reporter construct responds to the luciferase shRNA (left panels). The reporter construct which includes the Axl cDNA responds to the Axl shRNA with a reduction in GFP levels (bottom right) while the control construct (top right) does not. FIG. 25B top panel shows a FACS analysis of GFP-PEST expression from the control reporter construct illustrating that reporter expression is unaffected by the presence of either the Luc shRNA (green) or the Axl shRNA (blue). Controls are cells lacking the reporter (orange) and cells carrying the reporter but without any shRNA (red shaded). FIG. 25B bottom panel shows a FACS analysis of GFP-PEST expression from the reporter construct carrying the Axl cDNA. Cells expressing the Axl shRNA (blue) have reduced GFP fluorescence when compared to cells expressing the Luc shRNA (green) or the reporter construct alone (red shaded). Cells lacking the reporter construct (orange) are also shown, indicating the level of background (non-GFP) fluorescence from the cells.

FIGS. 26A-C provide results illustrating that fluorescence from the reporter construct accurately mirrors effects on the target protein. FIG. 26A shows GFP fluorescence from a reporter construct carrying the Axl cDNA in response to three differently-effective Axl shRNAs (magenta, brown, blue). Cells expressing a control Luc shRNA (green shaded)

and lacking the reporter construct (orange shaded) are also shown. FIG. 26B shows a FACS analysis of the same cells as in FIG. 26A, but stained for Axl protein with an anti-Axl antibody and fluorescent secondary antibody. The orange shaded population represent background fluorescence from cells stained without the primary antibody. The three different Axl shRNAs produce qualitatively the same knockdown of Axl protein as GFP fluorescence. In each case Axl-2 shRNA is most effective, followed by Axl-280 shRNA and Axl-278 shRNA. FIG. 26C depicts reporter gene fluorescence after background subtraction. After the background subtraction, the mean GFP-PEST reporter gene fluorescence is linearly related to the level of Axl protein measured in the different cell lines tested.

FIG. 27A provides results from quantitative RT-PCR of Axl mRNA in wildtype (wt) cells or cells expressing one of four Axl shRNA constructs of differing effectiveness. Shown is the percentage knockdown of Axl mRNA levels compared to cells expressing a control shRNA (Luc shRNA).

In FIG. 28A, a retroviral GFP-PEST reporter construct carrying proteasomal subunit beta5 was introduced into the HSultan cell line. Populations of these cells were infected with retroviruses carrying different shRNA constructs potentially targeting beta5. GFP fluorescence was measured by FACS analysis. Results for three such shRNAs are shown, identifying two active shRNAs (#1 and #3). An inactive shRNA (#2) is shown for comparison. Also shown (top left) are cells carrying only the reporter construct or the reporter construct and a control (Luc shRNA) construct. FIG. 28B provides western blots of proteins from the above cell populations. The top panel of FIG. 28B shows the loading control (stained with an anti-tubulin antibody). The lower panel is stained with antibody against proteosomal subunit beta 5. Reduced protein levels are clearly seen in the cell populations carrying shRNA #1 and shRNA #3. Two different methods of preparing the cells (lysis in NP-40 buffer followed by addition of loading buffer, or direct lysis in loading buffer (LSB)) are shown, producing equivalent results.

FIG. 37 provides tables of polynucleotide sequences of the invention.

DETAILED DESCRIPTION OF THE INVENTION

The present invention provides novel enzymatic synthesis strategies for constructing improved siRNA molecules, and further where the siRNA molecules can be assembled as gene-specific and/or genome-wide RNAi libraries suitable for pharmaceutical screening. The invention also provides high-throughput methods for testing the specific inhibitory activity of an RNAi trigger molecule, methods for identifying active RNAi trigger molecules from a library of candidate trigger molecules, and methods for identifying the natural mRNA target of a known RNAi trigger molecule.

These aspects of the invention address several of the important limitations in pharmaceutical application of contemporary RNAi technology. Most significantly, the new molecules and methods described herein are able to identify RNAi effectors (i.e., RNAi trigger molecules) not predicted by current known methodologies. One of the strengths of the present invention is that the RNAi trigger molecules of the invention are constructed and validated without the need for preselection by imperfect computer algorithms. The selection of RNAi trigger molecules by the present invention is functional, and is not biased by computational in silico predictions. In silico predictions frequently fail to predict active RNAi inducing molecules.

Figure 35:
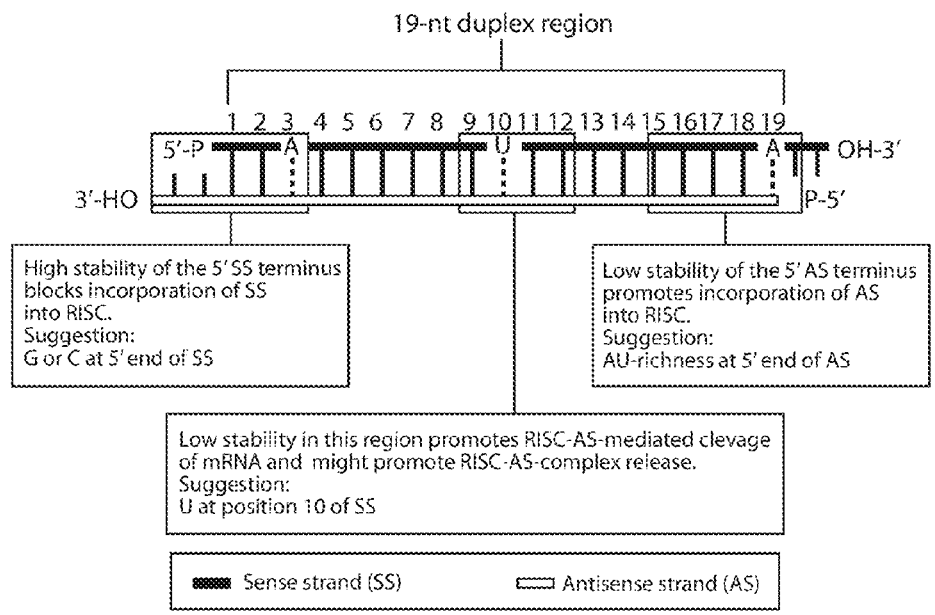
FIG. 35 provides an illustration demonstrating the drawbacks of traditional in silico prediction methods for identifying shRNA elements. The top panel summarizes some of the features thought to be important for in silico prediction of RNAi trigger molecule efficiency. The lower panel illustrates two highly active shRNA elements identified using the material and methods of the invention.

FIG. 35 provides an illustration demonstrating the limitations of traditional in silico prediction methods for identifying shRNA elements. The top panel summarizes some of the features thought to be important for in silico prediction of RNAi trigger molecule efficiency. The lower panel illustrates two highly active shRNA elements specific for the Axl gene that were identified using the materials and methods of the present invention.

The two RNAi trigger molecules shown in FIG. 35 score very poorly using a typical set of in silico prediction rules (see Reynolds et al., *Nat. Biotechnol.* 22(3):326-330 (2004)). These scoring parameters are as follows:

+1 point if sequence is between 30% and 52% GC
+1 point for each A or T at positions 16-19
+1 point if position 19=A
+1 point if position 3=A
+1 point if position 10=T
−1 point if position 19 is G or C
−1 point if position 13 is G Other references also provide parameters for predicting the suppression efficiency of potential RNAi trigger molecules. These include Ui-Tei et al., "Guidelines for the selection of highly effective siRNA sequences for mammalian and chick RNA interference," *Nucleic Acids Res.*, 32(3):936-948 (2004) and Tuschl, "Expanding small RNA interference," *Nat. Biotechnol.*, 20(5):446-448 (2002).

Despite the very poor in silico algorithm prediction scores, these two molecules showed very high efficiency in knocking down expression of Axl expression, as measured by both reporter gene activity (FACS analysis) and levels of endogenous Axl protein (Western blotting using an anti-Axl antibody). Thus, reliance on the typical set of in silico prediction rules results in failure to predict all RNAi inducing molecules.

There are a variety of advantages to using the compositions and methods of the invention for producing RNAi trigger molecules that distinguish this invention from techniques currently known in the art. Using the present invention, selection of RNAi trigger molecules can be done in any relevant cell line of interest, and can target any known gene. Another key advantage to the methods of the present invention is that no target specific antibodies for the gene of interest are required. The selection process can use a generic reporter protein e.g., a fluorescent protein that can be gated by fluorescence activated cell sorting.

In some aspects, the integrated RNAi technology of the present invention provides the following.

(1) Novel methods to create a large gene-specific population of candidate RNAi sequences, e.g., in a high-titer retroviral vector system. This is accomplished using unique combinations of specially engineered oligonucleotide adaptors, enzymatic modifications and/or tailored purification systems. The siRNA libraries of the invention can comprise a random assortment of sequences derived from input gene transcripts and can be expressed from an optimized vectors, e.g., retroviral vectors. The complexity of the library can be controlled (e.g., at least 50 or more independent RNAi sequences per gene, at least 100 or more independent RNAi sequences per gene, or most preferably, at least 1000 or more independent RNAi sequences per gene) and large libraries can be generated. This large complexity dramatically increases the probability of identifying active RNAi sequences.

(2) Novel functional RNAi selection systems that can be used to identify novel RNAi-effectors (i.e., RNAi trigger molecules) that effectively target selected therapeutic genes. In some aspects, this system is a FACS-based system. In some aspects, the selection system uses retroviral vector delivery/expression system. One of the distinct advantages of this approach is a direct cell-based identification of functional RNAi species, selected for optimal performance in the context of pharmaceutically relevant cells. Hence, functional siRNA sequences can be identified that are not predictable by the widely-used siRNA sequence selection algorithms. As shown herein, the novel targeting sequences determined by the methods of the invention could not be predicted by current siRNA sequence selection algorithms. Hence, this approach allows the identification of novel RNAi effectors against sequences previously thought not to be "targetable" by standard artificial siRNA molecules.

(3) Genome-wide RNAi library screening applications to identify and validate pharmaceutical therapeutic targets. Novel embodiments of the technology provide the opportunity to conduct high-throughput screens for critical components of disease.

RNAi and siRNA Molecules

The term "RNA interference" ("RNAi," sometimes called RNA-mediated interference, post-transcriptional gene silencing, or quelling) refers to a phenomenon in which the presence of RNA, typically double-stranded RNA, in a cell results in inhibition of expression of a gene comprising a sequence identical, or nearly identical, to that of the double-stranded RNA. The double-stranded RNA responsible for inducing RNAi is called an "interfering RNA." Expression of the gene is inhibited by the mechanism of RNAi as described below, in which the presence of the interfering RNA results in degradation of mRNA transcribed from the gene, and thus decreases the levels of the mRNA and any encoded protein. The RNAi mechanism also includes blocks in the translation of the mRNA transcribed from the gene, thus resulting in decreased levels of the encoded protein. RNAi can under some circumstances also lead to a decrease in the transcription of the mRNA, also leading to decreased levels of the mRNA and any encoded protein.

The mechanism of RNAi has been investigated in a number of eukaryotic organisms and cell types. In brief, double-stranded RNA introduced into a cell (e.g., into the cytoplasm) is processed, for example by an RNAse III-like enzyme called Dicer, into shorter double-stranded fragments called small interfering RNAs (siRNAs, also called short interfering RNAs). The length and nature of the siRNAs that are produced varies, although typically siRNAs are 20-25 nucleotides long (e.g., an siRNA may have a 19 base pair duplex portion with two nucleotide 3' overhangs at each end). Similar siRNA molecules can also be produced in vitro (e.g., by chemical synthesis or in vitro transcription) and introduced into the cell to induce RNAi. The siRNA becomes associated with an RNA-induced silencing complex (RISC). Separation of the sense and antisense strands of the siRNA, and interaction of the siRNA antisense strand with its target mRNA through complementary base-pairing interactions, optionally occurs. Finally, the target mRNA is cleaved and degraded or its translation is prevented. Thus, expression of a particular target gene in a cell can be specifically inhibited by introducing an appropriately chosen double-stranded RNA into the cell. Because double-stranded RNAs greater than 30-80 base pairs long activate the antiviral interferon response in mammalian cells and result in non-specific gene silencing, interfering RNAs for use in mammalian cells are typically (but are not necessarily exclusively) less than 30 base pairs in length.

Due to currently unexplained differences in efficiency between siRNAs corresponding to different regions of a given target mRNA, several siRNAs are typically designed and tested against the target mRNA to determine which siRNA is most effective. Interfering RNAs can also be produced as small hairpin RNAs (shRNAs, also called short hairpin RNAs), which are processed in the cell into siRNA-like molecules that initiate RNAi.

Short RNAs called microRNAs (miRNAs) have been identified in a variety of species. Typically, these endogenous RNAs are each transcribed as a long RNA and then processed to a pre-miRNA of approximately 60-75 nucleotides that forms an imperfect hairpin (stem-loop) structure. The pre-miRNA is typically then cleaved, e.g., by Dicer, to form the mature miRNA. Mature miRNAs are typically approximately 21-25 nucleotides in length, but can vary, e.g., from about 14 to about 25 or more nucleotides. Some, though not all, miRNAs have been shown to inhibit translation of mRNAs bearing partially complementary sequences. Such miRNAs contain one or more internal mismatches to the corresponding mRNA that are predicted to result in a bulge in the center of the duplex formed by the binding of the miRNA antisense strand to the mRNA. The miRNA typically forms approximately 14-17 Watson-Crick base pairs with the mRNA; additional wobble base pairs can also be formed. In addition, short synthetic double-stranded RNAs (e.g., similar to siRNAs) containing central mismatches to the corresponding mRNA have been shown to repress translation (but not initiate degradation) of the mRNA.

The cellular machinery involved in translational repression of mRNAs by partially complementary RNAs (e.g., certain miRNAs) appears to partially overlap that involved in RNAi, although, as noted, translation of the mRNAs, not their stability, is affected and the mRNAs are typically not degraded.

Although significant advances have been made in understanding the molecular mechanisms underlying RNAi, this understanding is not required in order to make or use any aspect of the invention. Indeed, construction and use of the invention is entirely independent of the in vivo mechanisms that result in the RNA interference. It is not intended that the invention be limited in any way limited to any particular in vivo mechanism of action. Indeed, other mechanisms that remain unidentified can be responsible for the gene inhibition that is observed when using the invention.

Methods for Producing Hairpin DNA Molecules for the Production of siRNA Molecules The invention provides methods for producing a DNA molecule, that when transcribed produces a hairpin transcript that is an shRNA molecule or a shRNA-precursor molecule (i.e., a molecule that resembles a pri-miRNA). The shRNA thus formed can be a bonafide shRNA having RNAi activity towards a mRNA target, or it can be a candidate shRNA molecule that will be verified (or disqualified) by further testing. These methods can be used to create a single shRNA candidate molecule, or can be used to generate a library comprising a plurality of shRNA molecules.

The hairpin transcript contains stem sequences (at least 22 base pairs in length) corresponding to an mRNA, thereby making that shRNA a candidate RNAi trigger molecule that is specific for the regulation of the target mRNA from which the at least 22 base pairs was derived. These methods can use either a "vector attached" subcloning protocol (outlined in FIG. 1) or an "adapter oligonucleotide attached" subcloning protocol (outlined in FIG. 2). These two protocols produce the same "DNA effector intermediate" that encodes the RNA molecule (e.g., an siRNA) that is an RNAi effector candidate, and differ only in how the DNA effector intermediate is subcloned for propagation and expression.

Vector-Attached (Also Termed Semi-Attached) Method

Figure 1:
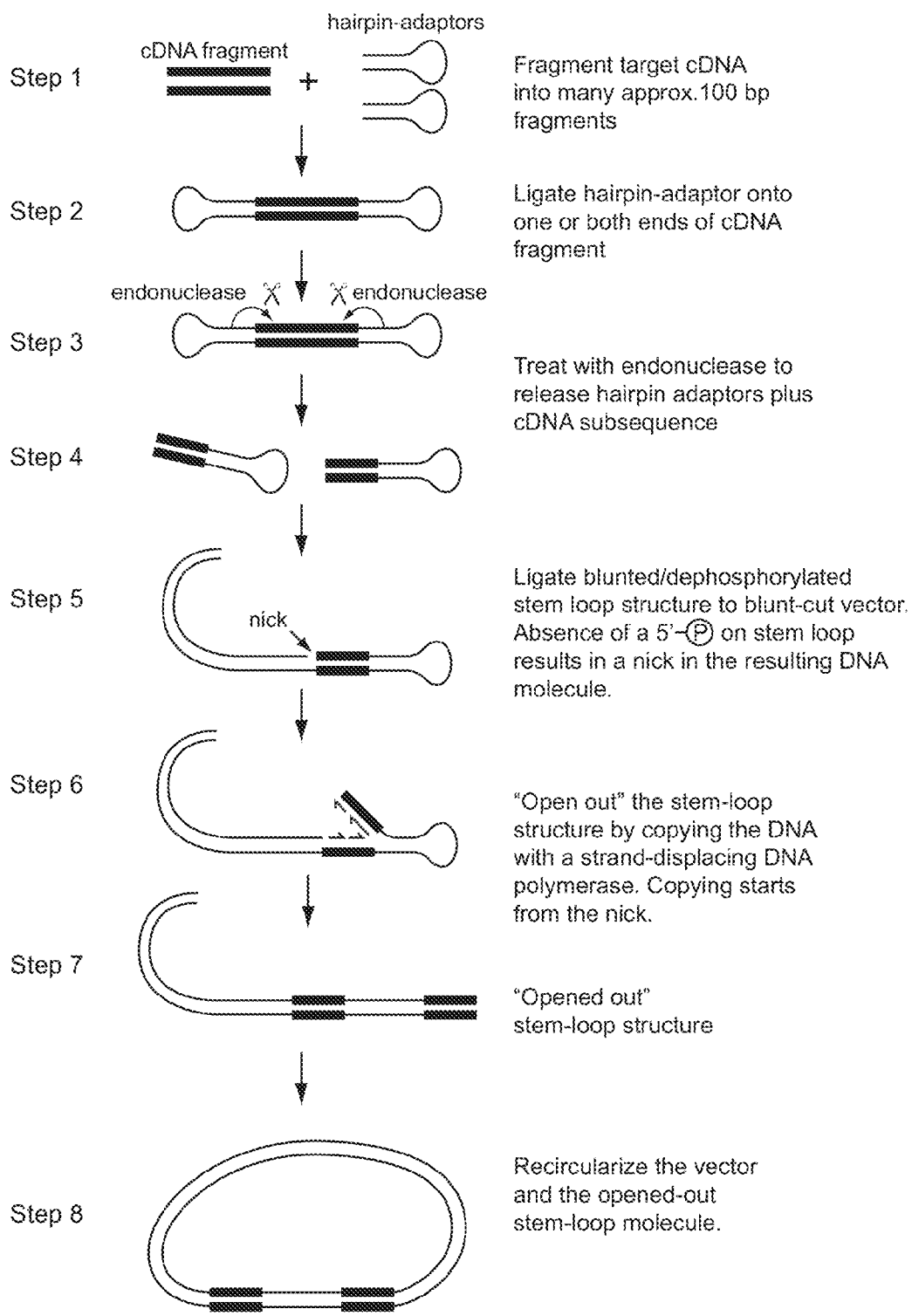
FIG. 1 provides an illustration depicting the construction of a hairpin DNA siRNA expression cassette and a vector containing the cassette, where the construction method employs a "hairpin adapter" methodology combined with a vector-attached "opening out" step. This protocol includes the following steps. Step 1: Fragment the target cDNA into many fragments at least approximately 100 base pairs in length. Step 2: Ligate the hairpin adapter onto one or both ends of the cDNA fragment. Step 3/4: Treat with endonuclease to release hairpin adapters plus cDNA subsequence. Step 5: Ligate blunted/dephosphorylated stem loop structure to blunt-cut vector. Absence of a 5'-phosphate group on stem loop results in a nick in the resulting DNA molecule. Step 6: "Open out" the stem loop structure by copying the DNA with a strand-displacing DNA polymerase. Copying starts from the nick. Step 7: Produce the "opened out" stem-loop structure. Step 8: Recircularize the vector and the opened-out stem-loop molecule, followed by further conventional cloning steps.
Figure 3:
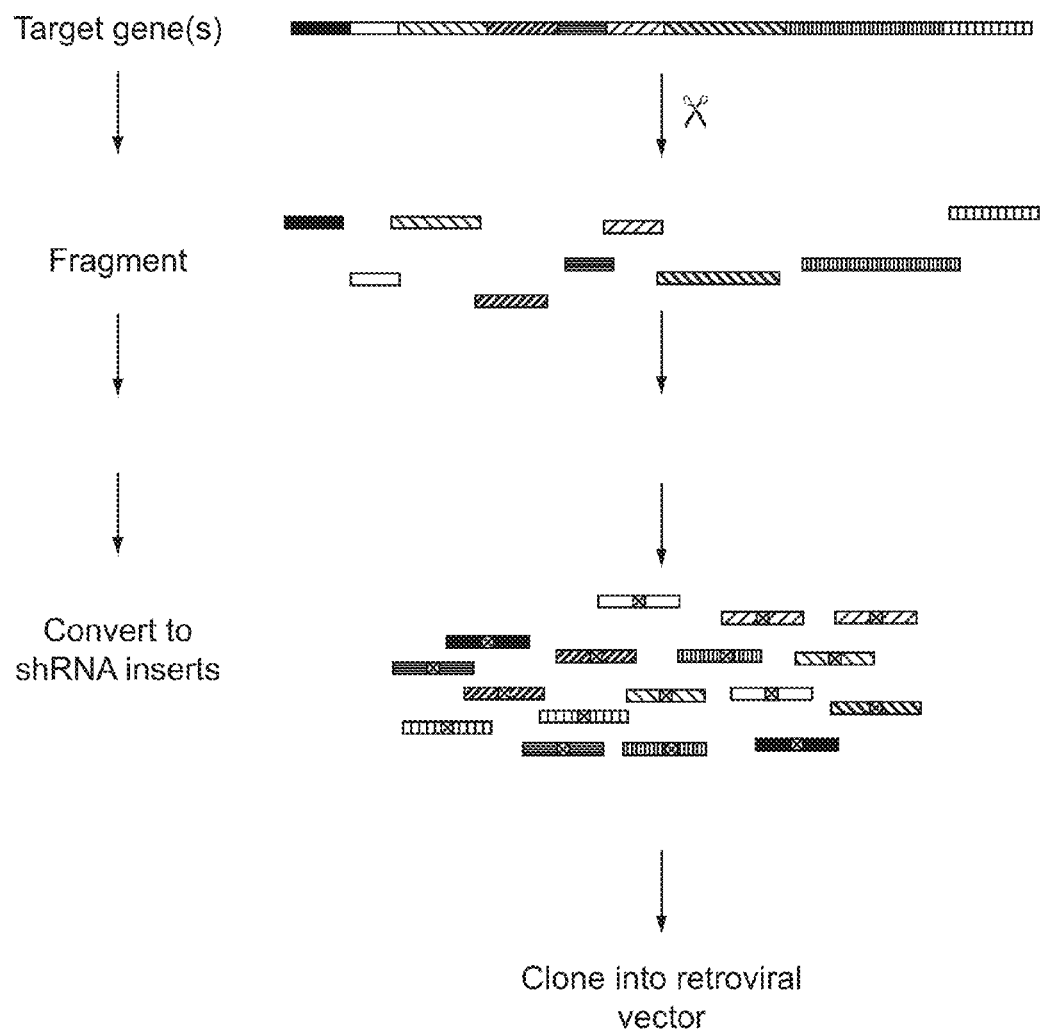
FIG. 3 provides an illustration of the construction of an shRNA library from a target gene cDNA.

FIG. 1 shows an outline of the "vector attached" protocol for producing a DNA construct the expresses an RNAi effector candidate. In step 1, a cDNA of interest is first fragmented by any suitable means (mechanical or enzymatic) to produce many small double-stranded fragments. The length of these fragments need not be limited except that they must be (or a majority of the fragments must me) at least 22 base pairs in length. Fragments can be, for example, at least 50 base pairs in length, or alternatively and most typically at least 100 base pairs in length. This fragmentation and subsequent processing to generate shRNA inserts is illustrated in FIG. 3.

These cDNA fragments are then used in a ligation reaction with an adapter oligonucleotide of the invention (step 2). The ligation event can occur at only one end of the cDNA fragment, or at both ends. When the ligation event occurs at both ends of the cDNA fragment, a dumbbell-shaped molecule is formed. A critical feature of the adapter oligonucleotide is that it contains an endonuclease recognition site in the stem domain that is recognized by a corresponding endonuclease that cleaves at a site at least 22 base pairs distant from the recognition sequence. Such restriction enzymes can include, but are not limited to, EcoP15I, McrBC, EcoP1 and PstII. In order to improve cloning efficiency, the hairpin adapters can be 5'-dephosphorylated prior to the ligation reaction.

The resulting ligation products are then cleaved with the appropriate restriction enzyme (step 3) to generate either one or two hairpin cleavage products (step 4), depending on whether the hairpin adapter oligos were ligated to one or both ends of the cDNA fragment. These hairpin cleavage products are "DNA effector intermediates" that encode the RNA molecules (e.g., siRNA molecules) that are RNAi effector candidates. These DNA effector intermediates comprise at least 22 base pairs of sequence derived from the cDNA, but can contain cDNA-derived sequences longer than 22 base pairs, depending on the restriction enzyme used. For example, a DNA effector intermediate can contain at least 25, at least 30, at least 35, at least 40, at least 45, at least 50, at least 55 or at least 60 base pairs of cDNA-derived sequence. Depending on the restriction enzyme used, it is possible that the at least 22, at least 25, at least 30, at least 35, at least 40, at least 45, at least 50, at least 55 or at least 60 base pairs of cDNA sequence may be partially single-stranded due to 3' or 5' overhangs at the site of cleavage.

These DNA effector intermediates may or may not contain additional nucleotide base pairs derived from the hairpin adapter oligo. These additional nucleotide base pairs can optionally be deleted at a later step. For example, the hairpin adapter shown in FIG. 9 will contain 25 base pairs (plus a 2 base pair 5'-overhang) of cDNA sequence plus 16 base pairs of stem derived from the hairpin adaptor.

From this point, the DNA effector intermediate hairpin is subcloned for further manipulation and expression. This can be accomplished using a "vector attached" methodology, as shown in FIG. 1. The stem-loop DNA intermediate generated in step 4 is then ligated to a linearized cloning vector (a "vector adaptor"), typically by blunt-ending and then dephosphorylating the DNA intermediate prior to ligation. This produces a stem ligation product that contains a nick in the ligation product (step 5).

Figure 4A:
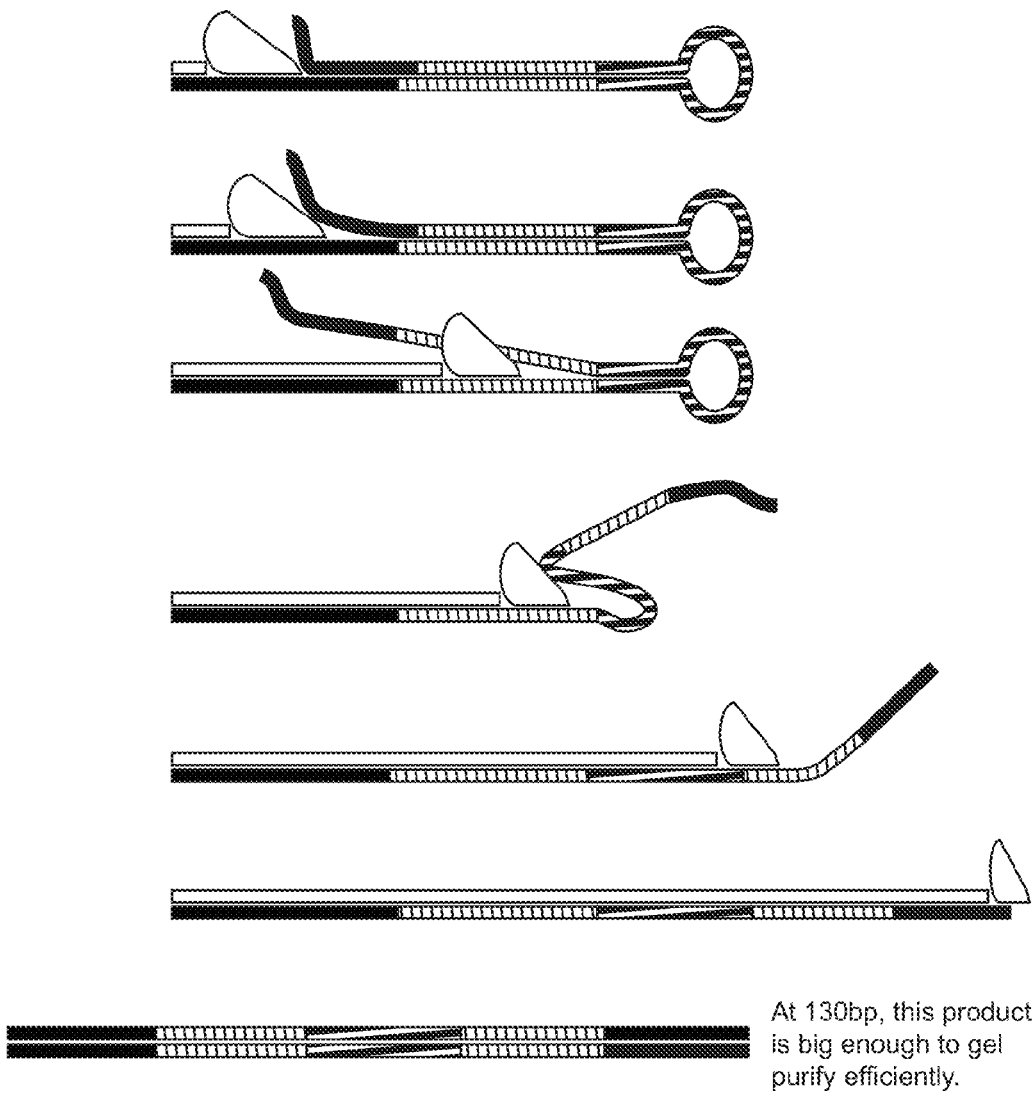
Figure 5D:
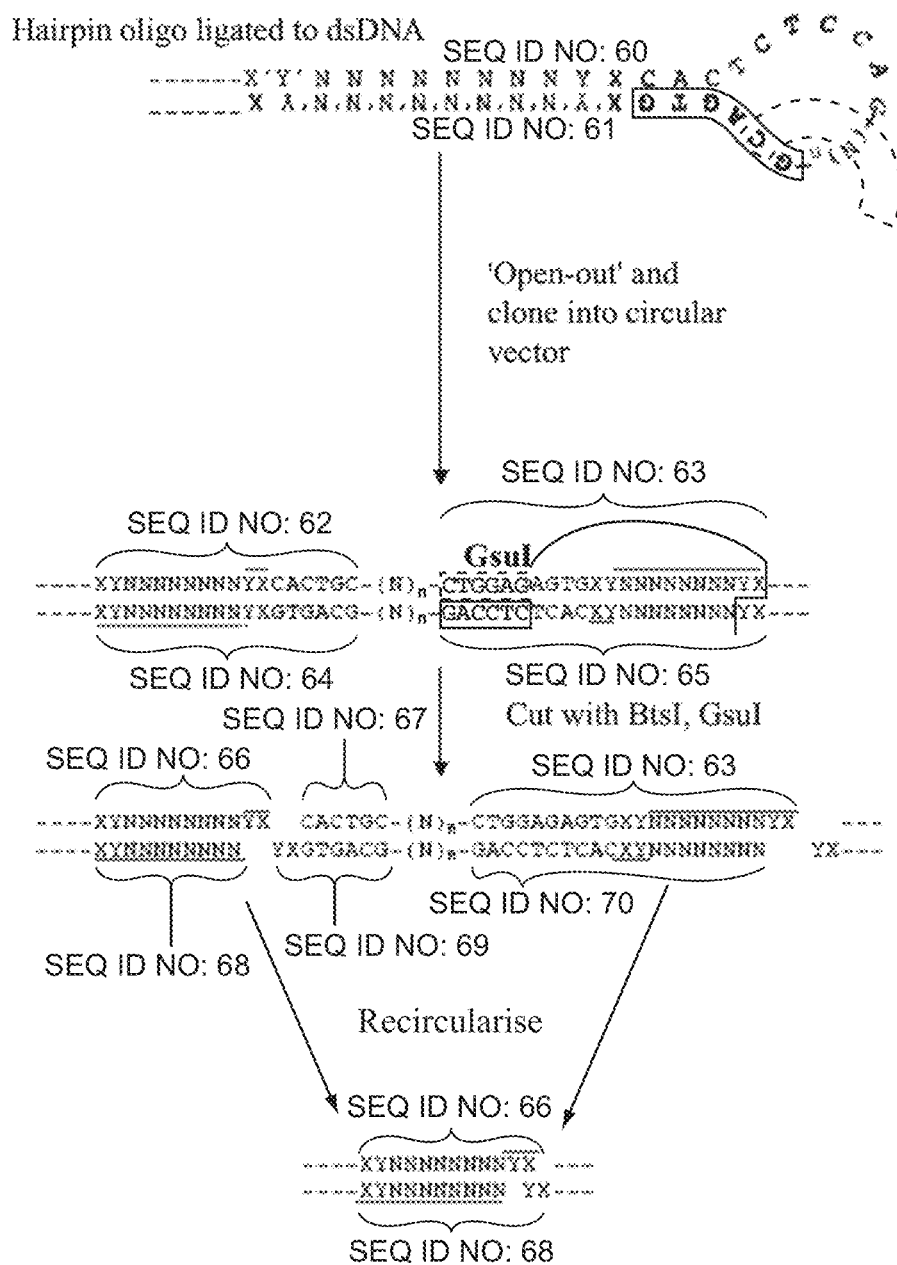
FIG. 5D provides an illustration showing the process of how a hairpin molecule (e.g., a hairpin of FIG. 5C) can be cut to excise unwanted sequences.

In order to remove the stem-loop secondary structure, the molecule is "opened-out" by copying the DNA with a strand-displacing DNA polymerase that initiates at the site of the nick (step 6). This opening-out reaction is illustrated in FIG. 4A, and generates a linear double-stranded vector (step 7) that can then be recirculated (step 8). Alternatively, once the molecule is linearized (and in lieu of recirculation or after recirculation), it can be subjected to any additional subcloning or manipulation prior to its cloning into a suitable expression vector (see FIG. 4B).

In some applications of this method, the DNA effector intermediates that are generated at step 4 are blunt-ended, dephosphorylated and ligated to a cloning vector cut with one blunt-cutting restriction enzyme and one non-blunt enzyme. These enzymes can be selected to minimize vector dimer/oligomerization. For example the non-blunt enzyme can be chosen to produce ends that are not self-complementary. The blunt-cutting enzyme can be included during the ligation to re-cleave vector dimers. The product of ligation will retain a 'nick' due to the lack of a 5' phosphate on the loops (which also inhibits loop dimerization). The loop can then be opened out using a strand-displacing DNA polymerase (e.g., DNA polymerase I Klenow fragment, Bst polymerase or Vent polymerase), which initiates at this nick. The same enzyme (or additional Klenow fragment or T4 DNA polymerase) can be used to make both ends of the vector blunt. Treatment with T4 DNA ligase produces circular DNA molecules that can be used to transform *E. coli*. Because the final ligation reaction is unimolecular, it proceeds with relatively high efficiency.

Adapter Oligo-Attached Method

Figure 2:
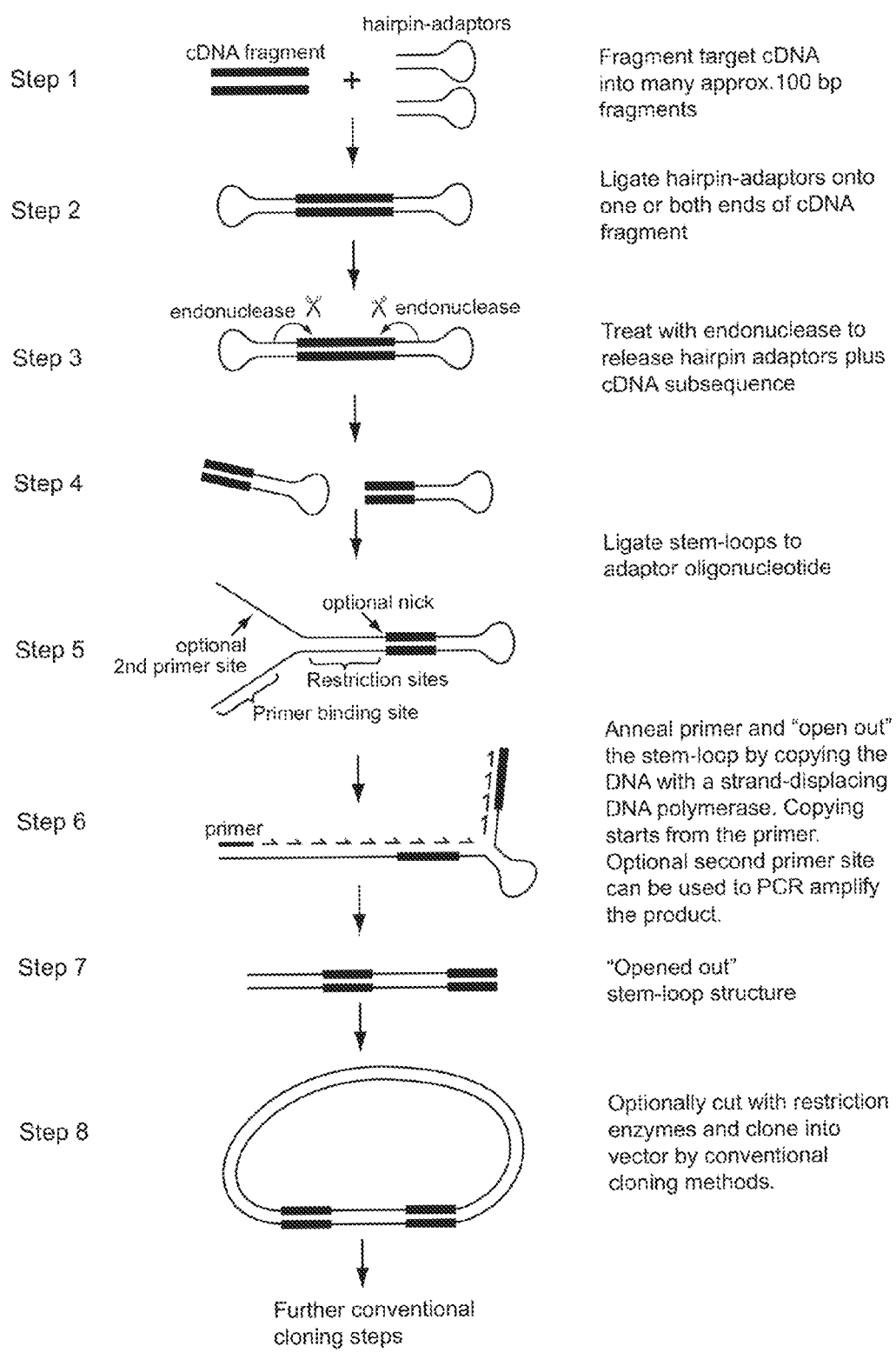
FIG. 2 provides an illustration depicting the construction of a hairpin DNA siRNA expression cassette and a vector containing the cassette, where the construction method employs an "adapter oligonucleotide" methodology and an "adapter oligonucleotide" "opening out" step. This protocol includes the following steps. Step 1: Fragment the target cDNA into many fragments at least approximately 100 base pairs in length. Step 2: Ligate the hairpin adapter onto one or both ends of the cDNA fragments. Step 3: Treat with endonuclease to release hairpin adapters plus cDNA subsequences. Step 5: Ligate stem loops to adapter oligonucleotides. Step 6/7: Anneal primer and "open out" the stem-loop by copying the DNA with a strand-displacing DNA polymerase, thereby producing an "opened out" stem-loop structure. Copying starts from the primer. An optional second primer site can be used to PCR-amplify the product. Step 8: Optionally cut with restriction enzymes and clone into a vector by conventional cloning methods. The protocol can then further include additional conventional cloning steps.

An alternative protocol termed the "adapter oligonucleotide attached" method for manipulating the "DNA effector intermediate" is outlined in FIG. 2. The first four steps of this protocol for generating the DNA effector intermediate are identical to the first four steps of the "vector attached" method of FIG. 1. These two protocols differ only in how the DNA effector intermediate is manipulated downstream.

As shown in FIG. 2, step 5, the DNA effector intermediate is ligated to an "adapter oligonucleotide" that can be variable in structure. This adapter oligonucleotide will minimally comprise sequences that can be used as a primer binding site to initiate DNA polymerization. In addition to that primer binding site, the oligo can contain any number of additional DNA elements that can facilitate downstream processing, such as restriction enzyme recognition sites. In some embodiments, the adapter oligos comprise binding sites for additional primers to be used in PCR amplification of the DNA intermediate product.

As shown in step 6, a suitable primer is annealed to the primer binding site in the adapter oligo, and the primer is used to initiate DNA polymerization using a strand-displacing DNA polymerase. This DNA polymerization results in an "opened out" molecule where the loop secondary structure has been removed (step 7). This double-stranded linear molecule is then manipulated and eventually cloned into a suitable expression vector (step 8).

Hairpin-Adapter Oligonucleotides

A key feature of the invention is the use of novel "hairpin adapter oligonucleotides" in the construction of the "DNA effector intermediate" that encodes the RNA molecule that is an RNAi effector, The hairpin-adapters of the invention each contain a double stranded stem domain and a loop domain, and further contain at least one endonuclease recognition site that is recognized by a first endonuclease that cleaves at a site at least 22 base pairs distant from the recognition site.

The adapter-oligonucleotides of the invention can optionally contain additional sequence elements that find use in, but are not limited to, subcloning, improving cloning efficiency, and providing selectable markers. These sequences can include restriction sites, sequences encoding reporter polypeptides, and lac operator recognition sites (lacO). Examples of adapter oligonucleotides include, for example, the oligonucleotides provided in FIGS. 5A-5C and 9-11.

In some embodiments, the hairpin adapter stem domain contains sequences that generate a de novo restriction enzyme site if two hairpin-adaptor oligos ligate to form a dimer. Digestion of the dimer product with the restriction enzyme regenerates the original hairpin-adaptor oligos. Inclusion of the restriction enzyme in the ligation reaction ensures that any hairpin-adaptor oligo dimers that form are recleaved and are available for ligation to cDNA.

Methods for Screening for Specific Inhibitory Activity of an RNAi Trigger Molecule for a Polynucleotide (e.g., mRNA) Target The invention provides methods for assaying whether a particular candidate RNAi trigger molecule has specific inhibitory activity for a particular polynucleotide target. This methodology is illustrated generally in FIG. 21.

Using this strategy, a reporter gene assay is adapted for the detection of RNAi trigger molecules (e.g., double stranded RNA, short hairpin RNA (shRNA), micro RNA (miRNA), shmiRNA and small interfering RNA (siRNA)) that are active in the down regulation of expression of a target gene (or the polypeptide encoded by the gene). The target gene to be used in the screening protocol can be an entire mRNA (i.e., the full length cDNA) or any portion of the cDNA.

The reporter construct consists of a reporter gene (including, but not limited to, green fluorescent protein (GPF) or another fluorescent protein) coupled to a protein signal that triggers rapid turnover of the reporter protein (including, but not limited to, the PEST domain from mouse ornithine decarboxylase). DNA encoding the desired RNAi target is cloned within the same transcription unit as the reporter gene and positioned 3' to the reporter gene in such a way that it is not translated. In one example, a stop codon can be placed between the reporter gene and the target sequence. This reporter transcription unit can be expressed under the control of any suitable promoter.

In the presence of an ineffective siRNA (i.e., an siRNA lacking specific inhibitory activity or in the absence of siRNA as a control), the reporter gene/target mRNA is transcribed and then translated. Note that the translation product will contain only the reporter polypeptide and the peptide that signals rapid turnover. The target sequence of interest will not be translated. The protein produced is subject to rapid PEST-mediated degradation, but it nevertheless accumulates to a steady-state level. The RNAi trigger candidate has no effect on the accumulation or degradation of the reporter polypeptide.

In the presence of an effective siRNA (i.e., an siRNA having specific inhibitory activity towards the target), the reporter gene/target mRNA is either degraded or its translation is blocked. The RNAi trigger candidate down regulates the rate of production of the reporter polypeptide. Less new reporter protein is produced, and any existing reporter protein is rapidly degraded. The steady-state level of reporter protein therefore drops rapidly. Thus, in the presence of an RNAi trigger molecule candidate (e.g., an siRNA) having specific inhibitory activity for the target gene of interest, the steady state level of the reporter polypeptide is lower than the steady state level that can be observed in the absence of any siRNA molecule expression, or using a control siRNA that is known to not have any degradation activity towards the target mRNA of interest.

The level of a reporter protein in individual cells can be easily measured (with single cell resolution). For example, a fluorescence activated cell sorter (FACS) can be used to measure GFP-PEST levels in individual cells, and optionally can be used to isolate cells with low GFP-PEST reporter levels. A magnetic tag with magnetic flow cell sorting can also be used.

The RNAi trigger molecule candidate can be supplied to the cellular experimental system by any desired method. For example, it can be expressed from an expression vector that has been cotransfected into the cell, or an in vitro produced RNAi trigger molecule can be directly transfected into the host cell by any suitable transfection method.

The reporter gene used in this method is not particularly limited. Although fluorescent reporter polypeptides find particular use with this method, other reporter systems also can be adapted for use. The reporter gene can be a cell surface marker polypeptide such as Lyt2, which can be detected by a labelled antibody. A reporter gene can encode a negative selection marker such as thymidine kinase (tk), HRPT and APRT. Other types of polypeptide reporter systems can also be adapted for use with this method, including luciferase polypeptides, β-galactosidase, α-lactamase, alkaline phosphatase and horse-radish peroxidase.

The type of vectors used to express the reporter polypeptide and/or the RNAi trigger molecule candidate are not particularly limited, and can be any type of vector that permits expression in the cell type used as the host. In various embodiments, the vector is a retroviral vector, a lentiviral vector, an adenoviral vector or any other type of eukaryotic expression vector.

RNAi Trigger Molecule Library Screening

The protocol described above for the assessment of a candidate RNAi trigger molecule for specific inhibitory activity towards a particular polynucleotide target can be readily adapted for the screening of RNAi trigger molecule libraries. In the library screening methods, the expression of a single RNAi trigger molecule is replaced by the expression of a library of molecules, where each RNAi trigger molecule is expressed in a separate cells, and each cell is analyzed with single cell resolution to identify to identify the library clones that have specific inhibitory activity for an mRNA target of interest.

Methods for Identifying a Target Polynucleotide (e.g., an mRNA) that is Specifically Targeted by a Known RNAi Trigger Molecule from a Library of Candidate Target Polynucleotides (e.g., a Library of cDNA Molecules)

Figure 29:
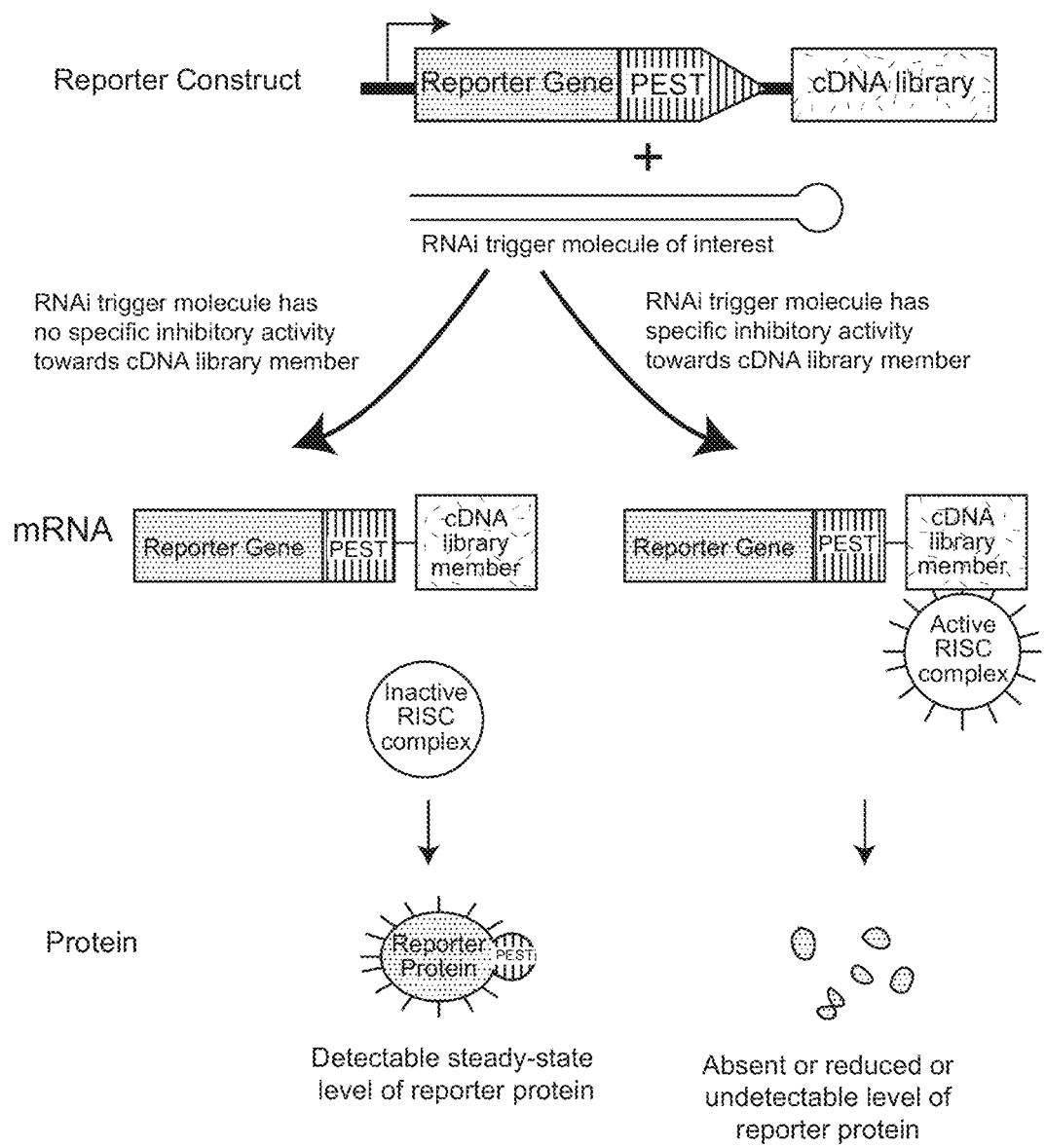
FIG. 29 provides an illustration of the strategy for an assay for identifying a cDNA target that is specifically targeted by a previously identified RNAi trigger molecule of interest.

A significant problem with existing shRNA/siRNA libraries and screens is that an shRNA/siRNA can specifically knock down the activity of a gene that is not the intended target. Identifying which gene is the actual target would be a considerable advantage. The invention provides methods for identifying a cDNA target from a library of candidate cDNA molecules that is specifically targeted by a previously identified RNAi trigger molecule of interest. These methods can be used to identify the targets of a given RNAi trigger molecule, and can also be used to determine if an RNAi trigger molecule has multiple targets. This methodology is illustrated generally in FIG. 29, and is described below.

To accomplish this, one can make a library of preferably all genes downstream of the reporter-PEST fusion gene, e.g., using gateway and an existing complete library, possibly an arrayed library. Alternatively, 3'UTR libraries can also be used. One will then infect this library with the shRNA/siRNA of interest, and identify and select (i.e., sort) those cells that show reduced reporter gene activity in response to expression of the RNAi trigger molecule. Multiple rounds of cell growth and sorting can be used.

Isolated (sorted) mRNA gene candidates will be subjected to high throughput DNA sequencing to identify the gene targets.

Alternatively, in an arrayed library, a row/column approach can be used to identify which wells contain positive clones, and the RNAi trigger target can be identified by the position of the well in the array to which the gene was distributed. This analysis can be combined with a 'candidate' approach using bioinformatics to provide the set of candidate genes to be tested.

Figure 21:
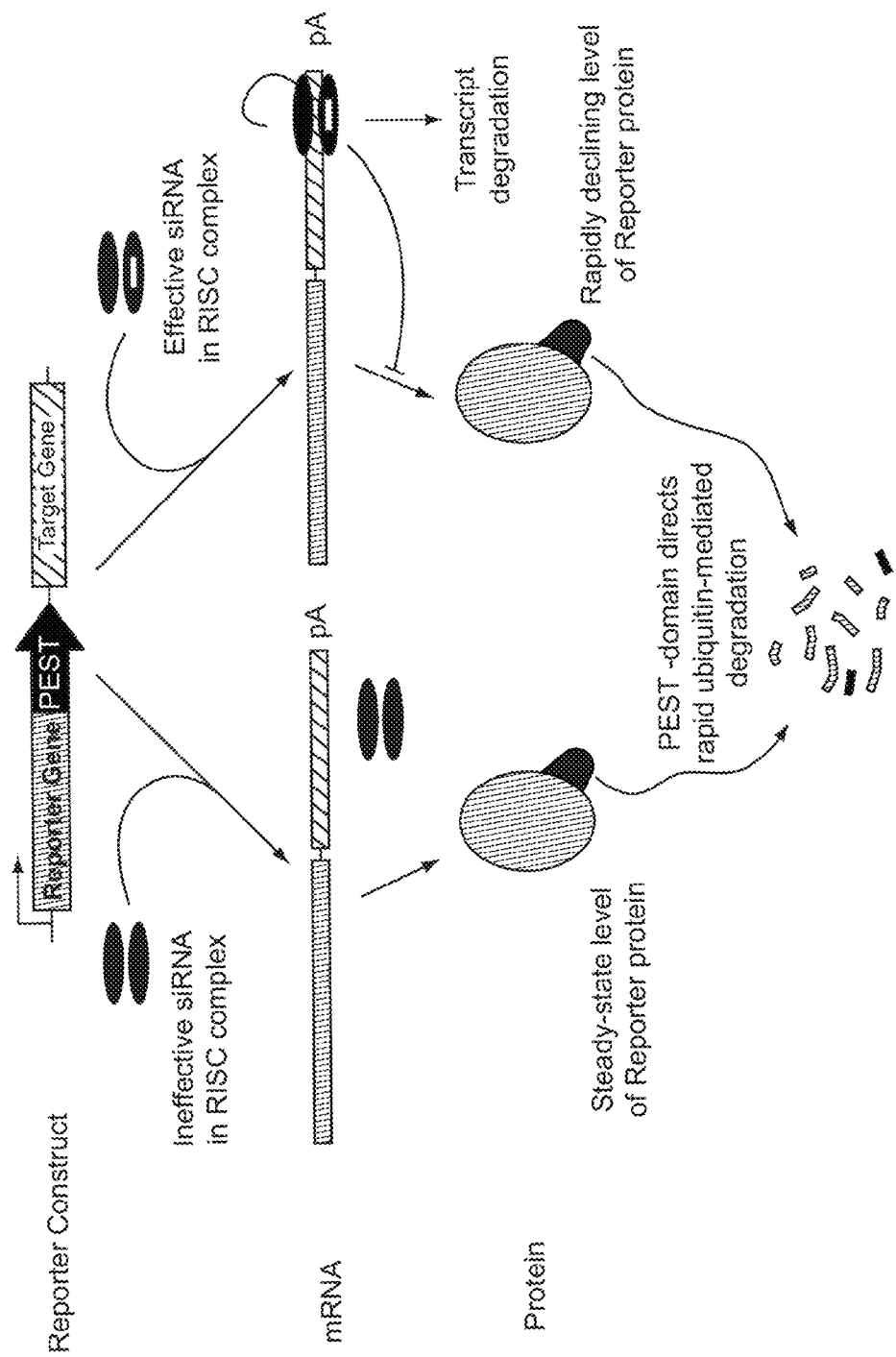
FIG. 21 provides an illustration of the strategy for a reporter gene assay for the detection of RNAi trigger molecules that are active in the down regulation of expression of a target gene.

The protocol described above for the screening of an RNAi trigger molecule library to identify molecules having specific inhibitory activity towards a particular known polynucleotide target can be readily adapted for the identification of mRNA targets for a known RNAi trigger molecule. In these modifications, the "target gene" sequence (as shown in FIG. 21) in the reporter fusion is replaced by a library of expressed genes. In that scenario, the expressed RNAi trigger library is replaced by a single RNAi trigger molecule whose target is unknown. An RNAi trigger molecule target is identified when expression of the reporter polypeptide is downregulated. See FIG. 29.

siRNA Libraries

The invention provides individual siRNA molecules as well as collections (libraries) of such molecules, in which each member in the library leads to the production of a different siRNA. The library is typically constructed in the context of a vector expression system, for example, a retroviral vector system. The intention behind constructing these libraries is that within the library there should be at least one vector able to regulate the expression of a target gene. These libraries must therefore contain a diversity of siRNA sequences. The invention provides a series of novel methods and improvements in the construction of libraries that contain a diversity of RNAi-enabling sequences (i.e., RNAi trigger molecules). The invention further provides novel functional approaches to identify sequences within the library that display the desired RNAi effect on expression of a target gene. These methods can provide an integrated system for identifying RNAi-element sequences that are active and specific for particular target genes.

Library Diversity

There are currently two strategies that are used to generate diversity in siRNA (e.g., shRNA) libraries. In the first, the sequence of the target gene(s) is examined, and computer algorithms are used to predict which sequences might produce an active siRNA against the target gene. For each target gene a small number of these sequences are selected. Library inserts encoding the selected sequences are chemically synthesized and either transfected into the cell directly or cloned into a vector to form a library. In the second approach, complementary DNAs (cDNA) derived from cellular mRNA are fragmented and each fragment is processed through a series of in vitro enzymatic reactions in order to produce a final construct that encodes a hairpin structure in which the double-stranded stem of the hairpin includes sequences from the original cDNA (an shRNA cassette).

One embodiment of this second approach is used in the REGS procedure as described in Sen et al., "Restriction enzyme-generated siRNA (REGS) vectors and libraries," *Nature Genetics* 36(2): 183-189 (2004). Briefly, in the REGS procedure, the target DNA is fragmented and ligated to a hairpin-adaptor oligo that includes a recognition site for the restriction enzyme MmeI. MmeI cuts DNA at a distance of 18/20 nucleotides from its recognition site. When the ligated DNA is cut with MmeI, short hairpin-shaped DNA molecules are released. These consist of a section of target DNA around 18-21 nucleotides long ligated to the hairpin-adaptor oligo. These short hairpins are then gel purified.

In the next step in the REGS protocol, the short hairpins are ligated to a second adaptor oligo that includes restriction enzyme sites that will be used to clone the finished construct, and gel purified again. In the case of REGS, this second adaptor oligo is also a hairpin oligo. This results in a "dumbell"-shaped molecule—a circle of single-stranded DNA including a region of self-complementarity. The purified construct must then be 'opened out' by copying the single DNA strand into double-stranded DNA. In the REGS procedure this is achieved by amplifying the construct by rolling circle-rolling replication. This produces a very long double stranded DNA molecule consisting of a tandem array of many copies of the desired construct. By cutting with the restriction enzymes whose sites were included in the second hairpin-adaptor oligo, individual copies of the desired final product are released. The fragments are then gel purified and cloned into a suitable vector.

At this stage, each insert of the REGS library consists of, in order:
  (A) a short sequence (including a restriction enzyme site) from the second adaptor oligo;
  (B) 18-21 nucleotides derived from the cDNA;
  (C) the sequence from the first hairpin-adaptor oligo;
  (D) the reverse-complement of the above 18-21 nucleotide cDNA-derived sequence; and
  (E) a short sequence (or possibly absent) from the second adaptor oligo.

In the REGS procedure, the first hairpin-adaptor oligo is quite long. This is necessary because the hairpin-adaptor oligo must include both the MmeI restriction site and enough double-stranded stem to be an efficient substrate for DNA ligase. A BamHI site is included in the stem of the hairpin, and this restriction site becomes duplicated during the amplification step. By digesting each clone in the library with BamHI and recircularising the vector, the loop can be considerably shortened, improving performance of the library.

This REGS procedure suffers from various limitations, including:
  (A) The cDNA-derived sequence in the hairpin stem is limited to 18-21 nt, which is less than the optimal length for efficient RNAi. Although the final active siRNA molecules are optimally 21 nt long, hairpins of 22-29 nt are more efficiently processed into 21 nt siRNAs than hairpins of 18-21 nt.
  (B) For the approach to work, the last two basepairs of cDNA-derived sequence must be CG. This limits the number of potential shRNAs that can be made from a given gene, especially as the dinucleotide CG is relatively rare in mammalian genomes.
  (C) The products of the MmeI digestion have 2 nt 3' overhangs of unknown sequence. The second hairpin adaptor oligo must therefore be present in 16 different versions to match all potential 2 nt overhangs. Among all possible pairings of MmeI-product and second hairpin adaptor version only one in sixteen will be capable of ligation, significantly reducing the efficiency of this ligation step.
  (D) In order to incorporate the restriction sites required for subsequent cloning of the shRNA cassettes, the second hairpin adaptor must include base mismatches in its stem region, and these must be close (6-8 nt) to the site of ligation. T4 DNA ligase, the enzyme typically used for such ligations, is sensitive to mismatches in this region, further reducing the efficiency of this ligation step.
  (E) Amplification by rolling circle replication generates significant bias in the diversity of the library produced. This is because the limiting step for rolling circle amplification is initiation—individual molecules for which amplification has started become amplified at the expense of molecules which have not yet initiated amplification. As a result, a small number of shRNA sequences out of the total available diversity tend to become dominant.
  (F) The method of reducing the loop size is very inflexible with respect to the final loop sequence obtained, which must be TTGGATCCAA (SEQ ID NO: 31). This sequence folds into a hairpin with a stem (TTGGA or a subset of this) that will extend the cDNA-derived stem sequence but which does not match the target mRNA.

The present invention provides a series of novel methods that can be used to improve the efficiency of the REGS procedure as well as other schemes for converting cDNA into constructs that encode a hairpin structure in which the double-stranded stem of the hairpin includes sequences from the original cDNA.

siRNA Molecule Delivery Systems

Some embodiments of the invention as described herein utilize retroviral-based systems for the delivery and expression of shRNA molecules and various reporter constructs in cells. Such retroviral systems find use with the invention, but the invention is not limited to such systems.

Retroviral vector-based, stable expression systems are well established, and are used frequently in high-throughput screening methodologies. Various features of retroviral systems makes them a powerful tool and highly adaptable. These systems can stably express an shRNA in any desired cell type, can express optimized shRNA structures and can be manipulated for conditional expression in vitro or in vivo, for example by using the tet-repressor (TRN) that uses doxycycline to control gene repression/derepression.

For descriptions of such retroviral systems, see, for example but not limited to, Lorens et al., "The use of retroviruses as pharmaceutical tools for target discovery and validation in the field of functional genomics," *Current Opinion in Biotechnology* 12: 613-621 (2001) and Intl. Patent Appl. No. WO 03/076592, by Lorens, entitled "Novel method for delivery and intracellular synthesis of siRNA molecules," filed on Mar. 6, 2003.

It is not intended that the invention be limited to retroviral-based delivery systems. A range of alternative delivery systems that can introduce RNAi-inducing molecules into cells are also well established, including but not limited to other viral systems (e.g., adenovirus, AAV and lentivirus delivery systems) and other types of stable or transient eukaryotic expression systems (e.g., pCDNA3.1). It is contemplated that these alternative systems find equal use with the invention.

Furthermore, the inhibitory molecule that is expressed by the vector is not particularly limited. The inhibitory nucleic acid molecule can be of any suitable type, including but not limited to an siRNA molecule, an shRNA (short hairpin RNA) molecule, or a shmiRNA molecule that express a longer transcript that encompasses a region that forms a short hairpin.

Improved Methods for Purification of Small DNA Fragments and DNA Hairpins

The REGS procedure (Sen et al., (2004) *Nature Genetics* 36(2): 183-189) involves repeated purification of DNA fragments on acrylamide gels. This is time consuming and often produces poor yield. The invention provides an improved method to selectively purify small DNA fragments with a combination of polyethyleneglycol (PEG) precipitation and ethanol precipitation. PEG has previously been used to size fractionated DNA (Lis and Streif, NAR 2:383 (1975)). However, under the conditions typically described (Hartley and Bowen, *BRL Focus* 18:27; and Paithankar and Prasad, NAR 19:1346 (1991)), where the final concentrations of 10 mM $MgCl_2$ and 1.7-10% PEG 8000 are used, it is not possible to precipitate DNA smaller than 150-200 basepairs.

By increasing the concentration of divalent cation (e.g., $Mg^{2+}$) to 30-100 mM, and the PEG 8000 concentration to up to 30%, a size-selective precipitation of smaller fragments is possible. With the addition of a co-precipitant (e.g., glycogen or linear acrylamide) it is possible to obtain consistent, efficient, precipitation of even small quantities of DNA. For example, at 50 mM $MgCl_2$ and 30% PEG, fragments of 25 base pair and above are efficiently precipitated. At 50 mM $MgCl_2$ and 16% PEG, fragments of 50 base pair and above are efficiently precipitated. At 50 mM $MgCl_2$ and 12% PEG, only fragments larger than 75 base pair are efficiently precipitated. By selecting the final PEG concentration, it is possible to selectively precipitate only DNA larger than the desired cut-off size. If DNA below the cut-off size is desired, then the smaller DNA can be easily recovered from the PEG supernatant, for example by ethanol precipitation.

These novel methods can be used during conversion of cDNA in shRNA inserts. Following ligation of the first hairpin-adaptor oligo, the ligation product is precipitated with 100 mM $MgCl_2$ and 15% PEG. This removes unincorporated oligo, oligo-dimers, and products too short to be useful. After cutting precipitated DNAs with the first enzyme (e.g., EcoP15I, McrBC or MmeI), the DNAs are reprecipitated with 100 mM $MgCl_2$ and 15% PEG. The small DNA hairpins released by the enzymatic cutting will not be precipitated and can be recovered from the supernatant. By adjusting the PEG concentration, a similar approach can be used after ligation of the second loop. Such size-selective precipitation of DNA that improves cloning efficiency is a general purpose method that finds use with the present invention, but it also finds wider use with any cloning protocol where it is advantageous to eliminate unwanted, small unreacted nucleic acid reagents or reaction byproducts.

Alternative Methods for Purifying Synthetic Intermediates

At various stages during the subcloning procedures of the present invention, the desired product is a circular, 'dumbell-shaped' DNA molecule—a region of double-stranded DNA whose ends are 'capped' with a single-stranded loop. See FIGS. 1 and 2. For example a dumbell is formed after ligation of the first hairpin-loop to fragments of cDNA. In some embodiments of the invention, a dumbell is formed when EcoP15I products are ligated to the ends of the prepared vector because the procedure is run using conditions that will allow the vector to dimerize—at the end of the ligation there is thus an EcoP15I-derived hairpin structure on both ends of the vector. Because exonucleases degrade nucleic acids from free 5' or 3' ends, these products are resistant to degradation. However, unligated starting materials, and some undesired byproducts are not circular and can be degraded by using suitable exonucleases.

After ligation of the hairpin-adaptor oligos, a suitable exonuclease or suitable combinations of exonucleases can be added in order to degrade excess oligo and other undesired by-products. Examples of suitable nucleases are Exonuclease I from *E. coli* and Lambda (λ) exonuclease. Exonuclease digestion is an effective alternative to gel purification and/or selective precipitation for the purification of circular or dumbbell-shaped DNA molecules from non-circular molecules.

Under some circumstances wherein one of the DNA molecules to be ligated lacks the 5'phosphate moiety, it is advantageous to perform ligations. The products of such ligations have one intact strand, formed by ligation of the 5'phosphate on one strand to a 3'hydroxyl on another, and one gapped strand, where no ligation could occur due to the lack of a 5'phosphate group. It is advantageous that lambda exonuclease is unable to initiate degradation from nicks or gaps in dsDNA, as dumbell-shaped DNA molecules with a nick or gap in the double-stranded section (as produced by, e.g., ligation of a dephosphorylated hairpin-adaptor oligo and phosphorylated DNA) remain resistant to cleavage. A nick can also be produced by 'blocking' the 3' end instead of removing the 5' phosphate. Suitable blocking can be made by using a 3' phosphate group or a nucleotide analog lacking the 3' OH group.

Reducing Side-Reactions in Order to Improve Efficiency.

During the ligation between the first hairpin-adaptor oligo and cDNA fragments, several side reactions limit the yield of the desired product. The principal ones sources of aberrant products are (i) the formation of hairpin-adaptor oligo dimers, where two molecules of hairpin-adaptor oligo ligate to each other without any intervening cDNA, thus reducing the amount of available hairpin-adaptor oligo, and (ii) ligation between cDNA fragments, which reduces the number of cDNA ends available for ligation to the hairpin-adaptor oligo.

The formation of hairpin-adaptor oligo dimers can be reduced as follows:

(A) The hairpin-adaptor oligo can be dephosphorylated or synthesized without a 5'phosphate. Since neither molecule of hairpin-adaptor oligo would have a 5'phosphate, dimers are unable to form. The desired product between a cDNA fragment and a hairpin-adaptor oligo would form a gapped DNA molecule. The gapped molecule must subsequently be repaired, for example by treatment with polynucleotide kinase to replace the missing 5'phosphate and DNA ligase.

(B) The hairpin-adaptor oligo can be synthesized with a blocked 3' end, for example with a 3' phosphate group or a 3' dideoxy nucleotide, so that the 3' end cannot be ligated. The nick caused by a 3' phosphate group could be repaired by treatment with polynucleotide kinase to remove the 3' phosphate group (and replace the 5' phosphate if it is missing), followed by ligation with a DNA ligase. A nick caused by a dideoxy nucleotide could be repaired by treatment with a proof-reading non-strand-displacing polymerase that excises the dideoxy nucleotide and replaces it with a normal nucleotide. This is also followed by ligation. Optionally, the hairpin-adapter oligo can be treated with polynucleotide kinase prior to ligation.

(C) Alternatively, the hairpin-adaptor oligo can be designed so that ligation of two hairpin-adaptor oligos generates a restriction enzyme site such that digestion with the restriction enzyme regenerates the original hairpin-adaptor oligos. Inclusion of the restriction enzyme in the ligation reaction ensures that any hairpin-adaptor oligo dimers that form are recleaved and are available for ligation to cDNA.

For example, a hairpin-adaptor oligo as shown in FIG. 5A can be synthesized. That oligo has the following double stranded stem:

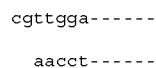

(where ---- represent additional stem-loop DNA of arbitrary sequence).

This example oligo is able to ligate to cDNAs cut with restriction enzymes such as HpaII, HinP1 and Taq1, each of which leave a two base pair "CG" 5' overhang. Formation of a hairpin-adaptor oligo dimer results in the sequence:

```
                                    (SEQ ID NO: 32)
     ------tccaacgttgga------

(SEQ ID NO: 33)
     ------aggttgcaacct------
``` which creates a site for the restriction enzyme AclI (bold). AclI cuts to produce two products identical to the original hairpin-adaptor oligo. Ligation of the hairpin-adaptor oligo to the products of HpaII digestion, HinP1I digestion or TaqI digestion does not generate an AclI site and the product is therefore not cleaved.

Ligation between cDNA fragments can be reduced in similar ways:

(A) The cDNA fragments can be dephosphorylated. This cannot be combined with dephosphorylation of the oligo. However it could be combined with a 3'-phosphorylated oligo. In this case the 5' phosphate of the oligo could be ligated to the 3'-OH of the cDNA but not to the 3' phosphate of a second oligo molecule. The cDNA fragments lack 5' phosphates and cannot therefore ligate to each other.

(B) If a restriction enzyme was used to generate the cDNA fragments, the enzyme can be included in the ligation mixture. Any ligation events between cDNA fragments will regenerate the restriction site and be recleaved. It is often possible to chose the hairpin-adaptor oligo sequence so that ligation between a restriction enzyme generated cDNA fragment and the hairpin-adaptor oligo does not generate a new substrate for the restriction enzyme. For example, ligation of cDNA cut with HpaII digestion, HinP1I digestion or TaqI digestion to the hairpin-adaptor oligo sequence described above does not regenerate the respective sites.

Methods for Controlling the Final Loop Sequence

As described above, the REGS protocol initially attaches a large loop which, after 'opening out' of the hairpin constructs into dsDNA, is subsequently largely removed by BamHI digestion. Because of this, the final RNA hairpin has the sequence:

```
                                    (SEQ ID NO: 34)
     NNNNNNNNNNNNNNNNNNNNNNNNTTGGU (SEQ ID NO: 35)
     NNNNNNNNNNNNNNNNNNNNNNNNNAACCT
``` wherein the Ns represent the cDNA-derived target sequence. The loop produced has a self-complementary sequence that can self-hybirdize to extend the stem of the hairpin. This may have undesirable consequences on the subsequent processing of the hairpin by Dicer.

It is possible to design a hairpin-adaptor oligo that, after 'opening out' and digestion with an appropriately selected restriction enzyme or enzymes, recircularises resulting in a final loop of almost any length and sequence. This novel method provided herein is not restricted to use with hairpin-adaptor oligos. It can also be applied to any dsDNA sequences that can be excised to leave behind a remaining sequence of almost any length and nucleotide composition.

The essential feature of the hairpin-adaptor in this system is that it includes two restriction enzyme recognition sites for enzymes that cut outside their recognition sequences, and which can produce compatible overhangs. Examples of such enzymes include: GsuI, BpmI, BpuE1, BsgU, AcuI or Eco57I sites, or any combination of one of each of those sites. Or any combination of one of those sites and a BsrDI site, a BstF5I site or a BtsI site. The placing of these sites within the hairpin-adaptor oligo determines the length of the final loop, while the sequence is determined by other portions of the adaptor oligo. For example an oligo of the general structure as shown in FIGS. 5B and 5C can be used to generate an eight base pair loop of any sequence. This oligo is designed to be ligated to a DNA product carrying a two base pair overhang of any sequence XY. X' and Y' represent the complements of X and Y respectively.

In this oligo, there is a BpmI site (italics) and a BtsI site (bold). N', X' and Y' refer to the complementary base to N, X, Y respectively and (N)n represents any sequence of any length.

After conversion to dsDNA and cloning into a vector, the sequence becomes:

```
I---------SEQ ID NO: 36------I    I-------SEQ ID NO: 38-----I
... X Y^NNNNNNNNNY'X'CACTCTCCAG-(N)n-GCAGTG X YSNNNNNNNNY'X'...

...^X'Y'NNNNNNNNX Y GTGAGAGGTC-(N)n-CGTCACSX'Y'NNNNNNNNY X ...
I---------SEQ ID NO: 37------I    I-------SEQ ID NO: 39-----I
```

Cutting with BpmI cuts at the positions marked ^, while BtsI cuts at the positions marked §. After cutting and recircularisation the sequence is:

```
                                    (SEQ ID NO: 40)
     ... X Y NNNNNNNNN Y' X'...
``` where the N's can be any sequence.

Note that X, Y above match the sequence to which the oligo was ligated, i.e., they are part of the target sequence. In the case of a blunt-ended target, X and Y would be determined by the hairpin-adaptor oligo's sequence. The sequence is not particularly limiting, but it must base pair X to X' and Y to Y'. As a result, for the specific case of a blunt-ended target, the target hairpin stem is increased by two basepairs. This can be avoided by choosing an enzyme pair that cleaves to produce a two basepair 3' overhang (all of the enzymes listed above are suitable). After cleaving with the enzyme pair, the ends of the DNA are treated with Klenow, T4 DNA polymerase, or an enzyme comprising a similar activity to remove the 2-base pair 3' overhangs. The DNA is then recircularised as above.

A site for an infrequently cutting restriction enzyme (e.g. PmeI, NotI, AscI, AsiSI, PacI, SapI, SwaI or others) can be included within the portion of the adaptor-oligo that is excised during the above procedure. (e.g. within the sequence labelled (N)n). The presence of such a restriction site can be useful in reducing background colonies arising from transformation with DNA in which deletion of the intervening loop sequences has failed. The infrequently cutting restriction enzyme can be used to linearize any such background DNA, rendering it unable to transform *E. coli*.

Figure 6:
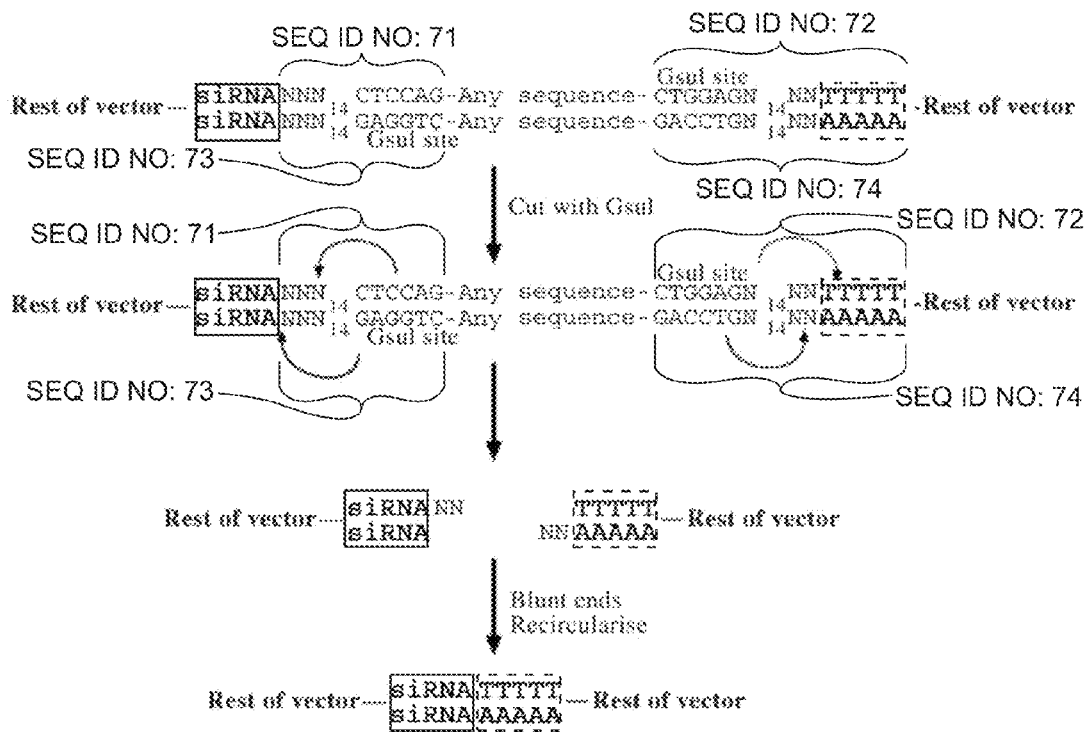
FIG. 6 provides an illustration demonstrating a general method that allows the precise removal of a stuffer fragment without requiring any specific sequences in the regions flanking the stuffer.

A similar strategy using pairs of restriction sites as above can be used to design a multiple-cloning site/stuffer that can be precisely removed d, for example to remove restriction enzyme sites introduced to simplify cloning (FIG. 6). An example application of this is in the cloning of shRNA constructs to U6-promoter driven vectors. The termination signal for RNA polymerase III is a sequence of 4 or more (preferably 5 or more) T residues. To express a proper shRNA molecule, these T residues must occur immediately following the end of the sequence that will form the hairpin stem. It is common when cloning to include restriction enzyme sites on the ends of the pieces of DNA that one is cloning. However in a case such as the above, the added restriction sites would intervene between the end of the hairpin and the TTTTT sequence. As illustrated in FIG. 6, pairs of GsuI sites (or similar pairs of sites as listed above) can be used to remove extra sequences added to aid cloning.

Replacement of MmeI with Alternative Restriction Enzyme Sites

The endonuclease MmeI used in the original REGS protocol is unusual in that it cuts 20/18 nt outside its recognition site, producing products with two basepair 3' overhangs. Twenty (20) nucleotides of matching sequence is at the lower end of the length requirement for effective siRNAs. Because of this, the MmeI site must be placed right at the end of the hairpin-adaptor oligo. In the original REGS procedure, the last basepair of the MmeI site is actually provided by the cDNA. This produces final constructs with 21 nt of targeting sequence, at the expense of requiring the cDNA fragments to carry a guanosine (G) at the 3' end. The method of preparing the cDNA fragments and ligating on the hairpin oligonucleotide further requires the second last base to be C. This requirement reduces the number of potential siRNA sequences that can be produced from each gene, reducing the diversity of the library.

A second disadvantage with using MmeI is that it produces a two base pair 3'-overhang. If this is removed (e.g., with the Klenow fragment of DNA polymerase I), then the final targeting siRNA products are 2 base pair shorter which is undesirable. If they are left intact, then the second hairpin-adaptor oligo must be designed with a complementary two base pair 3'-overhang. The 3'-overhangs produced by MmeI will be of unpredictable sequence so that the second hairpin-adaptor oligo must be prepared as a mixture of all 16 possible two base pair 3'-overhangs. This reduces the effective concentration of ligation partners, reducing the yield at this step.

Use of a restriction enzyme that cuts further from its recognition site than MmeI is an improvement to the REGS protocol because it allows more flexible positioning of the restriction site within the first hairpin-adaptor oligo, and can generate a longer final targeting construct. In many cases shRNAs of 22-30 base pairs have been shown to be be more effective at triggering RNA interference than shorter oligos. Furthermore, with more matching DNA to work with, it is possible to perform the ligation of the second hairpin-adaptor oligo with substrate DNA which has been made blunt-ended.

As an example, the restriction enzyme EcoP15I has features that make it a desirable replacement for MmeI. EcoP15I cuts 25/27 nt outside its recognition site, producing products with a two base pair 5' overhang. This overhang can be 'filled in' with a suitable polymerase (e.g. T4 DNA polymerase) producing a blunt-ended product with up to 27 nt of sequence derived from the target cDNA.

An example of a suitable EcoP15I-based hairpin-adapter oligo is shown below.

(SEQ ID NO: 41)
CTGCTGGATCCAGAGATGAGAGTTTTTGTTTAATCTCCAGTTTAAACAA

AAACTGGAGTCTCTGGATCCAGCAG

Figure 9:
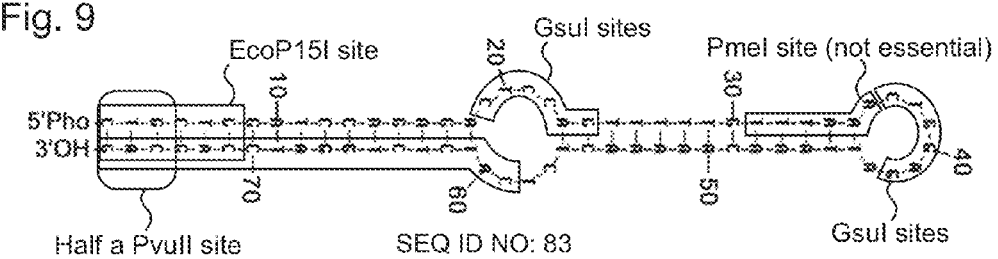
FIG. 9 provides an illustration of a loop adapter sequence and secondary structure. This figure shows loop adapter A, which is an EcoP15I-based loop adaptor primer (DK308), showing the predicted secondary structure and the positions of essential and optional sequence elements. Much of the sequence is arbitrary. The GsuI and PmeI sites are only functional after the loop has been opened out. The GsuI sites can be used (as in FIG. 6) to remove unwanted sequences within the loop. Following GsuI treatment, the final loop sequence is determined in this case by the yellow highlighted bases. The only bases in this sequence that cannot be varied are those that are part of the EcoP15I site. The length of the final loop can be controlled by changing the position of the right-hand GsuI site compared to the 3' end of the oligo.
Figure 10:
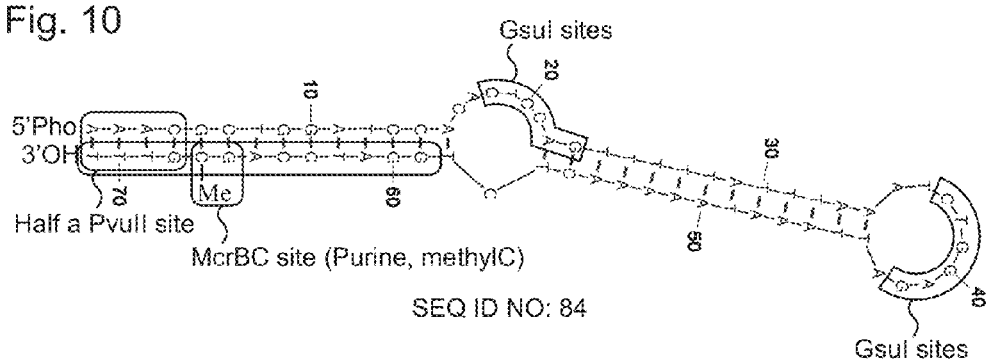
FIG. 10 provides an illustration of a loop adapter sequence and secondary structure. This figure shows loop adapter B, which is an McrBC-based loop adaptor primer showing the predicted secondary structure and the positions of essential and optional sequence elements. An alternative hairpin oligo for using McrBC instead of EcoP15I. There are very few constraints on the hairpin oligo sequence because the McrBC site is so short. The length of the final hairpins can be adjusted by moving the McrBC site 5' or 3'. In this oligo, PmeI was arbitrarily chosen as the enzyme to re-cut hairpin dimers, instead of PvuII. The final loop sequence is determined in this case by the highlighted bases. The length of the final loop can be controlled by changing the position of the right-hand GsuI site compared to the 3' end of the oligo.
Figure 11:
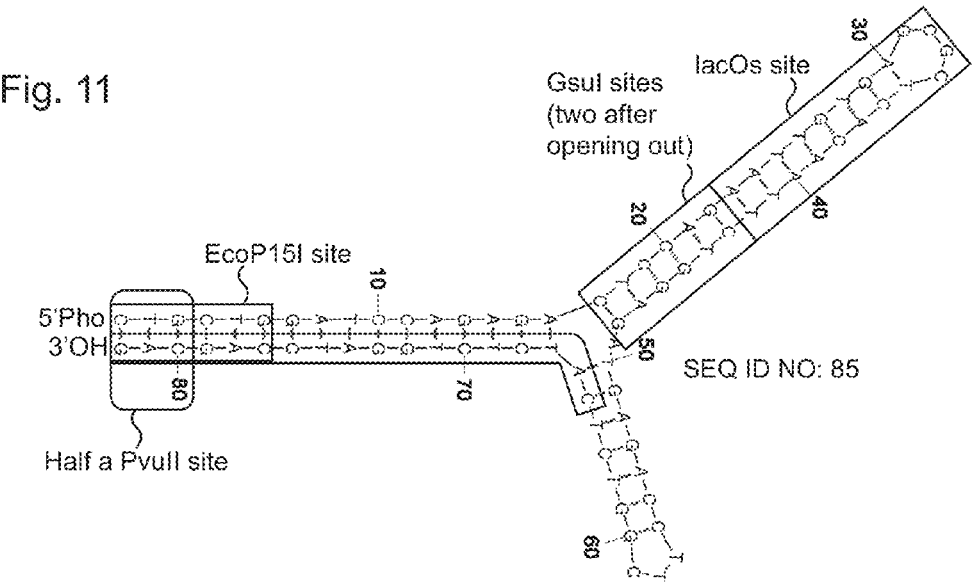
FIG. 11 provides an illustration of a loop adapter sequence and secondary structure. This figure shows loop adapter C, which is an EcoP15I-based loop adaptor primer incorporating a single binding site (lacOs) for the bacterial repressor lacI. Much of the sequence is arbitrary. There are two GsuI sites after the loop is opened out. The final loop sequence is determined in this case by the highlighted bases. The only bases in this sequence that cannot be varied are those that are part of the EcoP15I site and the lacO site. A second (or even third) lacO site could be easily accommodated. The length of the final loop sequence can be varied by moving the second GsuI site relative to the 3' end. This can be achieved by varying the length of the side stem-loop (50-66).
Figure 12:
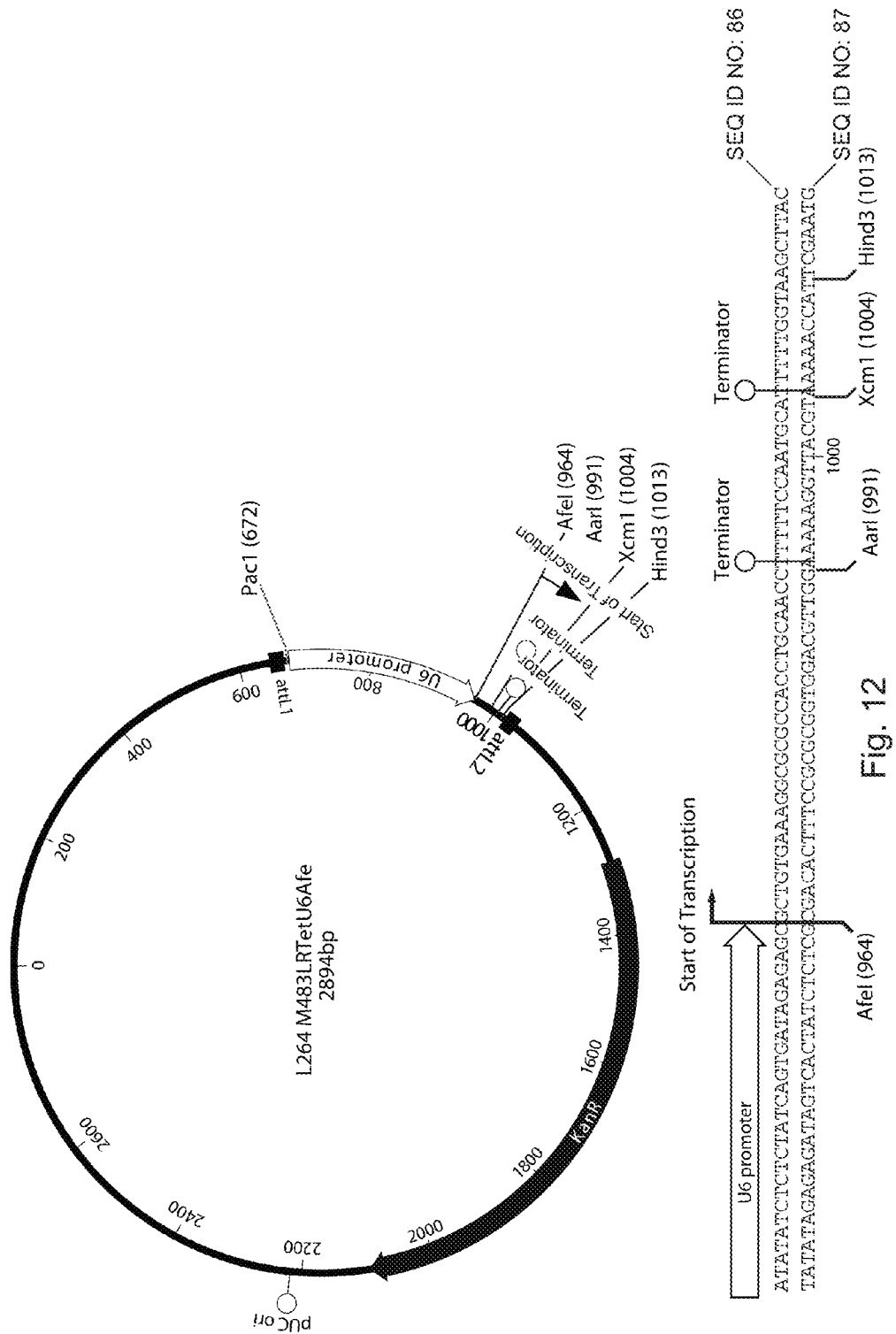
FIG. 12 provides an illustration of a vector for the intermediate cloning of short hairpin RNAs under the control of the U6 promoter. In this case the U6-promoter and cloning site are flanked by Gateway recombination sites and PacI/HindIII restriction enzyme sites to facilitate cloning of the completed cassette into the final vector. Similar vectors can be used to clone the short hairpin RNAs as part of a transcript including a microRNA or downstream of different promoters. The key feature of these vectors is that they contain restriction enzyme sites that (following optional blunt-ending) produce a vector with blunt ends corresponding precisely to the desired junction between the vector and the hairpin construct. In this case AfeI provides a blunt end at the start of transcription, whereas XcmI or AarI followed by blunting with a suitable polymerase produce a blunt end immediately preceding the termination signal (TTTTT) for RNA polymerase III.
Figure 13:
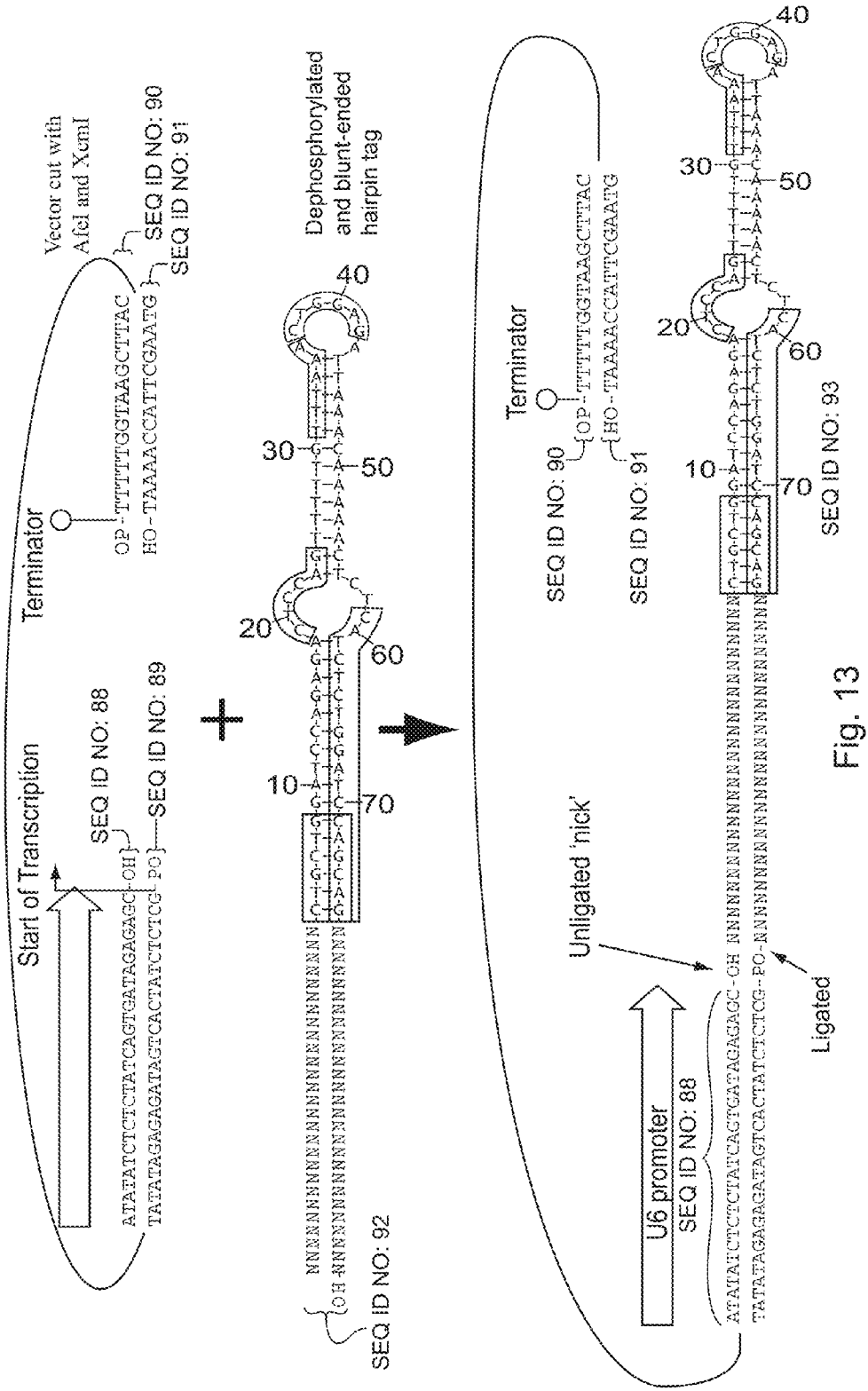
FIG. 13 provides an illustration of a vector for the cloning of the hairpin tag released by EcoP15I (or McrBC), and utilization of the "opening out" method described in FIG. 1. Dimerisation/recircularisation of the vector is inhibited by including AfeI in the ligation reaction and by the single base overhang at the terminator end of the vector. Because the haripin tag lacks a 5' phosphate, the ligation product with have a 'nick' in the DNA phosphate backbone as indicated. PO=5' phosphate; OH=3' hydroxyl group.
Figure 14:
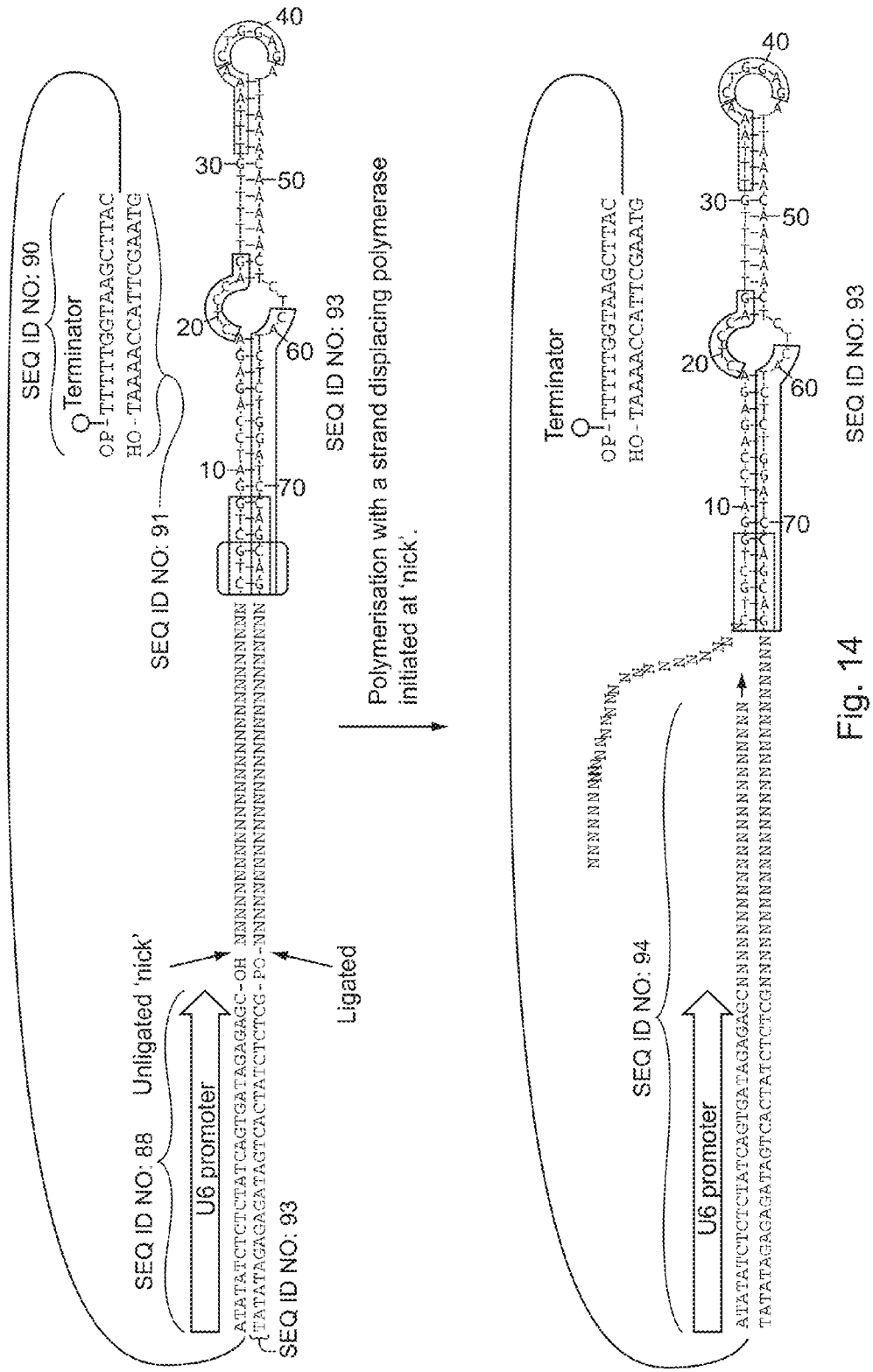
FIG. 14 provides an illustration of a vector construction of the invention. A strand displacing polymerase that is able to initiate at a nick in the DNA (e.g. DNA polymerase I Klenow fragment or Bst polymerase) is used to copy the hairpin structure into double-stranded DNA. Polymerisation initiates at the nick generated in the previous ligation step.

Additional examples of hairpin oligonucleotides of the inventions are provided herein, for example, see FIGS. 5A-5C and 9-11. As shown in FIGS. 9-11, these oligonucleotides can optionally contain (in addition to the EcoP15I site):
(A) two GsuI sites positioned such as to be useful in removing excess oligo sequences as discussed above;
(B) PmeI site useful for linearising DNA that has escaped cutting with GsuI, as described above; and
(C) a BamHI site within the retained loop sequence, that is useful for one method of recovering active siRNA sequences from cell populations (see below).

A second option for replacing MmeI is the use of McrBC. This enzyme complex cleaves between a pair of copies of its half-site RmC (a purine (G or A) followed by a methylated cytosine). Cleavage occurs approximately 30 base pairs from one or other of the half-sites. Typically hairpin-adaptor oligos are ligated to both ends of a target DNA fragment, so that if each hairpin-adaptor oligo contains one half-site then the product of ligation will contain two half-sites and be a substrate for cleavage. Note that only one end of the target DNA will be cleaved under these circumstances. Following cleavage with McrBC the DNA ends are undefined (unknown whether blunt or with a 5' or 3' overhang). The ends can be repaired by treatment with Klenow DNA polymerase or T4 DNA polymerase or another DNA polymerase plus dNTPs. Because the recognition sequence for McrBC is very short, there are correspondingly fewer constraints on the sequence of the hairpin-adapter oligo.

The methylated cytosine (5-methylcytosine or 5-hydroxymethylcytosine or N4-methylcytosine) can be introduced during chemical synthesis of the hairpin-adapter oligo. Note that cloning of sequences containing methylated cytosine requires the use of a bacterial strain lacking the native *E. coli* restriction systems. An example of such a strain is the NEB strain ER1793.

An example of a suitable McrBC-based hairpin-adaptor oligo for use in cloning to blunt end DNA fragments is shown below. This adaptor includes two GsuI sites (bold) positioned such as to be useful in removing excess oligo sequences as described above. A PmeI site (italic) useful for linearizing DNA that has escaped cutting with GsuI, as described above. With the GsuI sites positioned as shown, the final loop will have the underlined sequence (or the reverse-complement of the underlined sequence, depending on subsequent cloning strategy) if the GsuI overhangs are removed before recircularization. The exact position of the methylated C (*C) can be varied, to give hairpins of different lengths. For an example of a hairpin oligonucleotide containing a methyl-C, see FIG. 10.

SEQ ID NO: 42
Y'X'<u>NGCNNNNNNNNNNNNNN</u>XYNNNNNNNNNNNNNNNCTCCAG*TTTAAAC*

NNNNNCTGGAGNNNNNNNNNNNG*CNXY

A second more specific example (in which the relative positions of the GsuI sites has been exchanged) is provided below:

SEQ ID NO: 43
GTGTGCTGGATCCACACTCCAGTTTTTGTTTAAACTGGAGATTAAACAA

AAACTCT<u>GGATCCAG*CACAC</u>

An example of a suitable McrBC-based hairpin-adaptor oligo for use in cloning to DNA fragments with a two base pair 5' GC overhang is shown below. This could easily be modified to match the overhang produced by other restriction enzymes. This adaptor includes two GsuI sites (bold) positioned such as to be useful in removing excess oligo sequences as in 4) above. A PmeI site (italic) useful for linearising DNA that has escaped cutting with GsuI, as described above. With the GsuI sites positioned as shown, the final loop will have the underlined sequence.

SEQ ID NO: 44
CG<u>NNNGC</u>NNNNNNNNNNNNNNNCGNNNNNNNNNNNNNNNNCTCCAG*TTTAAAC*

NNNNNCTGGAGNNNNNNNNNG*CNNN

Improvements to Hairpin-Adaptor Oligo 2 and the Mechanism for 'Opening Out' the Hairpins.

The method described in the REGS procedure uses the Phi29 polymerase to simultaneously 'open out' and amplify the shRNA cassettes by rolling-circle amplification. Unfortunately this method can lead to a highly biased library because Phi29 is extremely processive. As a result, shRNA cassettes that are first to be amplified will continue to be further amplified at the expense of amplification of cassettes which have not yet even been 'opened out'. Indeed, it would be preferable to avoid even using conventional PCR to amplify the cassettes in order to minimize library bias. With sufficiently efficient early steps, enough material is available at this stage to remove the need for amplification entirely, or reduce the need to a small number of cycles.

The invention provides several improvements to the existing methods:

(A) The hairpin-adaptor oligo 2 is a mixture of 16 different oligos each with a different one of the 16 different possible two base pair 3'-overhangs. This allows the hairpin-adaptor oligo 2 to be ligated to any of the 16 possible two base pair 3' overhangs produced by MmeI digestion. However, it also results in a reduced ligation efficiency because only a small fraction of the ends present in the reaction are compatible with each other. The two base pair overhang can be removed from the products of MmeI digestion by T4 DNA polymerase or Klenow-fragment DNA polymerase (or similar polymerases). This would allow them to be ligated to a blunt-ended hairpin-adaptor oligo 2. However, removal of the two base pair overhang from an MmeI product reduces the total length of the target-matching hairpin to just 19 base pairs, which is below the optimum range of lengths so this approach is not recommended.

However, if EcoP15I or McrBC (or another enzyme that cuts further from its recognition sequence than MmeI does) is used in place of MmeI (as described elsewhere) then after T4 DNA polymerase (or Klenow etc) treatment of the DNA, the target-matching hairpin is still long enough. In fact, because EcoP15I produces a 5' overhang instead of a 3' overhang, the ends will be "filled in" and no target-matching sequence is lost at all. Thus, when alternative restriction enzymes to MmeI are used the hairpin-adaptor oligo 2 can be simplified to be a blunt-ended adaptor molecule.

(B) For the "opening out" reaction it is preferable to use a DNA polymerase with strand-displacing activity so that the polymerase is not blocked by the hairpin structure. Suitable polymerases include Bst polymerase, Vent polymerase, Vent (exo-) polymerase and many others, but not Taq DNA polymerase.

(C) Where amplification is required it is preferable to replace hairpin-adaptor oligo 2 with a "Y" shaped adaptor molecule as described in Kaur and Makrigiorgos (2003), NAR 31:e26. The Y-shaped adaptor can be produced by annealing two oligos of appropriate sequence, for example:

```
5'ACGTCGACTATCCTTGAACAGTG
                        CCAGTGACGGAAGATCTCCNN3' SEQ ID NO: 45

GGTCACTGCCTCAGAGAGG5'  SEQ ID NO: 46
3'GAGTTGACGTAGAGTTACGTGTG
```

Alternatively, the Y-shaped adaptor can be produced from a single hairpin-oligo containing two Uracils in the loop. Treatment with the enzyme Uracil-DNA glycosylase and heating, treatment with USER™ enzyme from New England Biolabs, or treatment with similar enzymes leads to formation of a break in the DNA chain at the two Uracils producing a Y-shaped adaptor. For example the oligo:

(SEQ ID NO: 47)
```
 ACGTCGACTATCCTTGAACAGTG
U                        CCAGTGACGGAAGATCTCCNN3'
U                        GGTCACTGCCTCAGAGAGG5'
 GAGTTGACGTAGAGTTACGTGTG
``` after processing with USER™ enzyme produces exactly the same Y-shaped adaptor as above.

The un-basepaired ends of the Y-shaped adaptor are ideal for annealing primers. The primers can then be extended by a strand-displacing DNA polymerase to "open out" the hairpin construct. The double-stranded product can be further amplified by cycles of denaturation, primer annealing and extension (i.e., by PCR) but it should be noted that the double-stranded product does not have un-basepaired ends and will therefore be at a slight competitive disadvantage for primer annealing compared to the un-opened-out hairpins. Thus any hairpins that were not opened-out during the first polymerase extension step will be opened-out in preference to amplification of other hairpin constructs. This helps to minimize bias in the library.

(D) It is possible to omit one of the un-basepaired arms of the Y-shaped adaptor. In this case, the first round of "opening up" will produce one molecule of product instead of two, and only one primer is required. For example the above oligos can be modified to:

```
    5'CCAGTGACGGAAGATCTCC3' SEQ ID NO: 48
    GGTCACTGCCTCAGAGAGG5'   SEQ ID NO: 49
3'GAGTTGACGTAGAGTTACGTGTG and GCAGTTGAGUU
  T              CCAGTGACGGAAGATCTCC3'        SEQ ID NO: 50
  A              GGTCACTGCCTCAGAGAGG5'
     GAGTTACGTGTG
```

(E) Any of the above designs of adaptors can be modified with a 3'-phosphate to prevent adaptor dimerization, as described previously. After ligation, the resulting nick can be repaired by treatment with T4 polynucleotide kinase to remove the 3'-phosphate (and replace any possibly missing 5'-phosphates) and treatment with a DNA ligase. Alternatively the adaptor can be blocked at the 3' end with a dideoxy nucleotide. In this case repair requires treatment with a proof-reading non-strand-displacing polymerase, to excise the dideoxy nucleotide and replace it with a normal nucleotide (followed optionally by PNK treatment) and then ligation.

sequence of the loop of the expressed shRNA. Cassettes inserted in one orientation will have one loop sequence whereas cassettes cloned in the other orientation will have the reverse-complement loop sequence.

If one of the alternative enzymes to MmeI has been used then there is an alternative to using MlyI, as follows. This example uses hybridized, single-arm oligos as in 3) above, with a blunt end. However it is equally applicable to hairpin-adaptor oligos with or without a UU sequence or to y-shaped adaptors or to adaptors with a 5' NN overhang (to anneal to un-blunted EcoP15I products).

Consider the following oligo adaptor:

```
                    5'CAGAGTCGGTCTCAGATCTCC*3' SEQ ID NO: 50

GGGTCGCCTATTGTTAAAGTGTGTCCTCAGTCAGCCAGAGTCTAGAGG-   SEQ ID NO: 51
            P5'
```

(F) The 'stem' of hairpin-adaptor oligo 2 and the above Y-shaped adaptors is not a perfect duplex, it contains a three base pair mismatch. This is done because the REGS cloning strategy for the shRNA cassettes requires that they be cut with MlyI to produce a blunt-end exactly at the end of the target hairpin at one end, and with BglII to provide a sticky end at the other end. This mismatch reduces the efficiency with which T4 DNA ligase is able to ligate the adaptor to the hairpin construct. The mismatch can be avoided in two ways:

The C* at the 3' end of one of the oligos represents a dideoxy C, or a C carrying a 3' phosphate group. In either case, T4 DNA ligase is unable to ligate to this base. Alternative DNA modifications resulting in a ligation-resistant 3' end could be used in the same way. The P at the 5' end of the other oligo represents a 5' phosphate group.

When ligated to the blunted product of the EcoP15I digest (which can be optionally dephosphorylated to discourage dimerisation) a phosphodiester bond will form on only one strand, leaving a 'nick' on the other strand:

```
                              I---SEQ ID NO: 53---I
                            5'CAGAGTCGGTCTCAGATCTCC NNNNNN..

GGGTCGCCTATTGTTAAAGTGTGTCCTCAGTCAGCCAGAGTCTAGAGG-NNNNNN..
            I----------------SEQ ID NO: 54----------------I
```

The adaptor sequence can be modified to be a perfect match to MlyI on both strands. In this case, the final shRNA cassette will be released by MlyI digestion alone as a blunt-ended product, whose ends correspond exactly to the On "opening-out" of this product, the polymerase will reach the nick and 'fall off' as there will be no further template left to copy, thus producing a blunt-end that precisely corresponds to the end of the target-matching DNA:

```
            I------------------SEQ ID NO: 55-----------  ---------I
            CCCAGCGGATAACAATTTCACACAGGAGTCAGTCGGTCTCAGATCTCCNNNNNN....NNNNNN

GGGTCGCCTATTGTTAAAGTGTGTCCTCAGTCAGCCAGAGTCTAGAGGNNNNNN....NNNNNN
``` end of the target-matching region. This cassette can be cloned into a vector that has been modified to accept a blunt-ended cassette. The cassette will be cloned randomly in one of two possible orientations. Because of its origin as a hairpin, the only difference this will make is in the This can then be digested with (in this case) BglII, to produce the final cassette ready to clone. If the EcoP15I digestion products were dephosphorylated, treatment with T4 polynucleotide kinase can be used to restore the missing 5' phosphate:

```
5'P-GATCTCCNNNNNNN....NNNNNNN SEQ ID NO: 58

AGGNNNNNNN....NNNNNNN-P5' SEQ ID NO: 59
```

This approach has the additional advantage that the adaptor oligos cannot form self-dimers because the blocked 3' end cannot be participate in ligation reactions. A small disadvantage of this approach is that it prevents PCR-amplification of the cassette.

(G) Ligation to the second adaptor oligonucleotide, and the subsequent cloning of the opened-out cassette can be combined into a single step if a suitably cut vector is used in place of the second adaptor oligonucleotide. See FIG. 1. In order to allow the 'opening-out' of the hairpin construct ligated to the end of the vector, it is necessary to introduce a 'nick' in the DNA 5' to the 5' end of the hairpin construct. This can easily be achieved by dephosphorylating the hairpin construct prior to ligation, or including a site for a nicking endonuclease (e.g. N.BstNB I; New England Biolabs) in the vector. Transcription initiating at this nick and using a strand displacing DNA polymerase is then used to 'open-out' the hairpin. Recircularization of the vector (after optional further digestion with restriction enzymes) completes initial cloning of the hairpin cassette.

Figure 8:
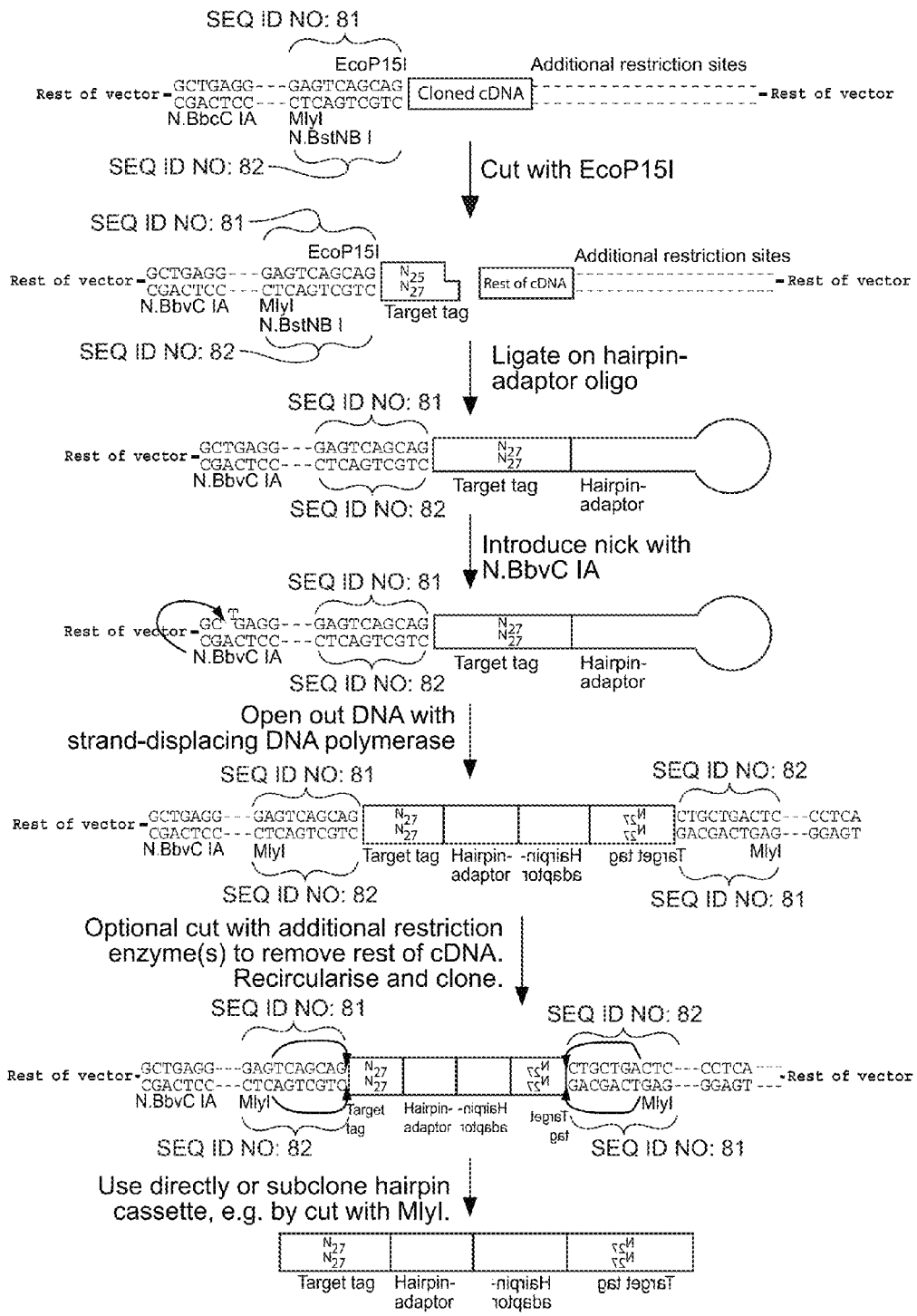
FIG. 8 provides an illustration of a method for the production of shRNA cassettes from a target cDNA while the target cDNA is covalently attached to a vector, thus avoiding the handling/purification of small DNA molecules. This example produces an shRNA cassette from one end of a cDNA fragment cloned into a vector. A simple modification allows production of two shRNAs, one from each end of the cDNA.

(H) Production of shRNA cassettes can also be performed with all intermediates covalently attached to a vector, avoiding problems with handling and purifying small fragments. The target cDNA (or fragments of the target cDNA) must first be cloned into a suitably designed vector. The procedure (outlined in FIG. 8) produces a single hairpin cassette from each insert. Diversity can be obtained by either (1) cloning many different small fragments of the target cDNA into the vector or (2) performing unidirectional nested deletion on the target cDNA cloned into the vector, e.g., using ExoIII/ExoVII deletion or a similar method; Erase-a-Base® (Promega). The vector can be easily adapted for this purpose, for example by introducing suitable restriction sites between the EcoP15I site and the cloned cDNA. A short tag of target cDNA sequence is cleaved off with EcoP15I, and (after optional blunt-ending) a hairpin adaptor oligo ligated onto the end. The remainder of the cDNA can be removed at this stage, or during any of the subsequent steps using the additional restriction sites provided in the vector downstream of the cloned cDNA. The sequence of the hairpin adaptor oligo can be freely chosen, and may include useful features described here such as a pair of GsuI sites, a lacO sequence, a half-restriction site for recleaving of adaptor dimers etc. In order to 'open-out' the loop just formed, a nick is introduced within the vector upstream of the hairpin construct. An example of a suitable enzymes is N.BbvC IA (New England Biolabs, as illustrated in FIG. 8) or Nb.BsrDI. The hairpin construct is opened-out with a strand displacing polymerase as described above. The completed hairpin cassette can then be used directly, or cloned by recircularising the vector and introducing into suitable host cells (e.g., E. coli).

Figure 7A:
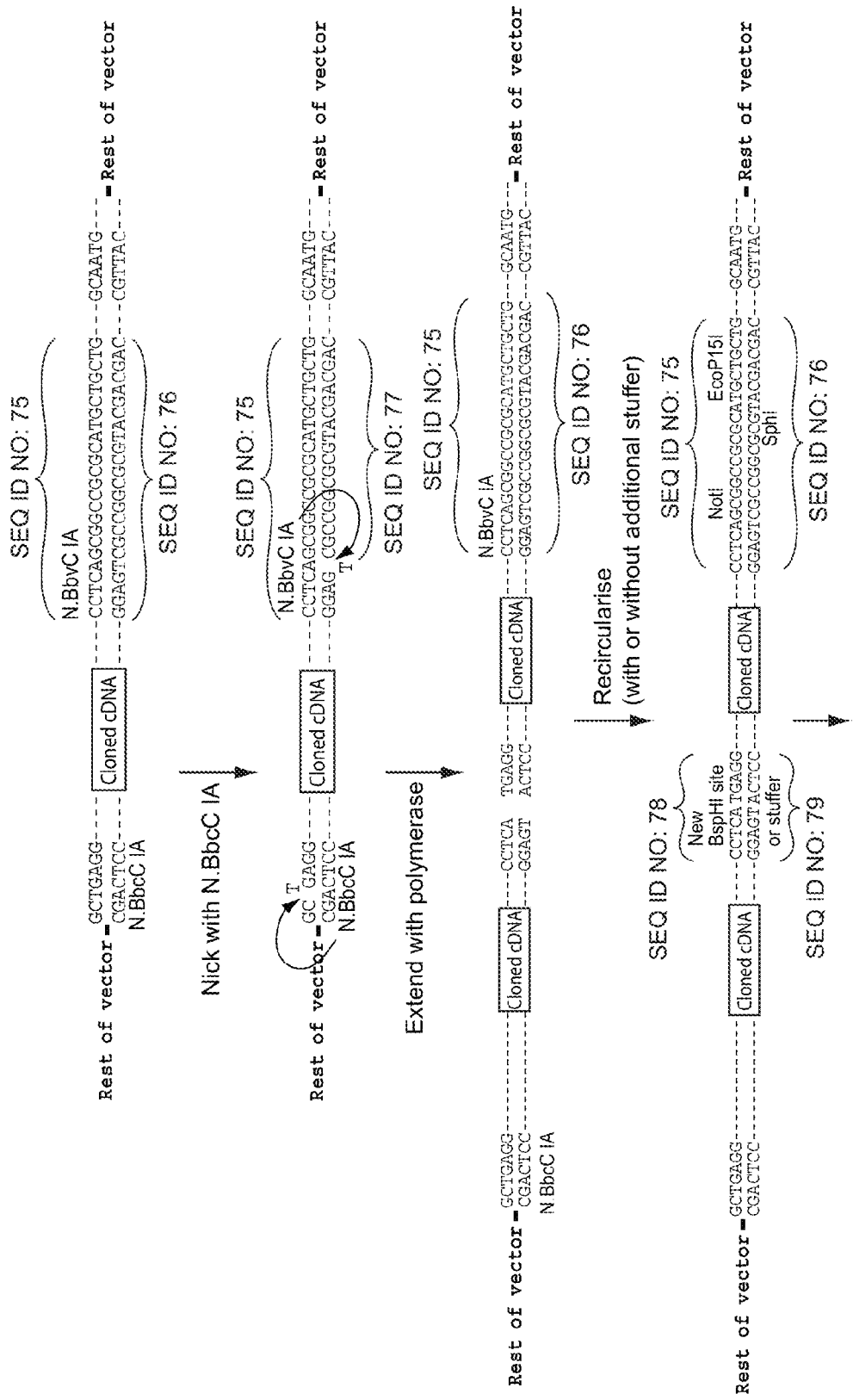
FIGS. 7A and 7b provide an illustration showing a method for making a library of shRNA cassettes within the same vector as an intact copy of the target gene. The target cDNA is first duplicated and then one copy is processed into shRNA cassettes while still attached to the vector (see FIG. 8). This method allows for the production of a single vector that would express both the FACS-reporter for the cDNA and a candidate shRNA for that target.
Figure 7B:
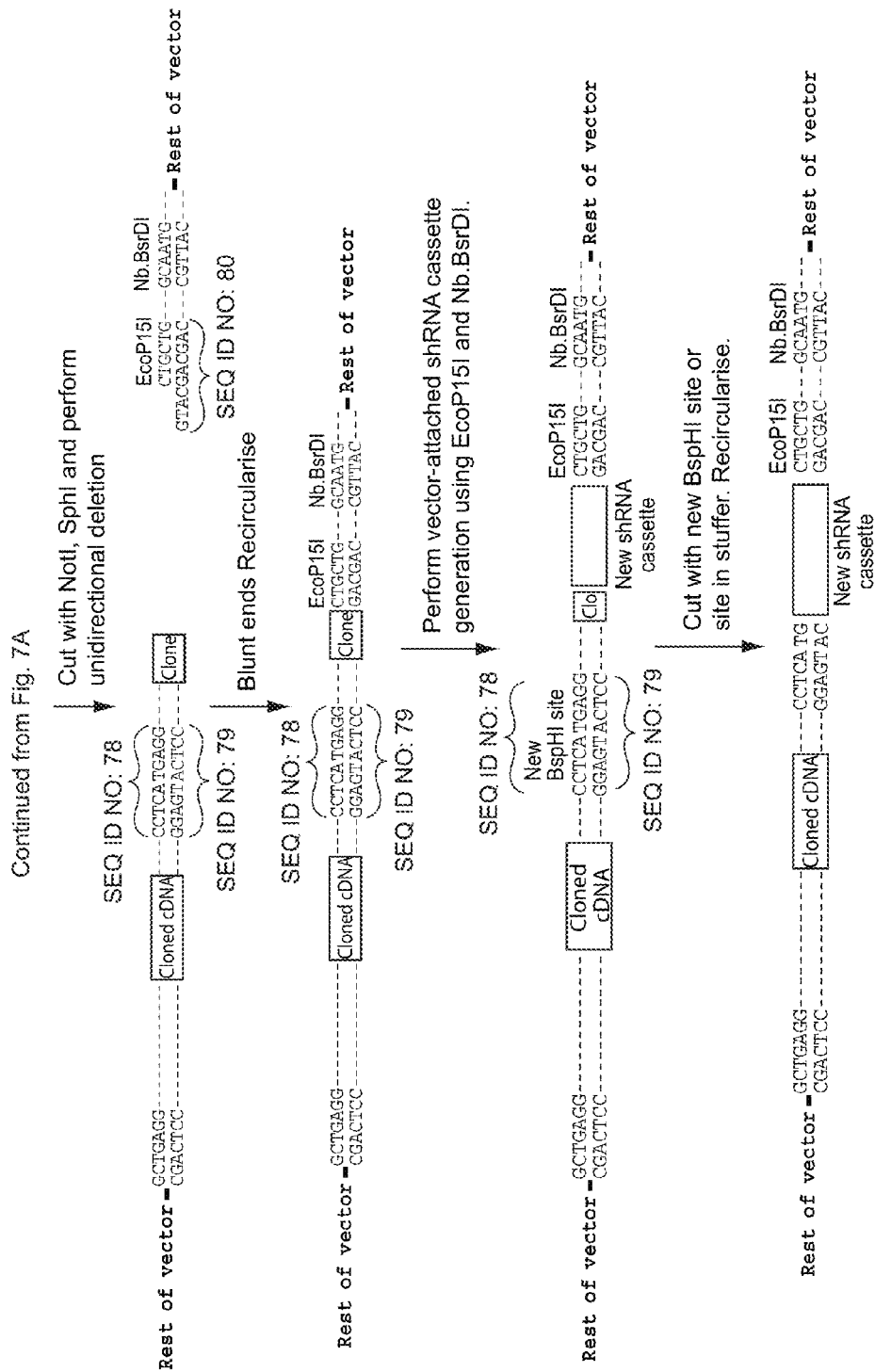

(I) A modification of (H) above allows the production of shRNA hairpin cassettes covalently associated with an intact copy of their target cDNA. This could for example be useful in the parallel identification of active shRNA cassettes against many target genes using our FACS assay if the intact copy of the target gene forms part of one of the reporter constructs we describe. The physical connection between the target cDNA and the shRNA cassette ensures that each cell in the assay contains the appropriate reporter construct for the candidate shRNA construct being tested. In the procedure outlined in FIG. 7, the target cDNA is cloned into a suitably designed vector such that it is flanked by sites for nicking endonucleases such as N.BbvC IA. Following nicking of the DNA, copying of the DNA, starting at each nick, with a strand displacing DNA polymerase leads to duplication of the target gene sequence. The vector can then be recircularised, with or without the cloning of additional ('stuffer') sequences. One of the two copies of the target gene may then be subjected to unidirectional nested deletion and vector-attached generation of shRNA cassettes as described in (H).

Identifying Effective shRNA Cassettes by FACs Analysis

The present invention provides a sensitive and general purpose method for assaying the effectiveness of shRNA cassettes against individual targets. In these methods, the target cDNA is cloned in the same transcription unit as a reporter gene in such a way that the reporter gene will be translated but the target cDNA will not. Example reporter genes include fluorescent proteins such as GFP or enzymes such as luciferase, β-galactosidase or cell surface molecules such as Lyt2 or other molecules whose levels can be determined, for example, by FACS analysis. The reporter gene can be modified by the addition of a protein domain, e.g., a PEST domain, that decreases the stability of the reporter gene in order to increase its turnover.

The reporter-gene target-gene transcription unit is introduced into a suitable cell line, for example using a retroviral vector, and cells expressing the reporter gene target-gene transcription unit are purified by selection and/or by FACS sorting.

The RNAi triggers to be analyzed are introduced into the cells expressing the reporter gene target-gene transcription unit, for example using a retroviral vector expressing a shRNA cassette from the U6 promoter or by transfection of synthetic siRNA molecules. Effective RNAi triggers will recognize mRNA transcripts encoding their target gene and lead to destruction (or blocking of translation) of the mRNA transcript. Because the reporter gene is on the same transcript, translation of more reporter gene will be blocked. The level of reporter gene present will therefore drop, and this can be measured for example by FACS analysis. A population of cells containing effective RNAi triggers can be identified by their low level expression of the reporter gene, and sorted from cells containing ineffective shRNA cassettes on this basis using the FACS.

The assay can also include:

(A) a second reporter gene carried in the same vector as the reporter-gene target-gene transcription unit but expressed in an independent transcription unit. Expression of this reporter gene should be independent of an effective RNAi trigger against the target gene. Such a second reporter gene provides a useful control.

(B) another reporter gene carried in the same vector as the shRNA cassette. This allows cells carrying an shRNA cassette to be distinguished from cells not carrying an shRNA cassette, providing a useful control.

In some cases the reporter gene can be replaced by a selectable marker. For example a negatively-selectable marker such as tk, hprt or aprt. In the case of a negative selectable marker, cells carrying an effective shRNA cassette will not express the marker and will survive selection. This method allows selection of effective shRNA cassettes without using the FACS.

One embodiment of the above system expresses a fusion between GFP, a PEST domain, foot and mouth disease virus peptide 2A and Hygromycin phosphotransferase (GFP-PEST 2A HPT) from a retroviral promoter. The target gene is cloned downstream of the stop codon of hygromycin phosphotransferase but within the same transcription unit. GFP-PEST 2A HPT is processed co-translationally into GFP-PEST (a rapidly degrading version of green fluorescent protein) and 2A Hygromycin phosphotransferase (which confers resistance to the antibiotic Hygromycin B). The co-translational processing is an intrinsic feature of the 2A peptide sequence.

Fluorescence activated cell sorting is especially well suited for use in methods of the invention that can identify RNAi trigger molecules and generate a hypomorphic series of RNAi trigger molecules. This is because FACS analysis is quantitative, where the FACS quantitation directly correlates to gene expression. FACS can be gated to different levels to allow sorting of cells that express different levels of a reporter, thereby identifying RNAi trigger molecules that downregulate a target gene to varying degrees.

Methods for Identification of Lethal Hits

In many genetic screens, the phenotype of interest results in the death of the organism. For example, in a screen for shRNAs which overcome a cancer cell-line's resistance to a chemotherapeutic reagent, a positive shRNA would result in the cancer cell succumbing to the chemotherapeutic reagent and dying. Because the cell is dead, it becomes very difficult to recover the shRNA sequence responsible.

The present invention provides novel direct methods to recover shRNA sequences from cells that are undergoing programmed cell death (apoptosis). During apoptosis, the genomic DNA in the cell becomes fragmented into pieces—either a characteristic ladder of multiples of 200 base pairs, or in some cell lines fragments of a few kilobases. However, the fragments are significantly larger than a typical shRNA cassette, so that the shRNA cassettes can be recovered by PCR even from apoptotic cells.

DNA from apoptotic cells can be separated from DNA from non-apoptotic cells by either (A) FACS sorting cells at an early stage of apoptosis, and recovering total DNA from this subpopulation; or (B) taking the entire cell population and specifically recovering genomic DNA undergoing fragmentation. This can be achieved by: (i) PEG precipitation with for example 2.5% PEG 8000, 1M NaCl as described in Ioannou and Chen, "Quantitation of DNA fragmentation in apoptosis," *Nucleic Acids Res.* 1996 Mar. 1; 24(5):992-3; (ii) electrophoresis of total DNA on an agarose gel, followed by gel purification of only DNA fragments too small to be intact chromosomes; or (iii) any other size-selective method of DNA purification.

Methods for Expanding Diversity/Improving Efficacy Via Error-Prone PCR and FACs Assay.

Many natural microRNAs, and many designed siRNAs and shRNAs, incorporate mismatches both to their targets, and within their double-stranded stems. In contrast, the shRNAs produced by our procedure do not. However, the presence of such mismatches can affect how efficiently the shRNAs function. The diversity of our shRNA cassette libraries can be increased by incorporating such mismatches randomly. This could be done either to the original library or after selection of (screening for) 'active' shRNA cassettes. After incorporation of random mismatches the shRNA cassettes can be rescreened to identify ones with altered efficacy, for example using our FACS assay. In this way a weakly effective shRNA cassette can be converted to a strongly effective one or vise-versa.

There are several ways in which such random mismatches can be incorporated, including:

(A) Error-prone PCR of the shRNA cassettes, using any of the established methods of increasing the error-rate of PCR (e.g. error-prone polymerases, inclusion of Mn2+ in the reaction buffer, use of nucleotide analogues etc.)

(B) Maintenance of the shRNA cassette in a vector in a host that causes a high frequency of mutations. For example the activated B-cell line Ramos.

(C) Through copying of the shRNA cassette in another error prone manner. e.g. through the use of a mutant, error-prone bacterial phage polymerase. e.g T7 RNA polymerase.

Method for Recovery and Concatenation of shRNA Cassettes

Using an assay system of the present invention, the small pool of cells carrying an active shRNA can be identified from the pool of cells not carrying an active shRNA. One way to identify which shRNA's are present in the active pool is to PCR amplify the shRNA cassettes. The PCR products (which will contain a mixture of sequences representing the pool of active shRNAs) can be cloned and individual clones sequenced, or the PCR product can be sequenced directly using a parallel sequencing technology such as 454 Life Sciences sequencing or Solexa sequencing.

However, since each shRNA cassette is uniquely identified by the sequence on one of the strands of the hairpin (around 20-40 base pairs) this makes inefficient use of sequencing resources, which typically allow reads of several hundred basepairs. In addition, the strong secondary structure that the hairpin represents can interfere with the sequencing reactions, producing traces that are hard to read. The present invention provides solutions to both these problems.

The shRNA cassettes are designed so that there is a restriction enzyme site within the loop. The restriction enzyme is chosen to produce a cohesive-end compatible with one of the enzymes used for cloning the intact cassette, although this is not essential. For example, the loop can contain a BamHI site if the cassette is cloned as a BglII/blunt fragment, or a SalI site if the cassette is cloned as an XhoI/HindIII fragment.

The active shRNA cassettes are PCR amplified from the individual cell or pool of cells determined to contain active shRNAs. It is advantageous to use a strand-displacing DNA polymerase such as Vent polymerase for this PCR reaction as this improves amplification through the strong secondary structure that can form from the hairpin sequence. The PCR product is then digested with both the enzyme present in the loop sequence and the corresponding enzyme used to clone the cassette. This releases small fragments of DNA of around 20-40 base pairs in length (depending on the exact shRNA cassette cloning strategy employed) which have compatible sticky ends.

T4 DNA ligase is used to concatenate these small fragments into longer pieces. The longer pieces are then cloned and sequenced. The sequence information can then be processed to reveal the sequences of all the shorter fragments that were ligated together to form the longer piece. It is not essential that the two restriction enzymes used have compatible sticky ends so long as it is possible for the small fragments to oligomerise. This will be possible for most restriction enzyme pairs (including all those for which the overhang is 'palindromic'—i.e., has the same sequence as its reverse/complement).

There is an optimum length for the longer pieces generated by ligation of the released fragments of DNA. However, unless it is restrained, T4 DNA polymerase will tend to produce either extremely long pieces, or circular pieces of DNA caused by ligation between the two ends of a single piece of DNA. Circularization can be limited by adding PEG to the ligation. A second method is to 'spike' the reaction with a small quantity of an 'adaptor' molecule that consists of a piece of DNA with the same sticky-ends as the small fragment (or one compatible sticky end and one blunt, non-compatible sticky end, or blocked end). The 'adaptor' molecule includes a restriction enzyme site. Preferably for a rare-cutting restriction enzyme (e.g. NotI). The adaptor molecule becomes incorporated into the growing concatenated chain of small fragments in a statistically random fashion. Once the ligation reaction is complete, the concatenated chains are cut with the enzyme whose site was present in the adaptor molecule. This will linearise any circular molecules so long as they contain at least one copy of the adaptor. The average length of the fragments released by this digestion will be a function of the initial molar ratio of small fragments to adaptor molecules. The reaction conditions can therefore be adjusted to maximise the yield of fragments of the optimum length. This approach can also be valuable in the 'SAGE' procedure where short sequence tags are ligated together and sequenced in order to assay relative levels of gene expression.

Methods for Generating an Epi-Allelic Hypomorphic Series of RNAi Trigger Molecules An important application of the invention is the generation of a graded series of RNAi trigger molecules (e.g., shRNA molecules) that knock down the expression of a target gene in a range of silencing activity, and in some cases, to a preferred, predetermined level of expression. That is to say, a plurality of individual RNAi trigger molecules identified by the methods of the invention can be used to create an epi-allelic hypomorphic series of gene regulators.

To generate multiple RNAi inducing molecules directed to the same target gene, an unbiased high-throughput screen is undertaken according to the methods described herein, for example, according to any of the methods described in Examples 1-3 and 6. Through screening a large number of candidate shRNA sequences (e.g., around 200 per gene), the methods described herein readily identify multiple effective shRNA sequences for any given target of interest.

There are at least two significant advantages to having multiple shRNA molecules per gene. First, "off-target" effects remain a significant problem in interpreting RNAi experimental results. "Off-target" effects occur when an shRNA down-regulates a gene or genes other than its intended target. Demonstrating that two (or preferably three or more) independent shRNAs to the target gene each give the same phenotypic effect is one of the simplest and most convincing controls available to disqualify off-target effects in the interpretation of results (*Nat. Cell Biol.*, 5:498-490 (2003); Cullen, *Nature Methods* 3:677-681 (2006)).

Second, having a set of shRNAs with differing silencing potentials provides an "epi-allelic" series of hypomorphs, that is to say, a genetic dose-response. This plurality of RNAi trigger molecules will contains RNAi triggers that inhibit the expression of the target gene within a range of repression activity. For example, some RNAi trigger molecules will demonstrate relatively high degrees of target repression, while others will show lower degrees of repression as well as intermediate levels of repression. An especially useful hypomorphic series of RNAi trigger molecules will include molecules that collectively show a wide range of repression activity, including intermediate values.

An epi-allelic hypomorphic series that constitutes a genetic dose-response has a variety of significant applications. In some aspects, the set of hypomorphic gene regulators can be used to explore in vivo gene function. In other aspects, the gene regulators can be used to validate candidate therapeutic drug targets and predict in vivo responses to inhibitor compounds. In still other applications, the present invention can be used to identify RNAi trigger molecules that can reduce the expression of a target gene to any desired level. The full scope and value of the epi-allelic hypomorphic series of gene regulators generated by the present invention will be apparent to one of skill in the study of gene regulation, genetic diseases, tumor biology, drug target identification, the development of small molecule and genetic-based disease therapeutics, and many other areas of biology. It is not intended that use of an epi-allelic hypomorphic series generated by the present invention be limited by the few examples discussed herein.

In other embodiments, the epi-allelic hypomorphic series generated by the methods of the invention can be used to analyze a therapeutic threshold in drug development (e.g., a DNA-based therapeutic or a small molecule drug). Investigation of a therapeutic threshold relates specific gene expression levels to a defined phenotypic effect. This analysis will provides information regarding what level of gene inhibition is required in order to observe a therapeutic benefit. This dosage analysis can improve target-phenotype correlations (Hemann et al., *Nat. Genet.*, 33:396-400 (2003)).

This principle of creating an epi-allelic hypomorphic series is demonstrated herein using the receptor tyrosine kinase Axl as a target gene. See Example 5. Axl is a regulator of tumor growth, invasion and metastasis. Using an epi-allelic hypomorphic series of RNAi trigger molecules generated by the methods of the invention, it is demonstrated in Example 5 that sustained in vivo knockdown of Axl inhibits breast carcinoma formation using non-invasive in vivo imaging of subcutaneous tumor cell xenograft model, and further, provides information regarding what degree of Axl expression is necessary to inhibit tumor growth. Similarly, the initial steps in characterizing an epi-allelic hypomorphic series of RNAi trigger molecules directed against the kinase Akt is provided in Example 6.

Polynucleotide Sequences of RNAi Trigger Molecules Generated by Methods of the Invention In one aspect, the invention provides polynucleotide sequences derived from the Axl, Akt1 and human proteasomal subunit beta 5 (PSMB5 or beta5) genes that have RNAi trigger molecule activity. These molecules were generated as described in the Examples sections. These polynucleotides find use in the downregulation of expression of the respective target genes. These polynucleotide sequences of the invention are provided in FIG. 37. In this figure, the shRNA hairpin polynucleotide sequences are shown (SEQ ID NOs: 1-15). The shRNA sequence positions corresponding to the loop domain are shown in all caps. The mRNA targeting sequence (i.e., the sequence and the complement of the sequence that form the stem) are in lower case letters on either side of the loop domain. The orientation of the shRNA sequence as written is shown as either sense-LOOP-antisense or antisense-LOOP-sense.

Also shown in the tables in FIG. 37 are the corresponding mRNA target sequences without any non-gene loop sequence (SEQ ID NOs: 16-30). These mRNA target sequences are a subset of the larger shRNA molecule.

Any of the polypeptides provided in FIG. 37 can be used as shRNA molecules (e.g., SEQ ID NOs: 1-15), or can be used to construct shRNA molecules (e.g., SEQ ID NOs: 16-30).

It is intended that the invention also include active variants of the polynucleotide sequences of SEQ ID NOs: 1-30. As used herein, an active variant polynucleotide RNAi trigger molecule is a polynucleotide sequence that is at least 80%, 85%, 90%, 91%, 92%, 93%, 94%, 95%, 96%, 97%, 98% or 99% identical to a polynucleotide sequence of SEQ ID NO: 1-30 and further retains any degree of RNAi trigger molecule activity towards the Axl or Akt target. An active variant of a polynucleotide sequences of SEQ ID NO: 1-30 also includes deletion variants or fragments of the polynucleotide sequences of SEQ ID NOs: 1-30, where the deletion variant or fragment retains at least 80%, 85%, 90%, 91%, 92%, 93%, 94%, 95%, 96%, 97%, 98% or 99% of the polynucleotide sequence of SEQ ID NO: 1-30 and further retains any degree of RNAi trigger molecule activity towards the Axl or Akt target. Methods for determining sequence identity percentages (e.g., BLASTN using default parameters) are generally available. Methods for assessing RNAi trigger molecule activity are described herein.

For sequence comparisons, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols In Molecular Biology*, Ausubel et al., eds., *Current Protocols*, a joint venture between Greene Publishing Associates, Inc. and John Wiley & Sons, Inc., (supplemented through 2004).

One example of an algorithm that is suitable for determining percent sequence identity and sequence similarity is the BLAST algorithm, which is described in Altschul et al., *J. Mol. Biol.*, 215:403-410 (1990). Software for performing BLAST analyses is publicly available through the National Center for Biotechnology Information (see the NCBI website). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., (1990) *J. Mol. Biol.*, 215:403-410). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Protocol for Semi-Attached Generation of shRNAs

Step 1: Generate Short Blunt Ended Fragments of the Target DNA

The target DNA of interest is fragmented using any known method (e.g., restriction digestion or random shearing). For example, the following 4-cutter restriction enzymes, individually or in combination, can be used:

HpaII, Hin6I, AluI, DpnI, BsuRI, RsaI, HpyCH4V, Bsh12361.

HpaII and Hin6I leave two base pair overhangs, so these are blunted with Klenow (or T4 DNA polymerase or a similar enzyme). HpaII, Hin6I and AluI are disabled by heat treatment to avoid interfering in the next step. (HpaII and Hin6I are simply not needed whereas AluI would cut within the specific loop adaptor that is used).

Step 2: Ligate on Loop Adaptor

The loop adaptor is ligated to the blunt ended fragments in the presence of different restriction enzymes. An enzyme (e.g. PvuII or PmeI) is included to cleave loop adaptor dimers back into monomers. In addition, the same enzyme as used in step 1 (if applicable) is added to the mix to prevent re-ligation of the target fragments. However, because of the fill in reaction on fragments prepared with HpaII and Hin6I, a different enzyme (Bsh12361) is used. There is an AluI site in the loop adaptor, so this enzyme is also not used (and disabled from the initial fragment preparation by heat treatment). See the loop adaptors in FIGS. 5A-5C and 9-11 for examples of adaptors successfully used in the present methods. These adapters have the following features or properties:

(A) A recognition site for a DNA endonuclease that cuts outside the recognition site. This site is placed such that when the loop is ligated to a target fragment of DNA, the cut site is between 21 and 30 base pairs from the junction between the loop adaptor and the target DNA. Loop adapters using EcoP15I have been successfully used for this purpose (see FIGS. 9 and 11). Loop adapters using McrBC can also be used (see FIG. 10). Use of the latter relies on the inclusion of a suitable methyl-C modified base into the oligo sequence.

(B) The sequence of the loop adaptor is chosen so that formation of loop-adaptor dimers by ligation creates a new restriction site whose cleavage regenerates loop-adaptor monomers. We currently choose the sequence CTG as the first 3 base pairs of the adaptor, producing a site for the blunt end cutter PvuII, or AAAC as the first 4 base pairs of the adaptor, producing a site for the blunt end cutter PmeI.

(C) A 5' phosphate. (Either by chemical synthesis or treatment with polynucleotide kinase).

(D) Restriction sites allowing for the later removal of some or all of the loop adaptor-derived sequence from the cloned hairpins. A pair of sites that cut outside their recognition sequence have been successfully used. Suitable sites are GsuI, BpmI, BpuE1, BsgU, AcuI or Eco57I sites, and any combinations of those sites, or alternatively still, any combination of one of those sites and a BsrDI site, a BstF5I site or a BtsI site. A pair of GsuI sites positioned to remove most of the adaptor-derived sequences but leaving behind a defined loop sequence has also been used successfully.

The loop adaptor can optionally also contain a selectable marker. One or more than one copy of the lacO binding site for the *E. coli* lad DNA binding protein can be used. This sequence can be used as a positive selectable marker in strains of *E. coli* carrying an antibiotic selection marker downstream of lacO sequences (and thus under the control of the lad operon) within their genome. In the absence of exogenous lacO sequences, lad binds upstream of the antibiotic selection marker and prevents expression of antibiotic resistance. In the presence of a multi-copy plasmid carrying lacO, lad binds to the multiple copies of lacO present on the plasmids and is titrated away from the genomic lacO:: antibiotic marker, thus allowing the marker's expression. Thus in the presence of the lacO-carrying plasmid the *E. coli* acquire resistance to the antibiotic. Suitable strains exist conferring lacO-dependent resistance to ampicillin or kanamycin. See, e.g., the following strains:

Strain 1: BUN22 (BW28705IA) lacIQ rrnB3 DlacZ4787 hsdR514 D(araBAD)567 D(rhaBAD)568 galU95 DendA9::FRT DrecA635::FRT umuC::ParaBAD-I-SceI-Frt lacI::lacI-Plac-bla.

Strain 2: BUN23 (BW28705IK) lacIQ rrnB3 DlacZ4787 hsdR514 D(araBAD)567 D(rhaBAD)568 galU95 DendA9::FRT DrecA635::FRT umuC::ParaBAD-I-SceI-Frt lacI::lacI-Plac-npt.

The same approach can also allow negative selection (ie selection against the presence of lacO). In this case a negative selectable marker such as SacB (which is lethal in the presence of sucrose) is placed on the *E. coli* chromosome under the control of lad (instead of an antibiotic marker). The ability to both positively select for the presence of the loop, and subsequently select for LOSS of the unwanted portion of the loop simplifies later steps.

Step 3: Remove Excess Loop Adaptor

Unincorporated loop adaptors (ie ones unligated to target DNA fragments) can be removed in many ways. We perform phenol extraction, chloroform extraction, and DNA precipitation. DNAs larger than about 75 base pairs can be precipitated by increasing the $Mg^{2+}$ concentration to >50 mM with $MgCl_2$ and adding polyethyleneglycol 8000 to a final concentration of 13%. Precipitated DNA is recovered by centrifugation, washed in 80% ethanol, and resuspended in water.

Step 4: Cleave Off Target Tags Fused to Loop Adaptors

The loop adaptors are cleaved off the ends of the target DNA together with a 21-30 nt tag of target DNA by treatment with EcoP15I (or McrBC or similar). In the case of EcoP15I we improve efficiency by including 10 µM sinefungin in the reaction.

Released tags are blunt-ended with Klenow fragment of DNA polymerase I (or T4 DNA polymerase or similar) and dephosphorylated. We use a mixture of Antarctic Phosphatase and Shrimp alkaline phosphatase. Tags are then purified. Many purification methods are possible but we currently use either 1) gel purification on a polyacrylamide gel (approx 10%) followed by 'crush and soak' recovery of the DNA from the excised band in acrylamide; or 2) Electrophoresis in a 2% agarose gel run in 5 mM sodium borate solution followed by electroelution from the agarose and cleanup by e.g. phenol/chloroform extraction and ethanol precipitation. (The blunt-ending and dephosphorylation can occur in either order, either before or after gel purification, by standard methods).

Step 5: Preparation of Cloning Vector.

This can be the final vector, or an intermediate cloning vector from which complete shRNA cassettes are transferred to the final cloning vector. This vector must be prepared so that it has one blunt end and one end with an overhang. The positions of both the blunt end and the non-blunt end are carefully selected so that the final hairpin sequence is placed in the correct sequence context. The presence of a blunt end and a non-blunt end inhibits recircularisation of the vector and also allows the blunt-ended hairpin tags from step 4) to only ligate to one end of the vector. An enzyme producing a non-palindromic overhang can be used so that the vector cannot dimerize via ligation between the overhangs. Alternatively, an enzyme producing a palindromic overhang can be used so that the vector will dimerize via ligation between the overhangs. This dimer has suitable blunt ends for ligation to the hairpins at both ends. The dimerization removes the free ends from the ligation reaction so that they no longer compete for binding to the ligase enzyme.

Vectors have been successfully produced using, for example, AfeI, NaeI or PvuII to produce the blunt end, and, for example, AscI to produce the sticky end. Cut vectors are gel purified (although other purification methods can be used). See FIGS. 12-16 for illustrations of vectors finding use with the invention.

Step 6: Ligation of Hairpin Tags to Cloning Vector

A slight molar excess of hairpin tags from step 4) are ligated to the vector from step 5) in the presence of AfeI, NaeI or PvuII as appropriate to inhibit vector recircularization. This produces a product in which the 5' phosphate from the blunt end on the vector is ligated to the 3'OH of the hairpin tag. However, the hairpin tag lacks a 5' phosphate and is therefore unable to ligate to the 3'OH of the blunt end on the vector. This leads to production of a large DNA molecule with a loop at one (or both) end, and a single-strand nick 5' to the loop. This product can optionally be treated with exonucleases to degrade any vector that has not been ligated to a hairpin tag at both ends. DNA polymerase I Klenow fragment can be used to initiate DNA polymerization from this nick. Other strand displacing polymerases such as Vent or BstI can also be used. This polymerization step 'opens out' the loop.

Following 'opening out' the vector dimer is cleaved into two monomers using a suitable enzyme. Although the same enzyme as used in step 5 can be used, the enzyme sites for AarI or XcmI are typically positioned to put the 3' end of the opened out shRNA cassette into the correct context. The overhangs produced by cutting with these enzymes are blunted with T4 DNA polymerase, Klenow or similar suitable polymerase.

The vector can optionally be gel purified at this stage to separate unligated vector from vector that has had an opened-out hairpin tag added. Purification will not be required if the loop-adaptor oligo incorporates a selectable marker such as lacO.

Step 7: Cloning of the Intermediate Library

The vector+opened-out hairpin tag is now circularized by ligation and cloned into a suitable *E. coli* strain. Electroporation followed by plating onto LB Agar containing suitable antibiotics (e.g., kanamycin) have been successfully used. An intermediate library has been prepared at this step by scraping up the colonies following transformation and isolating the DNA. Alternatively, the intermediate library could be grown in liquid or semi-liquid culture to for amplification, but this is likely to lead to more bias within the library.

Step 8: Removal of Unwanted Sequences within the Loop.

The intermediate library is digested with GsuI and treated with DNA polymerase I Klenow fragment (or T4 DNA polymerase etc) to generate blunt ends. Cut vector is then purified away from any uncut background (contributed for example by empty clones within the library) and re-circularised by ligation. At this stage the library can be transformed into *E. coli* again, although this time under negative selection for lacO if appropriate, and a fresh DNA preparation made from the pooled colonies. Alternatively the re-ligated DNA can be immediately processed for transfer into the final expression vector. Transfer into the final vector can be performed either by conventional subcloning, by Gateway mediated recombination, MAGIC or similar subcloning strategies. We currently transfer the final cassette as a simple PacI/HindIII fragment to similarly cut final vector. Once again, negative selection for lacO can be used to select against clones in which the extra sequences within the loop have not been removed. Alternatively, background clones in which the loop has not been deleted can be suppressed by digesting the ligation mixture with an enzyme that has a recognition site within the unwanted portion of the loop but nowhere else (as described before, e.g., PmeI).

Example 2

Construction of a shRNA Library Directed Against the Vascular Endothelial Growth Factor Receptor 2

This example describes the construction of a single gene shRNA library directed against the vascular endothelial growth factor receptor 2 (VEGFR2 or KDR).

Conversion of cDNA into Tagged Hairpin Loops

1) Digestion of the cDNA into Short Blunt-ended Fragments

A VEGFR2 cDNA clone was released from its cloning vector by digestion with Sal1 and EcoRI. Three bands were released of approximate size 2.5 kb, 1.4 kb and 300 base pairs. All three bands were cut from the gel, pooled and purified over a GF/X column to produce Band M553. Band M553 was measured to contain approximately 50 ng/µl DNA.

Three µl aliquots of M553 were cut with each of the following frequent-cutter enzymes in a total volume of 20 µl 1× Tango Buffer (Fermentas):
   a) HpaII and Hin6I mixed
   b) AluI
   c) DpnI
   d) BsuRI
   e) RsaI
   HpyCH4V Aliquots were digested for >1 hr at 37° C. Aliquots (a) and (b) were then made blunt ended by the addition of 2 µl of the following mix:
   0.5 µl 10× Tango buffer
   0.7 µl 10 mM dNTPs
   0.2 µl Klenow
   3.6 µl H2O Samples (a) and (b) were incubated at room temperature for 15 minutes, and then the Klenow enzyme was inactivated by incubation at 80° C. for 15 minutes. 1 µl Bsh1236I was added to sample (a).

2) Ligation of the Loop Oligo

The following ligation mix (20 µl aliquots) was added to each of aliquots (a) through (f):
   14 µl 10× Tango buffer (Fermentas)
   14 µl 20 mM DTT
   1.4 µl 100 mM rATP
   7 µl 10 µM oligo DK540 (carrying an EcoP15I site and one copy of lacO)
   3.5 µl PvuII
   0.7 µl Quick ligase (NEB, high concentration T4 ligase)
   39.4 µl H2O Reactions were allowed to ligate overnight with alternating ligation periods (2 hrs at 18° C.) and 'cutting' periods (30 min at 37° C.) to allow the PvuII to cleave any oligo dimers formed, to allow remaining frequent-cutter enzyme (HpyCH4V, Bsh1236I etc) to cleave religated cDNA. The ligations were then stopped by heat treatment at 80° C. for 20 minutes and pooled.

3) Removal of Excess Loop Adaptor Oligo

Excess oligo DK540 was removed by a size selective precipitation step by the following protocol.

Approximately 20 µg glycogen carrier was added to the pooled samples. Samples were then extracted once with 50 µl TE-equilibrated phenol. The aqueous phase was recovered and extracted once with 50 µl chloroform. The aqueous phase was recovered and adjusted to approximately 100 mM $MgCl_2$ by the addition of 1/10 volume 1M $MgCl_2$. The aqueous phase was then adjusted to 13% PEG 8000 by the addition of 13/37 volume 50% PEG 8000.

The sample was mixed well, and DNA larger than approx 50 base pairs was recovered by centrifugation for 30 minutes in a microfuge at top speed. The supernatant was discarded and the pellet was washed once with 80% ethanol. The recovered DNA was resuspended in 50 µl H2O.

4) Cleaving Off Target Tags Fused to Loop Adaptors

50 µl aliquots from the following mix were added to the DNA recovered in the previous step:
   10 µl Buffer 3 (New England Biolabs=NEB)
   10 µl BSA (1 mg/ml)
   5 µl 200 µM sinefungin
   1 µl 100 mM ATP
   2.5 µl EcoP15I
   21.5 µl H2O (Sinefungin has been reported to improve cleavage by EcoP15I). The DNA was digested overnight at 37° C. The DNA was then dephosphorylated by the addition of:
  10 µl 10× Antarctic Phosphatase buffer (NEB)
  1 µl Antarctic phosphatase (NEB)
The reaction mix was incubated at 37° C. for one hour.

The sample was then processed using the following protocol. Approximately 20 µg glycogen carrier was added to the sample. The sample was extracted once with 50 µl TE-equilibrated phenol. The aqueous phase was recovered and extracted once with 50 µl chloroform. 1/10 volume 3M sodium acetate pH 5.5 was added to the aqueous phase. 2.5 volumes of 100% ethanol were added to the aqueous phase. DNA was recovered by centrifugation for 30 minutes in a microfuge at top speed. The supernatant was discarded and the pellet washed once with 80% ethanol.

The pellet was resuspended in 50 µl 1× Tango buffer (Fermentas) containing 200 µM dNTPs. 0.5 µl Klenow polymerase was added to make the DNA blunt-ended. After incubation at room temperature for 15 minutes, the Klenow polymerase was inactivated by the addition of 1/5 volume 6× gel loading buffer (Fermentas) and run on a 2% agarose gel prepared in 5 mM sodium borate.

The tagged hairpin loops ran at approximately 70-90 base pairs (slightly larger than expected from the number of nucleotides present—possibly due to the loop structure). Released loops were recovered by electroelution onto GF/C paper (Whatman) backed by dialysis tubing. Hairpin loops were recovered from the GF/C paper/dialysis by placing in a home-made spin column and centrifuged for 2 minutes at top speed in a microfuge. The GF/C paper/dialysis tubing was retained in the top part of the column while buffer/DNA was collected in the lower tube.

The tagged hairpin loops were then processed as follows. Approximately 20 µg glycogen carrier was added to the samples. Samples were extracted once with 50 µl TE-equilibrated phenol. The aqueous phase was recovered and extracted once with 50 µl chloroform. 1/10 volume 3M sodium acetate pH 5.5 was added to the aqueous phase. 2.5 volumes 100% ethanol were then added to the aqueous phase. DNA was recovered by centrifugation for 30 minutes in a microfuge at top speed. The supernatant was discarded and the pellet washed once with 80% ethanol. The tagged hairpin loops were then resuspended in 20 µl H₂O to produce Band M555.

Figure 17:
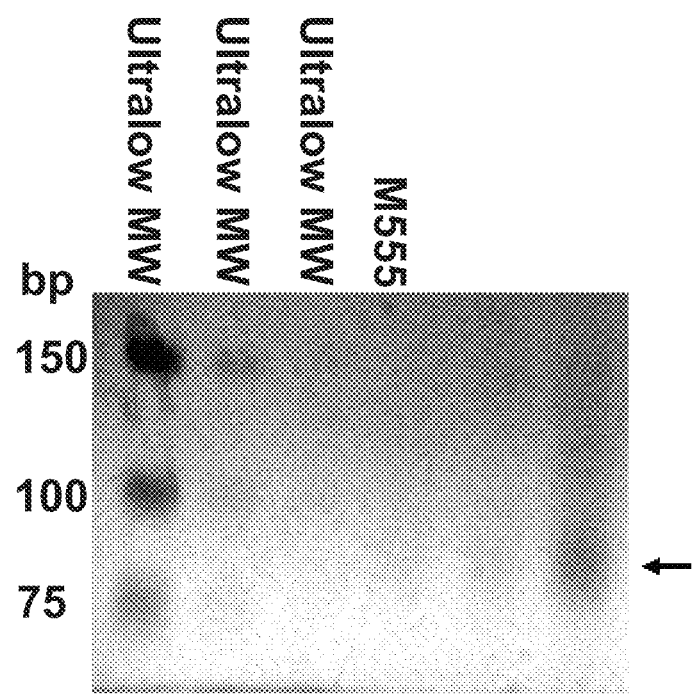
FIG. 17 provides a photograph of resolved DNA on an agarose gel, where the DNA samples are fragments recovered after EcoP15I digestion. Also shown on the gel is a sample of Fermentas ultralow ladder markers.

Two µl M555 were run on a gel along with known amounts of Fermentas 100 base pair ladder. See FIG. 17. Using the brightness of the bands, the concentration was estimated at 0.45 ng/µl. Although this is a small amount in terms of mass, because the hairpins are small it corresponds to approx 10 nM, which is more than adequate.

Cloning and Opening Out of Tagged Hairpin Loops in Intermediate Vector

Intermediate vector L267 (pENTR-U62TetONaeIXcmI) is derived from pDONR221, a Gateway vector from Invitrogen. It carries a kanamycin resistance marker. Within the Gateway cloning cassette, L267 carries in the following order:
  a PacI site, followed by a modified U6 promoter incorporating two binding sites (tetO) for the *E. coli* tetracycline repressor protein tetR;
  an NaeI site positioned exactly at the U6 start of transcription;
  additional sites including a NarI site; and
  an XcmI site positioned to produce a TTTTT DNA polymerase III termination signal following XcmI digestion and blunt-ending.

L267 was cut with NaeI and NarI and the approximately 3 kb vector fragment was gel purified to produce band M557. M557 was purified over a GF/X column and recovered at a concentration of approximately 20 nM. Band M557 has a blunt end derived from NaeI digestion and a sticky-end derived from NarI digestion.

M557 was then ligated to M555 in the following reaction mix to produce Ligation N753:
  2 µl M557 (c. 40 fmoles)
  4.5 µl M555 (c. 40 fmoles. Note: a 2× excess would have been optimal)
  2 µl 10× Tango buffer (Fermentas)
  0.2 µl 100 mM rATP
  1 µl 20 mM DTT
  0.5 µt NaeI
  0.25 µl Quick ligase (high concentration ligase) from NEB.
  H₂O to 20 µl.

NaeI was included to reduce the background of vector dimerization/recircularisation. The vector is still able to dimerize by ligation of the NarI overhangs but this is not a disadvantage. After overnight ligation at 30° C., the ligation/digestion of N753 was terminated by incubation at 65° C. for 15 minutes.

Further NaeI (0.5 µl) and XcmI (1 µl) were added to N753, followed by incubation at 37° C. for 90 minutes. Addition of XcmI releases vector monomers from any dimers formed by ligation of the NarI overhangs, and prepares the 3' cloning site of the vector.

At this stage, there should be a hairpin loop ligated to the NaeI-derived blunt end of the vector, with a nick at the 5' end of the hairpin loop. The other end of the vector has a single base pair 3' overhang generated by XcmI. Klenow polymerase was then used to 'open-out' (or 'stretch') the hairpin into double-stranded DNA. At the same time, the Klenow will remove the single base pair 3' XcmI overhang to produce a blunt end.

To each sample, 10 µl from the following cocktail was added:
  1 µl 10× Tango buffer
  0.3 µl 10 mM dNTPs
  0.5 µl Klenow fragment DNA polymerase I (Fermentas)
  8.2 µl H₂O Reactions were incubated at room temperature for 10 minutes. DNA loading buffer (including EDTA) was added and heat kill at 80° C. for 10 minutes.

Samples were then gel purified on a 1% TBE gel, alongside NaeI/XcmI cut L267 vector. The size shift was quite small. The correct size is approximately 3.0 kb compared to 2.85 kb for vector alone. The band was cut out of the gel and purified over a GF/X column to produce band M559S.

From the M559S preparation, 9 µl aliquots were removed and ligated in a total volume of 12 µl 1× ligase buffer and 0.16 µl T4 DNA ligase for 5 hrs. The ligation mix was then purified over a GF/X column and eluted into 10 µl H₂O. 2 µl of the eluate was used for electroporation with New England Biolabs 10-beta electrocompetent *E. coli* according to the manufacturer's protocol. Colonies were scraped and DNA prepared using a commercial miniprep kit (Fermentas). The DNA thus obtained (N757) represents the VEGFR2-directed shRNA library cloned into an intermediate vector.

Removal of Unwanted Loop Sequence

Correct clones in N757 contain a pair of GsuI sites positioned to allow the removal of most of the loop sequence. Parental vector and most other wrong clones contain no GsuI sites and cannot be cut with GsuI. N757 was cut with GsuI and gel purified twice to get rid of all traces of uncut vector, and purified into 50 µl H₂O over a GF/X DNA purification column. This produces band M567. M567 was then blunt-ended by the addition of:

10 µl 10× Klenow buffer
   1 µl 10 mM dNTPs
   1 µl Klenow
   38 µl H2O.

After 10 minutes at room temperature, M567 was purified over a GF/X column and eluted in 30 µl H2O.

From that elution, 2 µl of the M567 was ligated in a total volume of 10 µl 1× ligase buffer and 0.5 µl T4 DNA ligase for 1 hr. The ligation mix was then purified over a GF/X column and eluted into 10 µl H₂O.

From that elution, 2 µl was used for electroporation using New England Biolabs 10-beta electrocompetent E. coli according to the manufacturer's protocol. Transformed cells were plated on LB-agar plates with 50 µg/ml kanamycin and allowed to grow overnight at 37° C. Thousands of colonies were obtained. The colonies were scraped and DNA prepared using a commercial miniprep kit (Fermentas).

The DNA thus obtained (N770B) represents the VEGFR2-directed shRNA library cloned into an intermediate vector. This vector carries a PacI site, a U6 promoter, a shRNA construct, a TTTTT transcriptional terminator sequence and a HindIII site in that order.

Figure 18:
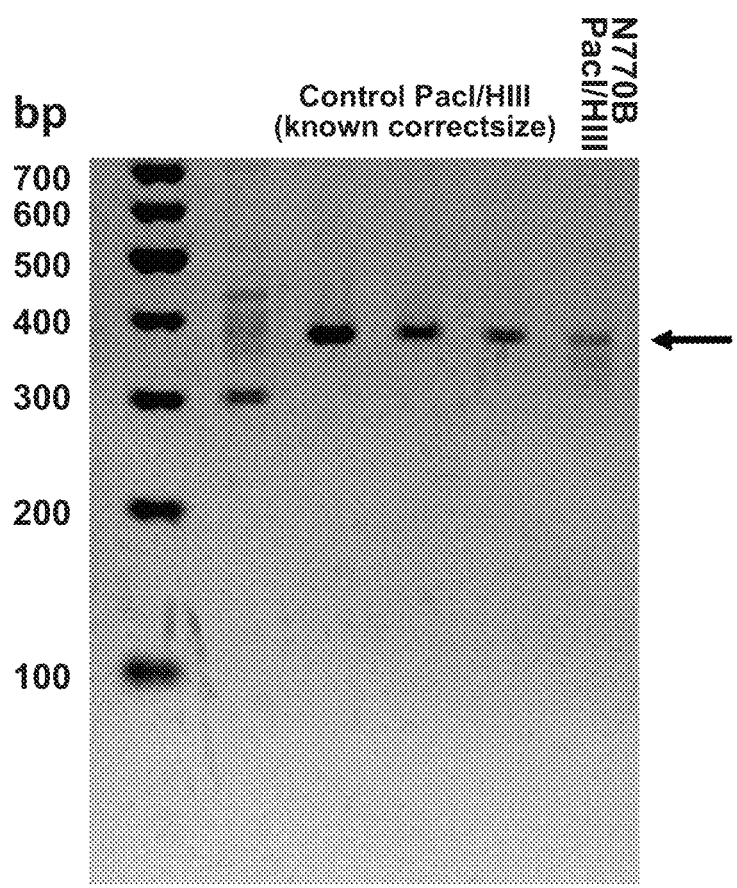
FIG. 18 provides a photograph of an agarose gel following PacI/HindIII digestion and resolution of a DNA sample derived from pooled colonies. Also shown on the gel is a sample of Fermentas 100 base pair ladder markers.

A sample of the pooled colonies was digested with PacI/HindIII and run on an agarose gel (see FIG. 18). The digested DNA (lane 6) was run alongside clones known by sequencing to carry the correct insert (lanes 3-5). Most of the inserts are the correct size, although some clones carry incorrect sized bands (e.g. two smaller bands below the arrow in lane 6).

Transfer of the shRNA Cloning Cassette to the Final Retroviral Vector

A cloning cassette containing the U6 promoter and shRNA was cloned from the intermediate vector into a final retroviral vector as described below. Retroviral vector L297 (RRI-Red) was cut with PacI and HindIII and gel purified twice to produce band M574. The intermediate library N770B was cut with PacI and HindIII and the appropriate band (running at 390 base pairs) gel purified to produce band M571. Band M574 was measured to be approximately 3 ng/µl and was approx 8000 base pairs. Band M571 was measured to be approximately 1 ng/µl and was approx 400 base pairs. The molar ratio is thus very approximately 7:1 for M571:M574.

Bands M574 and M571 were ligated together at approximately 2:1 molar ratio (3 µl M574 to 1 µl M571) in the following reaction:

1 µl 10× ligase buffer (NEB)
   1 µl M571
   3 µl M574
   0.25 µl T4 DNA ligase
   4.75 µl H₂O After ligation overnight, the mixture was diluted to 50 µl 1×SE-Y buffer (NEB) and 1 µl AfeI added to reduce background. AfeI was allowed to cut for 1 hr at 37° C.

The ligation mixture was then purified over a GF/X DNA purification column and eluted in 10 µl H₂O. 2 µl of the eluate was used to electroporate New England Biolabs 10-beta electrocompetent E. coli according to the manufacturer's protocol. Transformed cells were plated on LB-agar plates with 100 µg/ml ampicillin and allowed to grow overnight at 37° C. Thousands of colonies were obtained.

Most of these were scraped and used to produce DNA corresponding to the primary VEGFR2-directed shRNA library (N783).

An aliquot of this mixed library preparation was checked by digestion with PacI/HindIII and analysis on an agarose gel (see FIG. 19). The size of the band released from the vector was the expected approximate 390 base pairs.

Ten individual colonies were miniprepped and sequenced. Of these ten, eight had the expected hairpin structure. See FIG. 20. In FIG. 20, the sequences from transcription initiation to transcriptional terminator (TTTTT) are shown. Of those eight clones, only seven matched regions of the original VEGFR2 cDNA clone. The eighth matched a portion of the parent vector of our original VEGFR2 cDNA clone that immediately flanks the VEGFR2 sequence. This portion of the parent vector was included in the gel purified VEGFR2 cDNA fragments. The remaining two clones contained sequences matching VEGFR2 but did not have a hairpin structure.

The hairpin structures obtained differed in two ways from the hypothetical structures 'expected' from following our protocol 'in silico':

1) The length of the hairpin stem was somewhat variable from (22 base pairs to 28 base pairs) rather than the expected 27 base pairs. This is most likely due to variability in the exact cut site and end structure (blunt, 3' overhang or 5' overhang) produced by the restriction enzyme EcoP15I. This variability in no way reduces the usefulness of the hairpin structures obtained, and by increasing the diversity of the final library may actually be advantageous.

2) 0-3 additional base pairs are sometimes seen at the junctions between the hairpin and the loop, or between the second half of the hairpin and the vector. The origin of these unexpected basepairs is not known, but may be due to the well-known addition of a single untemplated base by many DNA polymerases. It is possible that at the levels of dNTPs used in these experiments (100 µM, higher than the optimal 30 µM) the Klenow fragment that was used (Fermentas) may have added untemplated bases. These additional basepairs are not expected to adversely affect the function of the shRNA expression cassettes.

Example 3

Experimental Demonstration of a FACS-based Screening Assay for the Identification of Active siRNA Molecules This example describes a working example of a FACS-based screen for the identification of shRNA clones that have specific inhibitory activity for the gene encoding the tyrosine kinase Axl gene. See FIG. 21 for an overview of the assay strategy.

Figure 23A:
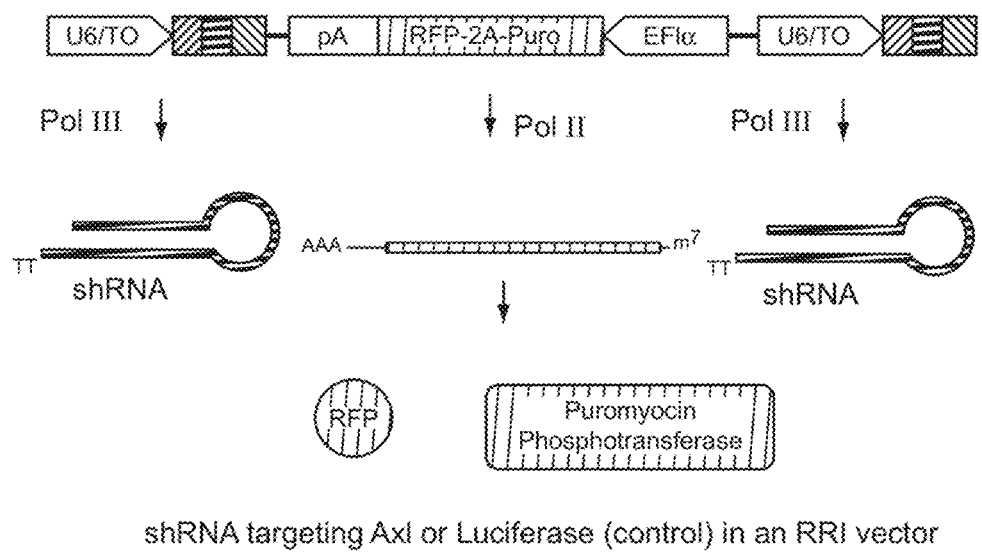
FIG. 23A shows red fluorescent protein (RFP) marked retroviral constructs expressing shRNAs targeting either Axl or luciferase. The vector also expresses puromycin phosphotransferase, which bestows puromycin resistance.

1) Construction of a Small Library of shRNA Clones Directed Against the Tyrosine Kinase Axl Gene A small Axl-mRNA library was made essentially as described in Example 2, except the hairpin adaptor oligo carried an MmeI endonuclease site instead of an EcoP15 site. Individual clones were sequenced and confirmed to contain Axl-directed shRNAs. An Axl shRNA clone that was previously shown to be active (Axl2 shRNA) and a shRNA clone directed against Luciferase (Luc shRNA) that should not target Axl were used as positive and negative controls, respectively. These shRNA constructs were in a vector that expresses both RFP and a Puromycin resistance protein. See FIG. 23A.

2) Construction of an Axl Specific Reporter Construct

Figure 22:
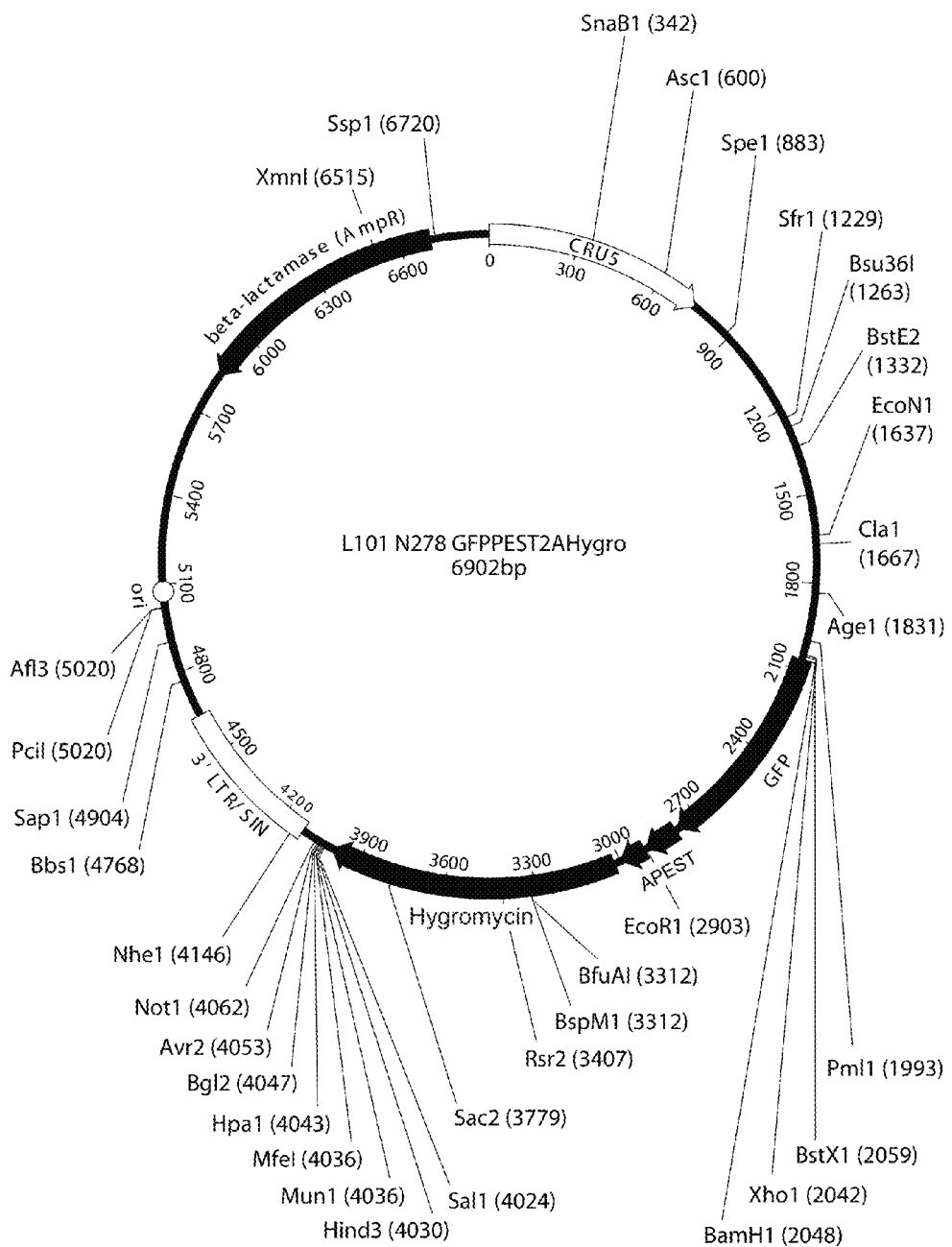
FIG. 22 provides an illustration of a vector that finds use with the assays of the invention for the detection of active siRNA molecules. The vector shown is termed L101, and is a retroviral vector expressing GFP-PEST 2A hygromycinR followed by a stop codon and a multiple cloning site. cDNAs of interest are cloned within the Sal1/Not1 multiple cloning site FIGS. 23A and B provide illustrations of constructs used in proof of principle experiments.
Figure 23B:
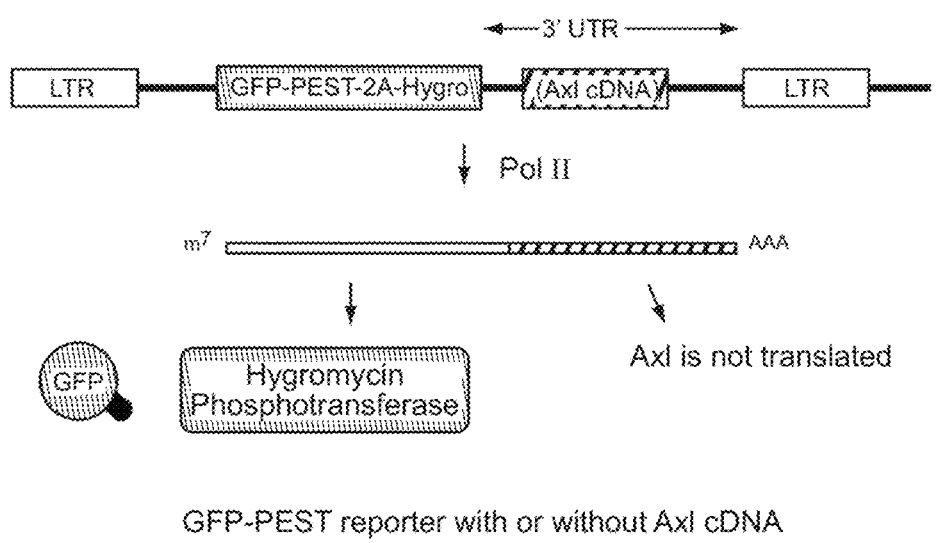
FIG. 23B shows retroviral vectors expressing GFP-PEST and hygromycin phosphotransferase (bestowing resistance to hygromycin), with or without an Axl cDNA cloned downstream of the GFP-PEST/ hygromycin phosphotransferase open-reading frame.

Axl cDNA from the publicly available clone IRAKp961H2049Q (rzpd.de) was cloned downstream of GFP-PEST in vector L101 retroviral vector (FIG. 22). A 2.9 kb BamHI/EcoRI fragment from the Axl cDNA clone was used to subclone into the MfeI/BglII sites of vector L101 (see FIG. 22). The resulting vector (called L110) produces a single transcript that includes the open reading frame for GFP-PEST-2A-HygroR, followed by a stop codon and 2.9 kb of Axl cDNA. The GFP-PEST-2A-HygroR open reading frame is translated. The "2A" sequence is a peptide from Foot and Mouth Disease Virus that leads to co-translational cleavage of the nascent protein into GFP-PEST-2A (a rapidly degraded form of GFP) and Hygromycin phosphotransferase, thus providing Hygromycin resistance. See FIG. 23B. Vector L101, which lacks the Axl cDNA sequence, was used as a control.

L101 and L110 vectors were introduced into packaging cells to produce retrovirus. The retrovirus was then used to infect MDA-MB-231 cells (a human breast cancer cell line, hereafter 231 cells). Pure populations of 231 cells carrying each of the constructs L101 and L110 were obtained by Hygromycin selection. These resulting lines were termed "L101 cells" and "L110 cells."

3) Testing the Control shRNAS

Figure 24:
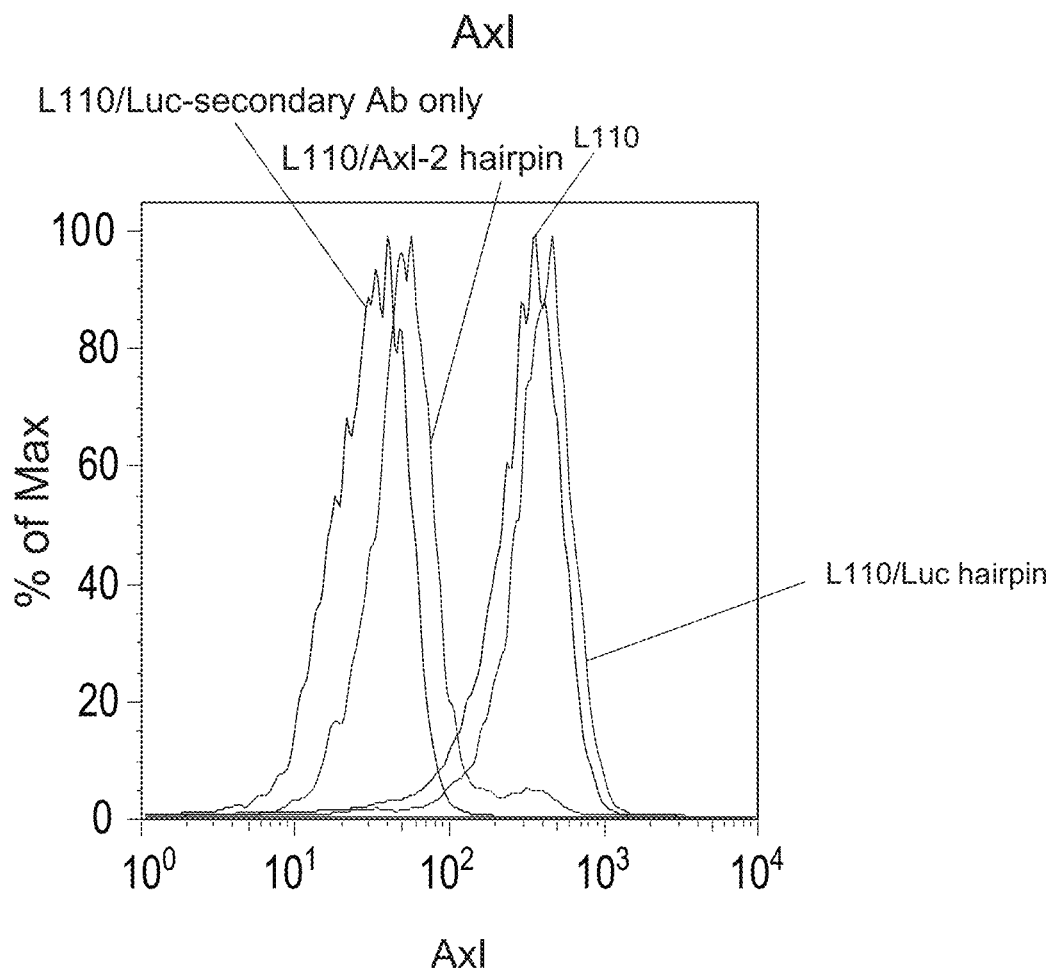
FIG. 24 provides flow cytometry results from the analysis of siRNA inhibition of gene expression. These results illustrate that the shRNA targeting Axl (Axl shRNA) knocks down Axl protein but the shRNA targeting luciferase (Luc shRNA) does not. L110 cells expressing either the Axl shRNA or the Luc shRNA, or no shRNA were stained with anti-Axl antibodies followed by a fluorescently-labelled secondary antibody and analysed on a flow cytometer. shRNAs were expressed from the RFP vector described in FIG. 23A. Cells expressing the Luciferase shRNA (green line) exhibit very similar Axl protein levels to control cells not expressing a shRNA (red shading). Cells expressing the Axl shRNA showed greatly reduced anti-Axl staining indicating reduced levels of Axl protein. For comparison, a population of cells not stained with anti-Axl antibody (orange shading) is also shown.

The L110 cells were infected with retrovirus carrying either the positive control Axl2 shRNA or the negative control Luc shRNA. Infected cells were selected with puromycin. These cells were then stained with antibodies against Axl protein and analyzed by FACS. L110 cells not infected with any shRNA were used as a control for Axl staining. L110 stained with secondary antibody only were used as a negative staining control. See FIG. 24. As expected, L110 cells carrying either no shRNA or the negative control Luc shRNA expressed a high levels of Axl protein (x-axis). L110 cells carrying the Axl2 shRNA had Axl protein levels reduced almost to the level of the secondary-antibody-only control. Thus, it is demonstrated that the Axl2 shRNA knocks down Axl protein, but the Luc shRNA does not.

4) Demonstration of the Reporter Assay

Figure 25A:
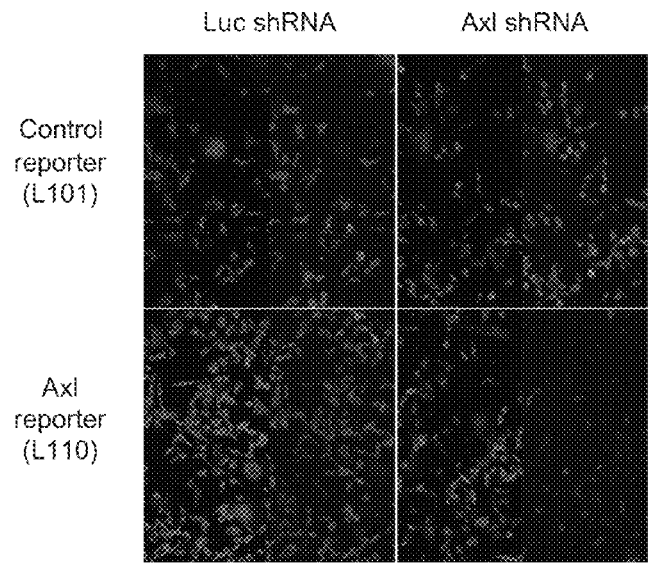
FIGS. 25A and B provide cell imaging and flow cytometry results demonstrating a reporter assay of the invention.

The reporter assay was further demonstrated by cell fluorescence imaging. See FIGS. 25A and B. L101 cells and L110 cells were each infected with retrovirus carrying either the positive control Axl2 shRNA or the negative control Luc shRNA. Infected cells were selected with puromycin. Selected cells were examined with a confocal microscope to visualise the GFP and RFP fluorescence (FIG. 25A). In the figure, both red fluorescence (from RFP) and green fluorescence (from GFP) are shown side-by-side for the same field of cells. Cells with red fluorescence are carrying and expressing an shRNA construct. The green fluorescence is the read-out from the GFP reporter assay.

It is clear from FIGS. 25A and B that the green fluorescence is reduced only in the bottom right panel. This corresponds to cells carrying the Axl-specific reporter (i.e., L110 cells) and the Axl-specific shRNA. Axl shRNA has no effect on the control reporter (L101 cells), and the control Luc shRNA has no effect on either reporter (L101 or L110 cells).

Figure 25B:
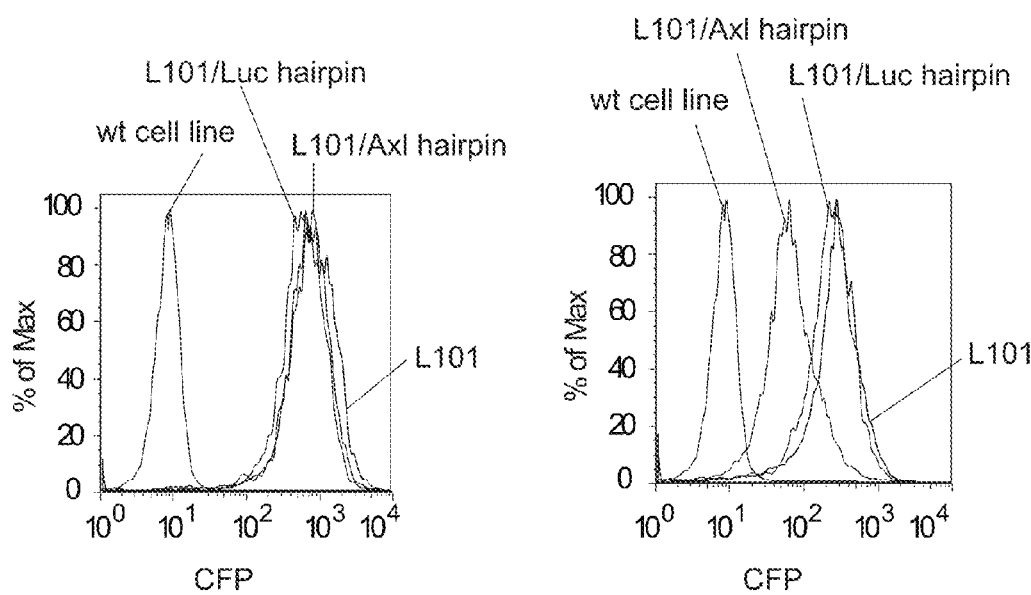

FIG. 25B shows the same cells analyzed by FACS, measuring the green fluorescent intensity. Fluorescence of L101 cells (top) is unaffected by either shRNA. Flourescence of L110 cells (bottom) is decreased in the presence of Axl shRNA (blue) but not Luc shRNA (green). Thus, the Axl reporter construct L110 therefore responds specifically to shRNAs targeting Axl.

5) Identification of Additional Axl Targeting shRNAS from the Library Produced in Step 1

Retrovirus prepared from clones from the library described in step 1 were individually infected into L110 cells and the GFP fluorescence measured. Two clones (Axl-278 and Axl-280) caused a reduction in the GFP fluorescence. The reduction in GFP fluorescence caused by Axl-280 was nearly as strong as the reduction seen with the control Axl2 shRNA, while Axl-278 produced a weaker reduction. See FIG. 26A.

6) Axl Protein Levels Correlate with Fluorescence from the Reporter Construct

The Axl protein levels correlate with fluorescence from the reporter construct. FIG. 26B shows a FACS analysis of the same cells as in FIG. 26A, but stained directly for Axl protein levels using the anti-Axl antibody. The reduction in Axl protein mirrors the reduction in GFP fluorescence, with Axl2 shRNA producing the strongest effect and Axl-278 producing the weakest effect. The relationship between the reporter fluorescence and the actual Axl protein level is nearly linear (FIG. 26C). The loss of fluorescence from the L110 GFP-PEST Axl reporter construct therefore closely reflects the amount of Axl protein knockdown.

7) Axl mRNA Levels Correlate with Fluorescence from the Reporter Construct

Figure 27A:
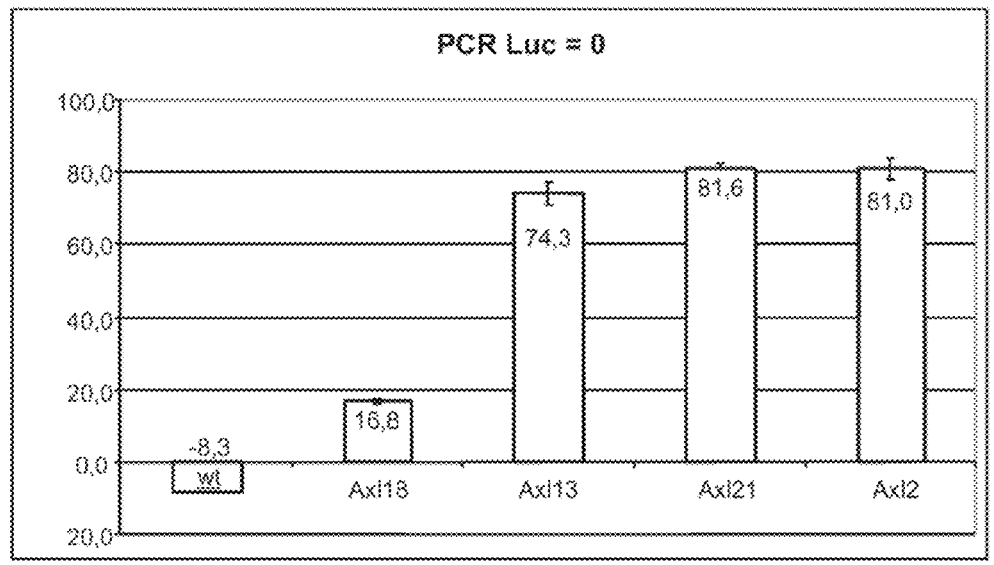
FIGS. 27A and B provide data that demonstrate that fluorescence from the reporter construct accurately mirrors endogenous mRNA levels.
Figure 27B:
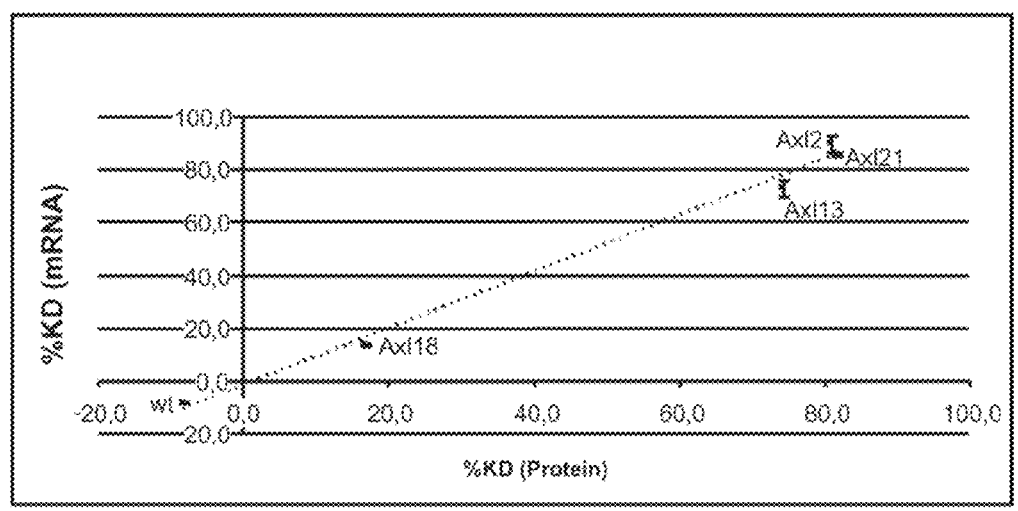
FIG. 27B shows a comparison of apparent Axl knockdown using quantitative RT-PCR (y-axis) or the GFP-PEST reporter assay (x-axis). There is a linear relationship between the knockdown measured using the reporter assay and the knockdown measured by quantitative RT-PCR.

Quantitative RT-PCR was used to measure Axl mRNA levels in L110 cells carrying different Axl-targeting shRNAs. In FIG. 27A, Axl21 is the same as Axl-280, Axl13 is the same as Axl-278 and Axl18 corresponds to a very weakly effective shRNA also known as Axl-279. The percent knockdown measured by RT-PCR correlates well with the percent knockdown measured by the reporter construct.

8) The Reporter Assay Works for Genes Other than Axl

In order to demonstrate that the RNAi-reporter assay system can be widely applicable to many genes for the identification of functional shRNA molecules, a reporter vector carrying a cDNA for human proteasomal subunit beta 5 (PSMB5 or beta5) was generated. This reporter was based on the L101 construct shown in FIG. 22. This GFP-PEST reporter was introduced into HSultan cells and monitored by flow cytometry. A non-target control RFP-shRNA luc construct expressing a shRNA directed against firefly luciferase was also introduced into the HSultan cells.

Figure 28A:
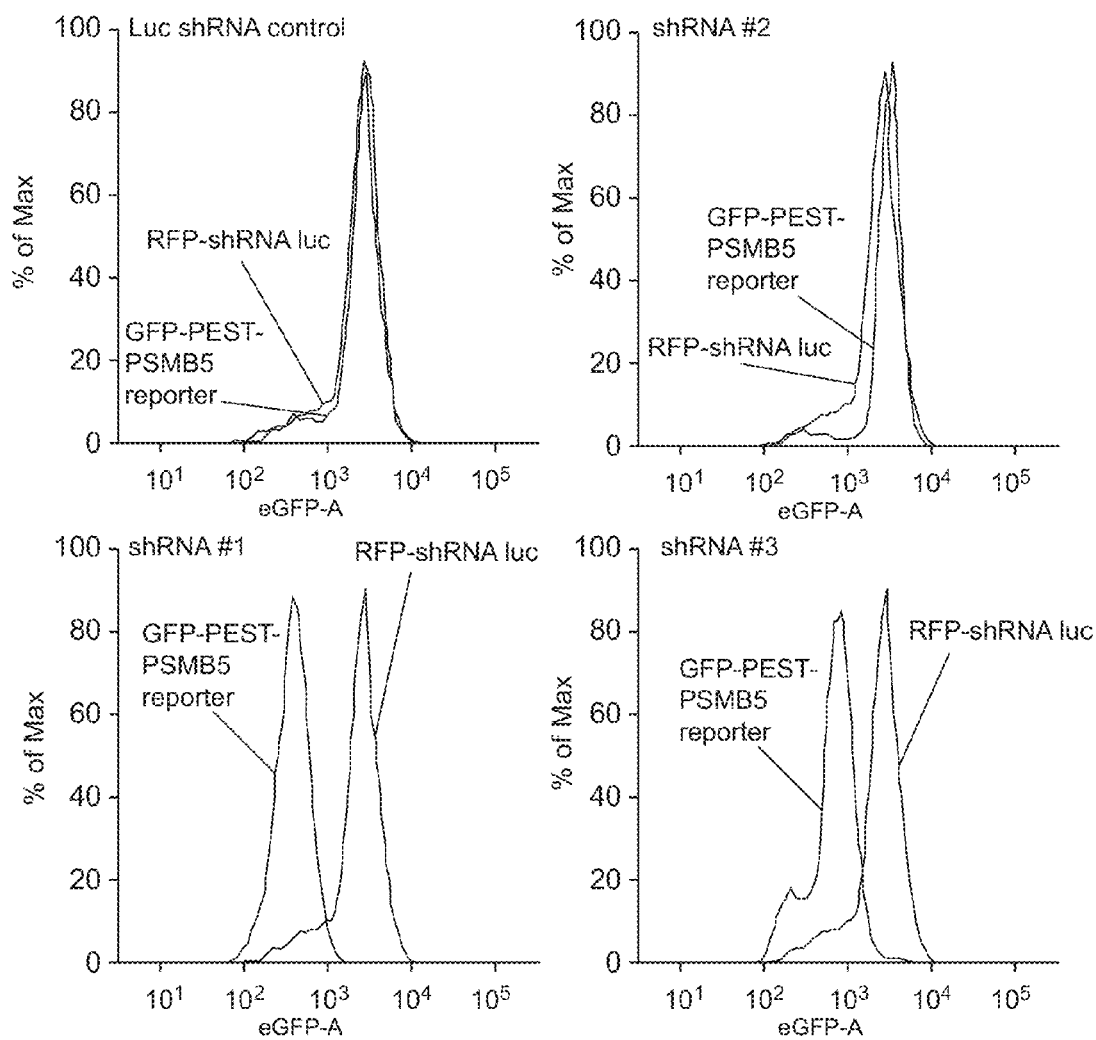
FIGS. 28A and 28B provide results illustrating use of the reporter assay to identify functional shRNA molecules.

Three previously known shRNA molecules that target proteasomal subunit beta 5 were introduced by retroviral transduction into the HSultan cells carrying the reporter constructs in order to demonstrate the effectiveness of this reporter system. Changes in the proteasomal subunit beta 5 RNAi reporter were measured by flow cytometry and is shown in FIG. 28A. The x-axis represents the signal observed from the reporter construct on a log scale. The y-axis represents the number of individual cells exhibiting that level of reporter expression.

In FIG. 28A, the top left panel shows the FACS analysis of HSultan cells carrying the PSMB5 reporter construct and HSultan cells carrying both the reporter construct and the non-target control shRNA construct RFP-shRNA luc. This plot confirms that the control shRNA construct has no effect on expression of the reporter construct. The bottom left panel (shRNA#1), top right panel (shRNA#2), bottom right panel (shRNA#3) show FACS analysis of HSultan cells carrying the reporter construct and either the non-target control shRNA construct RFP-shRNA luc or the candidate targeting shRNA construct (shRNA#1, #2, #3 respectively). In the two bottom panels, the PSMB5 reporter trace is shifted to the left compared to the control trace, indicating that the average signal from the reporter construct is lower.

Figure 28B:
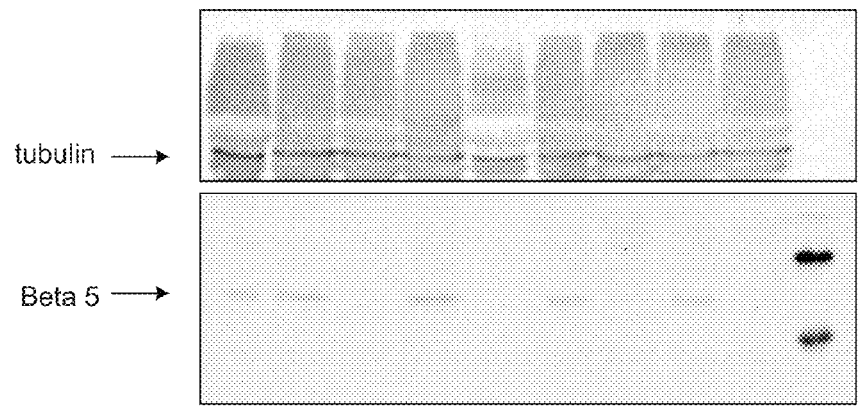

The analysis shows that the negative control (luc) and shRNA#2 do not affect proteasomal subunit beta 5 reporter expression levels, while shRNA#1 and shRNA#3 strongly reduce expression. See FIG. 28A. Western blot analysis of the proteasomal subunit beta 5 protein levels in the cell lines confirmed that shRNA#1 and shRNA#3 knocked down the endogenous beta 5 subunit protein production whereas shRNA#2 and the control Luc shRNA did not. (see FIG. 28B). This analysis confirms that that shRNA#1 and shRNA#3 are active RNAi trigger molecules for proteasomal subunit beta 5 target as measured in the RNAi reporter assay of the invention, but shRNA#2 did not demonstrate this activity.

Example 4

Identification of mRNA Sequences that are Targets for Orphan shRNA Molecules

This example describes the identification of "off-target" sequences that are targeted by known and previously isolated siRNA molecules. This method supposes that one has identified an shRNA that has an interesting biological effect, but for which the true target is unknown, i.e., the shRNA targets a gene other than the one it was designed against. The problem is to identify genes which the shRNA is able to down-regulate, as these are good candidates for the true target of the shRNA. Furthermore, the method is also applicable to identify targets of naturally occurring shRNA molecules (e.g., miRNA precursors) that have been isolated from cellular systems. This protocol is outlined generally in FIG. 29, and is described in detail below.
1) Preparation of a Plasmid Library A collection of cDNA clones covering all predicted human genes (or a suitable subset) can be obtained. An example of a suitable collection is the Human Unigene 4.1 set from RZPD. This collection contains around 30,000 cDNA clones covering most predicted human mRNAs. Alternatively, a suitable collection can be obtained by picking single clones from the large number of available human EST clones.

In a bulk cloning experiment, the cDNA sequences will be excised from their vectors, gel purified and ligated into the GFP-PEST vectors described herein. The ligation mix will be transformed into *E. coli* by electroporation to obtain a large number of colonies (>100,000). These colonies will be scraped and used to prepare plasmid DNA. This will produce a cDNA library in which each cDNA clone is placed downstream of GFP-PEST in our retroviral vector. The vector will also expresses the selectable marker for hygromycin resistance.
2) Preparation of the Retroviral Library The library above will be transfected into Phoenix packaging cells and the packaged retrovirus is collected. This produces a retroviral library. A sufficient number of Phoenix cells (e.g. >5,000,000) will be transfected to ensure that all members of the original cDNA library contribute to the retroviral library.
3) Preparation of the Assay Cells The retroviral library will be used to infect a suitable assay cell line (e.g., Jurkat cells or HL60 cells) to produce the assay library. Again, a sufficient number of cells (for example, greater than 5,000,000 cells) will be infected to ensure that all members of the original library are represented. The assay cells will be cultured in the presence of Hygromycin to select for cells infected with a retrovirus.

The assay cells will then be analyzed by FACS to determine their GFP expression levels. If the cells express GFP in a broad range of levels (as determined by GFP brightness) then they may be sorted into subpopulations (e.g., ten subpopulations) of different brightness, so that each subpopulation contains cells expressing a similar level of GFP.
4) Performing the Assay A large number of the assay cells from the previous step above (or of each subpopulation above) will be infected with a retrovirus expressing the shRNA to be tested. The shRNA expression vector used can contain the selectable marker RFP. The FACS sorter will be used to isolate individual cells that express the shRNA (assayed by RFP expression) and that also show reduced GFP expression, indicating that they carry a library member that is inhibited by the shRNA. The sorted cells will be allowed to replicate, and if necessary, subjected to further rounds of sorting.

Clones of sorted cells will then be subjected to PCR using primers flanking the cloning site in the GFP-PEST vector. This will amplify the cDNA insert present in the GFP-PEST vector. As an alternative, inverse PCR can be used. Each PCR product will be sequenced, thus revealing the identity of the cDNA(s) whose expression is regulated by the shRNA.

Example 5

Creating an Epi-allelic Series of Hypomorphic shRNA Molecules Directed to the Receptor Tyrosine Kinase Axl This Example examines the role of the receptor tyrosine kinase Axl in the invasiveness of breast carcinoma cells (Holland et al., "Multiple roles for the receptor tyrosine kinase Axl in tumor formation," *Cancer Res.*, 65:9294-303 (2005)). This is accomplished herein by constructing an epi-allelic series of hypomorphic shRNA molecules that target the endogenous Axl gene, and scoring the tumor invasiveness phenotype in the resulting Axl-knockdown cell lines. This analysis showed a correlation between Axl expression levels and invasiveness, possibly indicating that Axl facilitates the tumor cell's ability to invade surrounding tissue and promote metastasis.

The Axl receptor was originally identified as a transforming gene in chronic myeloid leukemia (Janssen et al., "A novel putative tyrosine kinase receptor with oncogenic potential," *Oncogene* 6:2113-2120 (1991); O'Bryan et al., "Axl, a transforming gene isolated from primary human myeloid leukemia cells, encodes a novel receptor tyrosine kinase," *Mol. Cell Biol.*, 11:5016-5031 (1991)), however its function has remained elusive. Axl is a unique member of the RTK family with an extracellular domain comprised of fibronectin III and Ig motifs similar to cadherin-type adhesion molecules. The Axl ligand, Gas6 (growth arrest specific-6), is a secreted protein belonging to the vitamin K-dependent protein family, related to blood coagulation factors (Melaragno et al., "The Gas6/Axl system: a novel regulator of vascular cell function," *Trends Cardiovasc. Med.*, 9:250-253 (1999)). While expressed in various organs during development, adult Axl expression is relatively restricted, predominating in the vasculature, mesenchymal cells and the myeloid lineage (Melaragno et al., "The Gas6/Axl system: a novel regulator of vascular cell function," *Trends Cardiovasc. Med.*, 9:250-253 (1999); Funakoshi et al., "Identification of Gas6, a putative ligand for Sky and Axl receptor tyrosine kinases, as a novel neurotrophic factor for hippocampal neurons," *J. Neurosci. Res.*, 68:150-

160 (2002)). Importantly, Axl and Gas6 expression are reported in a wide variety of solid human tumor types and myeloid leukemias (Sun et al., *Oncology* 66:450-457 (2004); Sun et al., *Ann. Oncol.*, 14:898-906 (2003); Chung et al., *DNA Cell Biol.*, 22:533-540 (2003); Berclaz et al., *Ann. Oncol.*, 12:819-824 (2001); Wimmel et al., *Eur. J. Cancer* 37:2264-2274 (2001)).

Generating a Hypomorphic Axl Series in Breast Carcinoma Cells

A small collection of candidate shRNA molecules targeting Axl were produced as described in Example 3. This library of candidate Axl-specific shRNA molecules was screened in a MDA-MB-231 breast carcinoma cell line as described in Example 3 to identify a plurality of shRNAs having a range of different silencing potentials.

Figure 30:
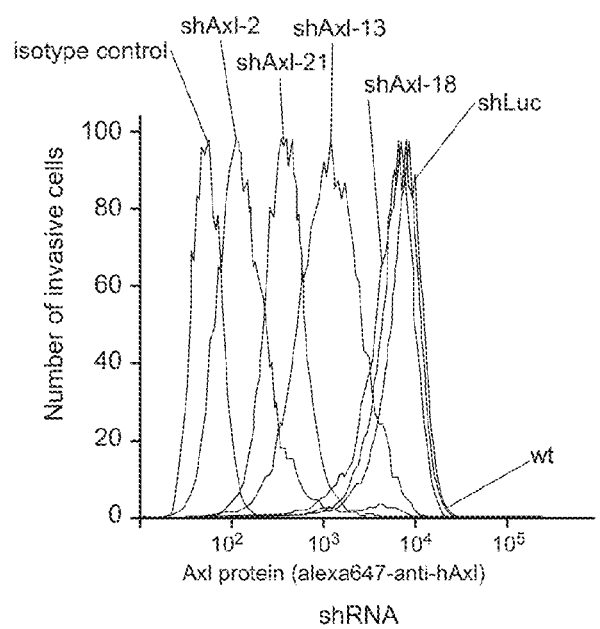
FIG. 30 provides a FACS analysis profile of MDA-MB-231 breast carcinoma cells expressing Axl-specific shRNA molecules. Cell surface Axl expression was assessed using a fluorescence-labelled anti-hAxl antibody.

This screening used MDA-MB-231 breast carcinoma host cells expressing Axl-specific shRNA molecules. The cells were analyzed by FACS using a fluorescence-labelled anti-hAxl antibody to measure cell surface Axl expression. The shRNA-expressing carcinoma cells and wild type (wt) MDA-MB-231 cells were stained with mouse anti-hAxl-Alexa647 conjugated mAb to detect Axl cell surface protein expression or mouse IgG-Alexa647 conjugated isotype control. Axl expression was analyzed by flow cytometry on FACSAria. As shown in FIG. 30, cells transduced with shAxl-2 or shAxl-21 showed a reduction of Axl protein expression to near background levels (compared to wt cells). Cells transduced with shAxl-13 showed intermediate knock down while shAxl-18 had only a very weak knockdown effect. Cells expressing the control shRNA targeting Luciferase (shLuc) showed equal Axl protein expression compared to the wt cell line.

Figure 31:
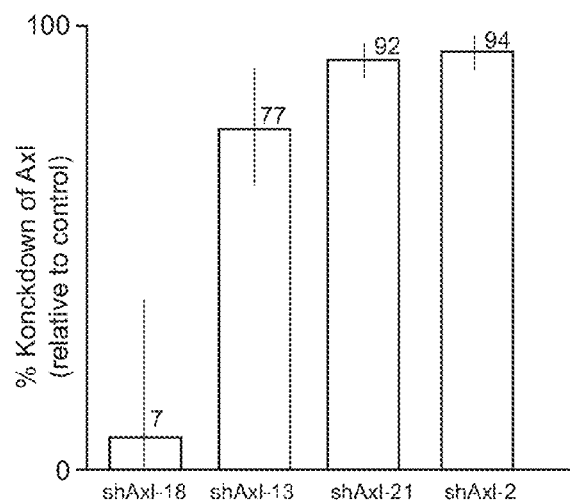
FIG. 31 provides a schematic representation of the data in FIG. 30, showing the mean±standard deviation from four independent experiments. Percent knockdown was calculated relative to the expression level seen with the control shLuc. The scale was normalized using the isotype control staining level to define 100% knockdown. The different shRNAs form an epi-allelic series, knocking down Axl to different degrees.

A schematic representation of this same date is shown in FIG. 31, where the mean±standard deviation from four independent experiments is shown. The percent knockdown was calculated relative to the expression level seen with the control shLuc. The scale was normalized using the isotype control staining level to define 100% knockdown. These knockdown efficiencies ranged from very weak (7%±30 for shAxl-18) to very strong (94%±4 for shAxl-2).

Figure 32:
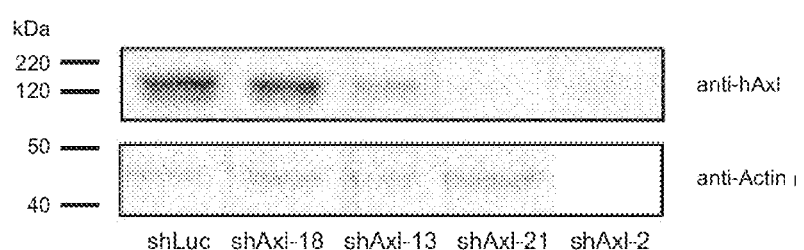
FIG. 32 provides a western blotting analysis of MDA-MB-231 cells expressing the various Axl-specific shRNA clones. The membrane was incubated with mouse anti-hAxl mAb or rabbit anti-Actin Ab, then incubated with HRP conjugated goat anti-mouse Ab or HRP conjugated goat anti-rabbit Ab and developed with ECL plus Western Blotting Detection System (Amersham Biosciences).

The ability of the shRNA isolates to knock down Axl expression was verified by western blotting analysis, as shown in FIG. 32. Infected MDA-MB-231 cells were lysed, separated by 10% SDS-PAGE and blotted. The membrane was incubated with mouse anti-hAxl mAb (R&D Systems) or rabbit anti-Actin Ab (Sigma) before they were incubated with HRP conjugated goat anti-mouse Ab or HRP conjugated goat anti-rabbit Ab. The blot was developed with ECL plus Western Blotting Detection System (Amersham Biosciences) and exposed in Fluor-S Multiimager (BioRad). Lane 1 shows total Axl protein expression in the control cell line shLuc while shAxl-18, shAxl-13, shAxl-21 and shAxl-2 are in lane 2-5, respectively. This western blot analysis was consistent with the FACS analysis, where the weak clone shAxl-18 showed weak knockdown of Axl protein expression, while the strong clones shAxl-2, 13 and 21 showed strong knockdown of Axl protein expression.

Axl Protein is Required for Invasiveness

Figure 33:
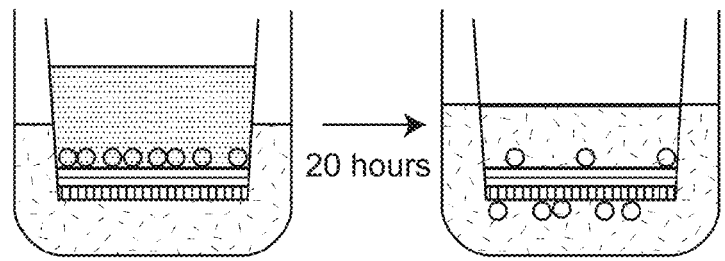
FIG. 33 provides an illustration of the in vitro culture Matrigel™ invasion assay. Cells to be tested are seeded in the inner wells of transwells coated with Matrigel™ and induced to migrate towards medium containing 20% serum. Cells that have migrated through the transwell are then counted.

In order to assess the role of Axl in breast carcinoma invasiveness, the MDA-MB-231 breast carcinoma host cells expressing either shRNAs targeting Axl or control shRNA targeting firefly luciferase were tested in an in vitro culture Matrigel™ invasion assay. The principle of the invasion assay is illustrated in FIG. 33. Cells to be tested are seeded in the inner wells of Transwells coated with Growth Factor Reduced Matrigel™ Matrix (BD Biosciences) at a concentration of $1\times10^5$ cells per well. The cells were induced to migrate towards F12-K medium (Gibco) containing 20% fetal bovine serum, for 20 hours in a $CO_2$-incubator. Non-invading cells on top of the Matrigel™ were removed with a cotton swab. The remaining cells were fixed in PFA, stained with DAPI and analyzed by fluorescence microscopy (4× magnification). Cell numbers were assayed using ImageJ software (NIH).

Figure 34:
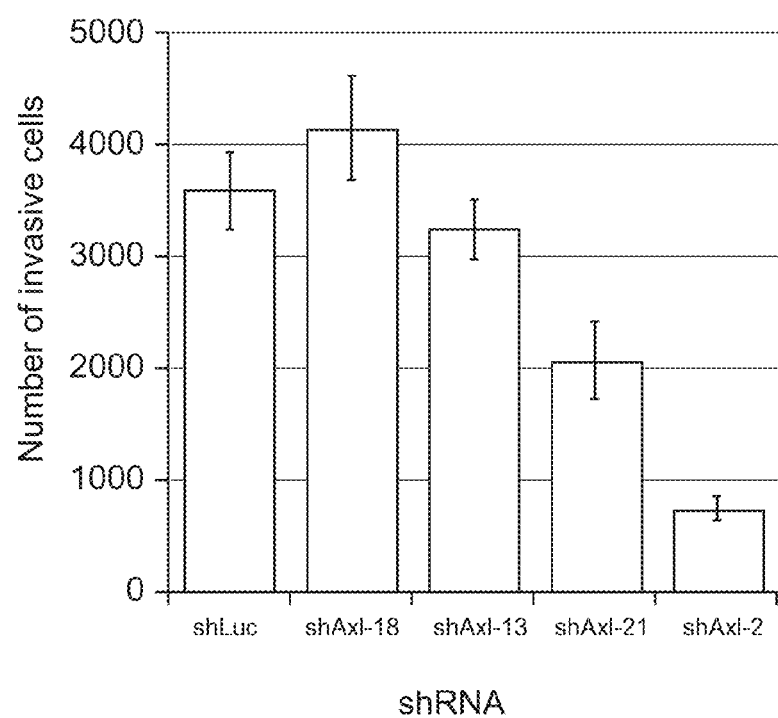
FIG. 34 provides a results summary of the Matrigel™ invasion assay measuring the effects of the Axl-specific shRNA hypomorphic series. The mean of two independent experiments ±SD is shown.

As shown in FIG. 34, MDA-MB-231 breast carcinoma cell invasiveness correlates with Axl expression levels. This figure shows the mean of 2 independent experiments ±SD. MDA-MB-231 cells showing weak knockdown of Axl (e.g., using shAxl-18) did not demonstrate any reduced invasive phenotype compared to the control cell line (shLuc), while cells with intermediate (shAxl-13) or strong (shAxl-21, shAxl-2) knockdown of Axl showed progressively stronger reduction in invasion. This reduction in invasiveness is not due to a reduction in proliferation (data not shown).

In Vivo Target Validation by Epi-allelic Analysis: In Vivo Bioluminescent Image Analysis of Subcutaneous MB-MDA-231/CSI-Axl shRNA Epi-allelic Breast Carcinoma Cells The MB-MDA-231 epi-allelic cell series created by the present invention can be used to correlate expression of a selected gene with in vivo growth of tumor cells, an important step in the validation therapeutic targets for cancer treatment. The MB-MDA-231 epi-allelic cell series was transduced with a firefly luciferase gene retroviral construct (CSI). The luciferase gene allows the in vivo detection of bioluminescence following intravenous injection of luciferin. Bioluminescence is detected and quantified in an optical imager.

Figure 38:
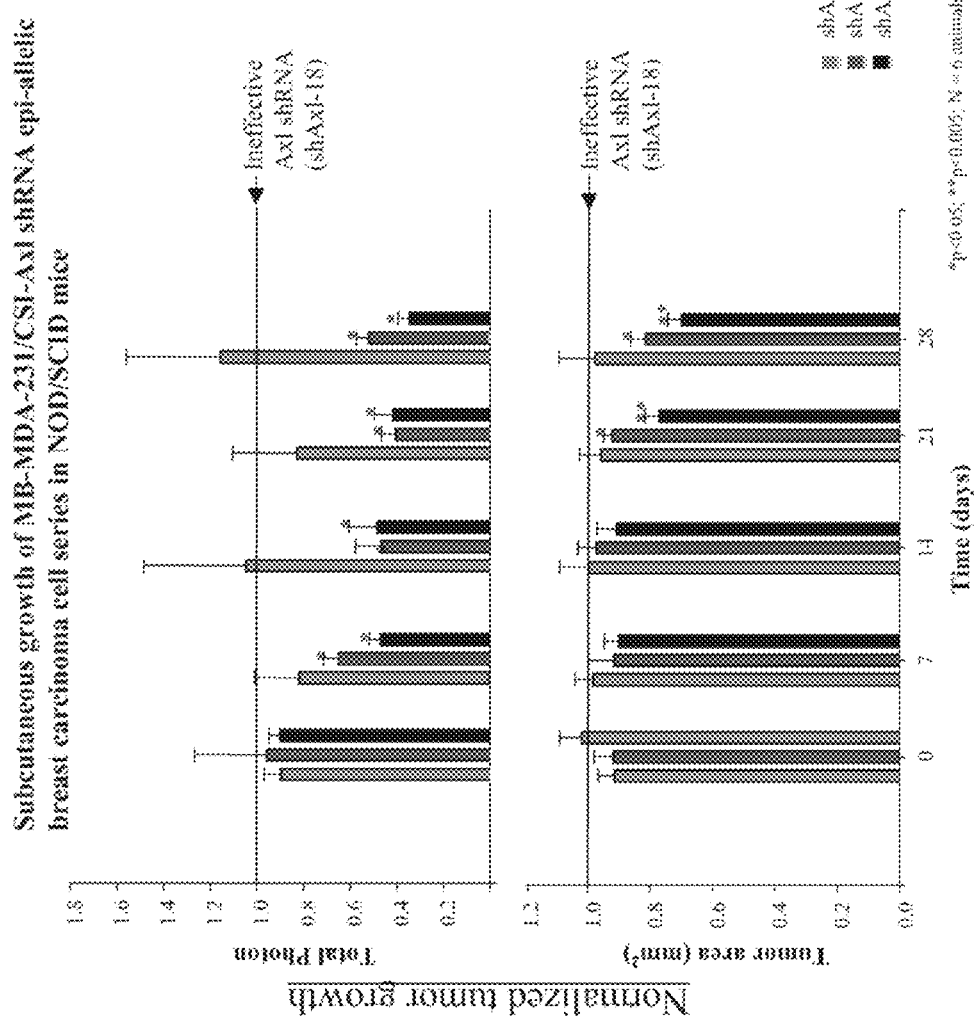
FIG. 38 provides the results from an in vivo bioluminescent image analysis of subcutaneous tumors comprising Axl shRNA epi-allelic breast carcinoma cells.

One million cells of each MB-MDA-231 epi-allelic cell line were implanted subcutaneously into NOD/SCID mice as per Holland et al., "Multiple roles for the receptor tyrosine kinase Axl in tumor formation," *Cancer Res.*, 65:9294-303 (2005). Growth of the implanted MB-MDA-231 epi-allelic cell line was monitored weekly by in vivo bioluminescent image analysis. Total photons captured determined overall tumor growth. Tumor area represented the maximal circumference of the tumor image and is related to lateral spread of the tumor implant. Data was normalized to growth of MB-MDA-231 cells expressing the ineffective Axl-targeting shRNA-18, which does not inhibit MB-MDA-231 cell growth in vivo and is indistinguishable from wild type MB-MDA-231 cells. As shown in FIG. 38, MB-MDA-231 epi-allelic cell series tumor formation in vivo during a 28-day period is correlated with Axl expression. Tumor formation (total photon measurement) is dose dependent (FIG. 38, top panel), with tumor development displaying a distinct threshold defined by the shAxl-21-determined Axl expression level. Radial invasiveness (tumor area) also shows a genetic dose dependence on Axl expression (FIG. 38, bottom panel). This data demonstrates that MB-MDA-231 cell growth in vivo is dependent on the expression of Axl and that epi-allelic analysis by the current invention can be used to define beneficial therapeutic expression thresholds for putative therapeutic targets.

Conclusions

Using RNA interference, we demonstrate that the receptor tyrosine kinase Axl is required to maintain the invasive and tumorigenic phenotype of the malignant breast carcinoma cell line, MDA-MB-231. Using the novel methods for construction, screening and identification of active RNAi trigger molecules, several shRNA molecules were identified that reduce Axl cell surface expression to different levels. This Axl hypomorphic series, representing a "genetic dose response" established a correlation between Axl expression and malignancy of MDA-MB-231 cells. From these results it is postulated that Axl expression improves the ability of breast carcinoma cells to invade and co-opt the surrounding supportive stroma and may play an important role in metastasis. Thus, the methods described here establish Axl as a unique target for cancer therapeutic development.

Example 6

Creating an Epi-allelic Series of Hypomorphic shRNA Molecules Directed to the Receptor Tyrosine Kinase Akt This Example describes the generation of an epi-allelic series of hypomorphic shRNA molecules directed to the serine/threonine-specific protein kinase signaling protein Akt1 oncogene (also known as protein kinase B).

Figure 36:
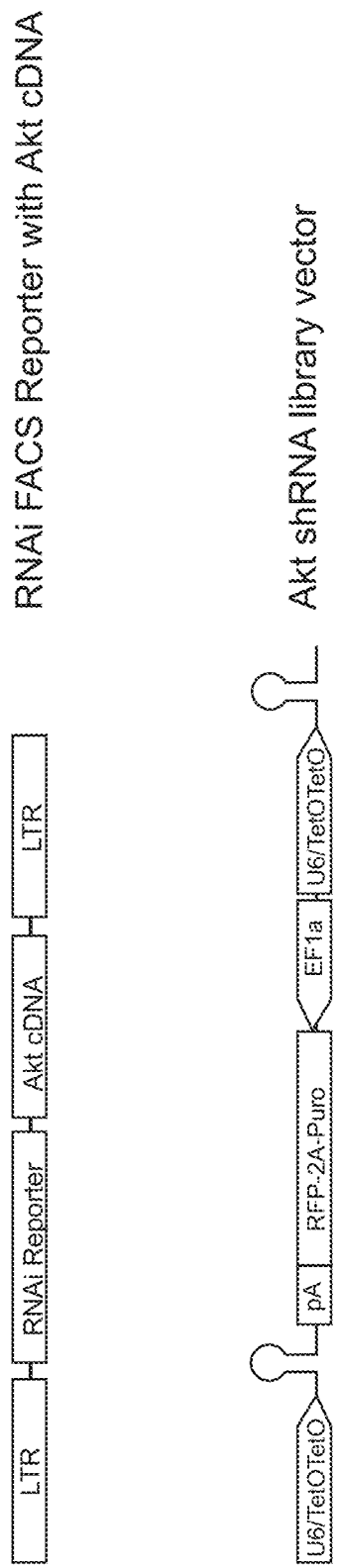
FIG. 36 provides a schematic of the RNAi screening FACS reporter construct and the Axl shRNA library vector construct used to identify RNAi trigger molecules specific for the Akt oncogene.

A library of shRNA molecules targeting Akt was constructed as described in Example 2, but starting with an Akt cDNA rather than the VEGFR2 cDNA. In addition to intermediate vector L267 described in Example 2, tagged hairpin loops were also cloned into two alternative intermediate vectors with slightly different modifications to the U6 promoter sequence and cloning sites compared to those in L267. These were L266 which has an AfeI site instead of the NaeI site, and L308 which uses a PshA1 site instead of the NaeI site, and introduces an additional G residue at the location corresponding to the initiation of transcription. Hairpin loops in all three intermediate vectors were treated identically to L267 as in Example 2 to produce a final library of candidate shRNA molecules targeting Akt1. This shRNA library vector is shown schematically in FIG. 36.

Over one thousand colonies from the retroviral vector library were sequenced. Approximately 60% carried inserts with the expected hairpin structure, targeting Akt1.

A reporter vector for Akt1 was produced by cloning the Akt1 cDNA into vector L101 (FIG. 22) in a manner similar to that described in Example 3. This reporter vector is shown schematically in FIG. 36. The reporter vector was introduced into HL60 cells, chosen because they are particularly well suited to FACS sorting. Selection with hygromycin yielded an Akt reporter cell line of HL60 cells carrying the Akt1 reporter vector construct.

In four independent experiments run in parallel, a large number of Akt1 reporter cells were infected with retrovirus prepared from Phoenix cells transfected with the Akt-targeting retroviral vector library. The cells were treated for several days with puromycin to select reporter cells also carrying an shRNA construct.

Reporter cells carrying an shRNA construct were then sorted on a FACSAria. Cells which both expressed RFP (and therefore carry an shRNA construct) and had low GFP expression (indicating successful knockdown of the reporter) were sorted into pools of 10 or 100 cells. The shRNA cassettes within each pool of 10 or 100 cells were recovered by PCR with primers that incorporated a barcode tag. A different barcode was used for each pool of 10 or 100 sequences so that the sequence of each PCR product would reveal which pool (and therefore also which independent parallel experiment) the PCR product was derived from.

PCR products from all the pools of all the independent parallel experiments were pooled and subjected to massively parallel sequencing on a 454 pyrosequencer, yielding over 10,000 sequences. These sequences were then examined to identify shRNAs that were present in at least one pool from each of at least three of the four independent parallel experiments. These shRNAs were considered as primary hits in the screen for shRNAs targeting Akt1. The shRNA molecules that were not consistently selected in multiple independent parallel experiments were assumed to represent random false positives and not processed further.

* * *

One of skill in the art will recognize that various materials and methods that are similar or equivalent to those described herein can be used in the construction and practice of the present invention. It is not intended that the invention be limited to the particular materials and methods cited herein, and it is intended that similar and equivalent materials and methods not recited herein are also within the scope of the invention.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

---

What is claimed is:

1. A method of testing for the presence or absence of specific inhibitory activity of an RNAi trigger molecule for a polynucleotide target, the method comprising:
   (a) providing a cell comprising:
      i) a reporter construct comprising a reporter transcription unit, the reporter transcription unit comprising (A) a translatable reporter gene polynucleotide encoding a reporter polypeptide, and (B) a nontranslatable target polynucleotide or a portion thereof, the target polynucleotide positioned 3' to the reporter gene polynucleotide wherein the translatable reporter gene polynucleotide and the nontranslatable target polynucleotide are from different genes; and
      ii) a vector encoding an RNAi trigger molecule;
   (b) culturing said first cell under conditions that permit expression of the reporter transcription unit and the RNAi trigger molecule;
   (c) detecting a signal associated with the cell, said signal corresponding to a level of expression of the reporter polypeptide in the cell; and
   (d) correlating the detected signal with specific inhibitory activity of the RNAi trigger molecule for the target polynucleotide, thereby testing for the presence or absence of specific inhibitory activity of the RNAi trigger molecule for the polynucleotide target.

2. The method of claim 1, wherein the target polynucleotide is (i) an mRNA, (ii) a cDNA encoding the mRNA, or (iii) a portion of (i) or (ii).

3. The method of claim 1, wherein the RNAi trigger molecule is selected from a double-stranded RNA, a short hairpin RNA (shRNA), a micro RNA (miRNA), a shmiRNA, and a small interfering RNA (siRNA).

4. The method of claim 1, wherein the reporter gene polynucleotide encodes a fusion reporter polypeptide.

5. The method of claim 1, wherein the reporter gene polynucleotide further encodes a PEST motif, and said reporter polypeptide is a fusion polypeptide comprising the PEST motif.

6. The method of claim 1, wherein detecting comprises detecting with single-cell resolution.

7. The method of claim 1, wherein the reporter transcription unit is operably linked to a transcription promoter.

8. The method of claim 1, wherein the reporter gene encodes a fluorescent reporter polypeptide.

9. The method of claim 1, wherein the reporter gene encodes a fluorescent reporter polypeptide selected from a green fluorescent protein, a red fluorescent protein, a yellow fluorescent protein, and a blue fluorescent protein.

10. The method of claim 1, wherein the reporter gene encodes a cell surface marker polypeptide.

11. The method of claim 1, wherein the reporter gene encodes a Lyt2 cell surface marker polypeptide.

12. The method of claim 1, wherein the reporter gene encodes a negative selection marker.

13. The method of claim 1, wherein the reporter gene encodes a negative selection marker selected from thymidine kinase (tk), HRPT, and APRT.

14. The method of claim 1, wherein the reporter gene encodes a reporter polypeptide selected from a luciferase polypeptide, a β-galactosidase, α-lactamase, an alkaline phosphatase, and a horse-radish peroxidase.

15. The method of claim 1, wherein the vector is selected from a retroviral vector, a lentiviral vector, an adenoviral vector, and a eukaryotic expression vector.

16. The method of claim 1, wherein detecting a signal associated with each cell comprises detecting fluorescence by fluorescence activated cell sorting (FACS).

17. The method of claim 1, wherein detecting a signal associated with each cell comprises detecting a magnetic tag by magnetic flow cell sorting.

* * * * *